(12) United States Patent
Masaeli et al.

(10) Patent No.: US 11,815,507 B2
(45) Date of Patent: Nov. 14, 2023

(54) SYSTEMS AND METHODS FOR PARTICLE ANALYSIS

(71) Applicant: Deepcell, Inc., Mountain View, CA (US)

(72) Inventors: Mahdokht Masaeli, San Jose, CA (US); Mahyar Salek, San Jose, CA (US); Hou-Pu Chou, Sunnyvale, CA (US); Soroush Kahkeshani, Sunnyvale, CA (US); Prashast Khandelwal, Mountain View, CA (US); Syed Tariq Shafaat, Sunnyvale, CA (US)

(73) Assignee: Deepcell, Inc., Menlo Park, CA (US)

( * ) Notice: Subject to any disclaimer, the term of this patent is extended or adjusted under 35 U.S.C. 154(b) by 196 days.

(21) Appl. No.: 17/173,636

(22) Filed: Feb. 11, 2021

(65) Prior Publication Data

US 2021/0405022 A1 Dec. 30, 2021

Related U.S. Application Data

(63) Continuation of application No. PCT/US2019/046557, filed on Aug. 14, 2019, which
(Continued)

(51) Int. Cl.
*G01N 33/49* (2006.01)
*G01N 1/30* (2006.01)
(Continued)

(52) U.S. Cl.
CPC .............. *G01N 33/491* (2013.01); *G01N 1/30* (2013.01); *G01N 15/1463* (2013.01);
(Continued)

(58) Field of Classification Search
CPC .............. G01N 33/491; G01N 15/1463; G01N 2015/0073; G01N 2015/008; G01N 2015/1445; G01N 2015/149
(Continued)

(56) References Cited

U.S. PATENT DOCUMENTS 5,804,143 A 9/1998 Leary et al.
6,025,128 A 2/2000 Veltri et al.
(Continued)

FOREIGN PATENT DOCUMENTS

CN 101765762 A 6/2010
CN 104136907 A 11/2014
(Continued)

OTHER PUBLICATIONS

Aus Der Wi Esche, S. et al., "Dynamics in Microfluidic Systems With Microheaters", Technical Proceedings of the 1999 Conference on Modelling and Simulation of Microsystems, Apr. 1999, pp. 510-513.
(Continued)

*Primary Examiner* — Christine T Mui
(74) *Attorney, Agent, or Firm* — Wilson Sonsini Goodrich & Rosati

(57) ABSTRACT

The present disclosure provides systems and methods for sorting a cell. The system may comprise a flow channel configured to transport a cell through the channel. The system may comprise an imaging device configured to capture an image of the cell from a plurality of different angles as the cell is transported through the flow channel. The system may comprise a processor configured to analyze the image using a deep learning algorithm to enable sorting of the cell.

20 Claims, 12 Drawing Sheets

Related U.S. Application Data is a continuation-in-part of application No. 16/194,269, filed on Nov. 16, 2018, now Pat. No. 10,611,995.

(60) Provisional application No. 62/764,965, filed on Aug. 15, 2018.

(51) Int. Cl.
    *G01N 15/14* (2006.01)
    *G01N 15/00* (2006.01)

(52) U.S. Cl.
    CPC .................. *G01N 2015/008* (2013.01); *G01N 2015/0073* (2013.01); *G01N 2015/149* (2013.01); *G01N 2015/1445* (2013.01); *G01N 2015/1493* (2013.01); *G01N 2015/1497* (2013.01)

(58) Field of Classification Search
    USPC .......................................................... 435/15
    See application file for complete search history.

(56) References Cited

U.S. PATENT DOCUMENTS

| | | |
|---|---|---|
| 6,947,586 B2 | 9/2005 | Kasdan et al. |
| 6,960,449 B2 | 11/2005 | Wang et al. |
| 7,210,937 B1 | 5/2007 | Raghu |
| 7,450,229 B2 | 11/2008 | Ortyn et al. |
| 7,482,577 B2 | 1/2009 | Gruber et al. |
| 8,186,913 B2 | 5/2012 | Toner et al. |
| 8,465,706 B2 | 6/2013 | Attinger et al. |
| 8,610,085 B2 | 12/2013 | Patt |
| 8,778,279 B2 | 7/2014 | Durack |
| 8,935,098 B2 | 1/2015 | Di et al. |
| 9,177,192 B2 | 11/2015 | Wang et al. |
| 9,328,344 B2 | 5/2016 | Link et al. |
| 9,333,510 B2 | 5/2016 | Di Carlo et al. |
| 9,495,742 B2 | 11/2016 | Lagae et al. |
| 10,611,995 B2 | 4/2020 | Masaeli et al. |
| 10,808,219 B2 | 10/2020 | Masaeli et al. |
| 10,843,196 B2 | 11/2020 | Masaeli et al. |
| 11,015,165 B2 | 5/2021 | Masaeli et al. |
| 2005/0179968 A1 | 8/2005 | Molteni et al. |
| 2008/0213821 A1 | 9/2008 | Liu et al. |
| 2009/0066936 A1 | 3/2009 | Huang et al. |
| 2009/0181421 A1 | 7/2009 | Kapur et al. |
| 2011/0136165 A1 | 6/2011 | Vojnovic et al. |
| 2012/0035061 A1 | 2/2012 | Bransky et al. |
| 2012/0058480 A1 | 3/2012 | Lewis et al. |
| 2012/0063664 A1 | 3/2012 | Di Carlo et al. |
| 2012/0196314 A1 | 8/2012 | Nawaz et al. |
| 2013/0130226 A1 | 5/2013 | Lim et al. |
| 2013/0222547 A1 | 8/2013 | Van Rooyen et al. |
| 2013/0258091 A1 | 10/2013 | Ozcan et al. |
| 2014/0071452 A1 | 3/2014 | Fleischer |
| 2014/0224710 A1 | 8/2014 | Di Carlo et al. |
| 2014/0376816 A1 | 12/2014 | Lagae et al. |
| 2015/0087007 A1 | 3/2015 | Meldrum et al. |
| 2015/0308941 A1 | 10/2015 | Di Carlo et al. |
| 2016/0084750 A1 | 3/2016 | Wang et al. |
| 2017/0052106 A1 | 2/2017 | Hennig et al. |
| 2017/0248512 A1 | 8/2017 | Di Carlo et al. |
| 2017/0333902 A1 | 11/2017 | Masaeli et al. |
| 2017/0333903 A1 | 11/2017 | Masaeli et al. |
| 2017/0356914 A1 | 12/2017 | Weichert et al. |
| 2018/0156710 A1 | 6/2018 | Vrane |
| 2021/0245158 A1 | 8/2021 | Masaeli et al. |

FOREIGN PATENT DOCUMENTS

| | | | |
|---|---|---|---|
| CN | 105247042 A | | 1/2016 |
| CN | 109154601 A | | 1/2019 |
| DE | 102014205535 A1 | | 10/2015 |
| EP | 3458857 A1 | | 3/2019 |
| GB | 2566847 A | | 3/2019 |
| JP | 2009536313 A | | 10/2009 |
| JP | 2010538241 A | | 12/2010 |
| JP | 2019518448 A | | 7/2019 |
| WO | WO-0101025 A2 | | 1/2001 |
| WO | WO-2016054293 A1 | | 4/2016 |
| WO | WO-2017201495 A1 | | 11/2017 |
| WO | WO-2017201546 A1 | | 11/2017 |
| WO | WO-2020037070 A1 | | 2/2020 |

OTHER PUBLICATIONS

Bluma, Arne et al., "In-Situ Imaging Sensors for Bioprocess Monitoring: State of the Art", Anal Bioanal Chem, vol. 398, Sep. 12, 2010, pp. 2429-2438.

Camisard, V. et al., "Inline Characterization of Cell Concentration and Cell Volume in Agitated Bioreactors Using In Situ Microscopy: Application to Volume Variation Induced by Osmotic Stress", Biotechnology and Bioengineering, vol. D 78, No. 1, Apr. 5, 2002, pp. 73-80.

Chen, C.C. et al., "Micromachined Bubble-Jet Cell Sorter With Multiple Operation Modes", Sensors and Actuators, B vol. 117, Jul. 7, 2006, pp. 523-529.

Chen, et al., Deep Learning in Label-free Cell Classification. Scientific Reports, Mar. 15, 2016, vol. 6, Article 21471, 16 pgs.

Co-pending U.S. Appl. No. 17/240,327, inventors Masaelimahdokht et al., filed Apr. 26, 2021.

Di Carlo, D., Inertial microfluidics. Lab on chip, 2008 9(21): 3038.

Eisenstein, Michael, "Divide and Conquer", Nature, vol. 441, Jun. 29, 2006, p. 1179.

Extended European Search Report for European Application No. 17800306.7, Search completed Jun. 3, 2019, dated Jun. 12, 2019, 10 Pgs.

Goda, et al., High-throughput single-microparticle imaging flow analyzer. Proceedings of the National Academy of Sciences (PNAS), Jul. 17, 2012, vol. 109, No. 29, pp. 11630-11635.

Hou, Jian-Mei et al., "Circulating Tumor Cells, Enumeration and Beyond", Cancers, vol. 2, Jun. 9, 2010, pp. 1236-1250.

Ijsselmuiden, Alexander J.J. et al., "Circulating White Blood Cells and Platelets Amplify Oxidative Stress in Heart Failure", Nature Clinical Practice, Cardiovascular Medicine, vol. 5, No. 12, Dec. 2008, pp. 811-820.

International Preliminary Report on Patentability for International Application PCT/US2017/033676, Report dated Nov. 20, 2018, dated Nov. 29, 2018, 7 Pgs.

International Preliminary Report on Patentability for International Application PCT/US2017/033889, Report dated Nov. 20, 2018, dated Nov. 29, 2018, 8 Pgs.

International Search Report and Written Opinion for International Application No. PCT/US2017/033676, Search completed Jul. 22, 2017, dated Aug. 11, 2017, 11 Pgs.

International Search Report and Written Opinion for International Application No. PCT/US2017/033889, Search completed Jul. 26, 2017, dated Aug. 25, 2017, 9 Pgs.

Jemal, et al., Cancer Statistics, CA Cancer J Clin. Sep.-Oct. 2010;60(5):277-300. doi: 10.3322/caac.20073. Epub Jul. 7, 2010.

Joeris, Klaus et al., "In-Situ Microscopy: Online Process Monitoring of Mammalian Cell Cultures", Cytotechnology, vol. 38, Mar. 31, 2002, pp. 129-134.

Moon, SangJun et al., "Integrating Microfluidics and Lensless Imaging for Point-of-Care Testing", Biosensors and Bioelectronics, vol. 24, Apr. 2, 2009, pp. 3208-3214.

Moon, SangJun et al., "Lensless Imaging for Point-of-Care Testing", 31st Annual International Conference of the IEEE EMBS, Minneapolis, Minnesota, Sep. 2-6, 2009, pp. 6376-6379.

Nitta, et al., Intelligent Image-activated cell sorting. Cell, Sep. 20, 2018; 175:1-11.

PCT/US2019/046557 International Search Report and Written Opinion dated Dec. 13, 2019.

Rehbock, Christoph et al., "Development of a Flow-Through Microscopic Multitesting System for Parallel Monitoring of Cell Samples in Biotechnological Cultivation Processes", Journal of Biotechnology, vol. 150, Jul. 8, 2010, pp. 87-93.

(56) References Cited

OTHER PUBLICATIONS

Seo, Sungkyu et al., "Lensfree Holographic Imaging for On-Chip Cytometry and Diagnostics", Lab on a Chip, vol. 9, Mar. 21, 2009, pp. 777-787.
U.S. Appl. No. 14/363,373 Office Action dated Nov. 23, 2015.
U.S. Appl. No. 15/600,618 Office Action dated Feb. 11, 2020.
U.S. Appl. No. 15/600,618 Office Action dated Mar. 22, 2019.
U.S. Appl. No. 15/600,618 Office Action dated Oct. 3, 2018.
U.S. Appl. No. 15/600,618 Office Action dated Sep. 16, 2019.
U.S. Appl. No. 16/194,269 Notice of Allowance dated Feb. 3, 2020.
U.S. Appl. No. 16/194,269 Notice of Allowance dated Nov. 21, 2019.
U.S. Appl. No. 16/194,269 Office Action dated Jul. 5, 2019.
U.S. Appl. No. 16/839,555 Notice of Allowance dated Aug. 19, 2020.
U.S. Appl. No. 16/839,555 Office Action dated May 7, 2020.
U.S. Appl. No. 17/071,421 Notice of Allowance dated Mar. 19, 2021.
U.S. Appl. No. 17/071,421 Office Action dated Dec. 4, 2020.
Vona, Giovanna et al., "Technical Advance. Isolation by Size of Epithelial Tumor Cells. A New Method for the Immunomorphological and Molecular Characterization of Circulating Tumor Cells", American Journal of Pathology, vol. D 156, No. 1, Jan. 2000, pp. 57-63.
Went, Philip et al., "Frequent EpCam Protein Expression in Human Carcinomas", Human Pathology, vol. 35, No. 1, Jan. 2004, pp. 122-128.
Zeng, et al., Microfluidic Investigation of the Mechanical Behavior of Red Blood Cells Entering a Constriction. University of California, Davis, ProQuest Dissertations Publishing, 2014.
Zheng, et al., Hydrodynamically controlled cell rotation in an electroporation microchip to circumferentially deliver molecules into single cells. published online, Jan. 7, 2016, Microfluid Nanofluid (2016}20: 16 (pp. 1-12).

SYSTEMS AND METHODS FOR PARTICLE ANALYSIS

CROSS-REFERENCE

This application is a continuation of International Application No. PCT/US19/46557, filed Aug. 14, 2019, which is a continuation-in-part of U.S. patent application Ser. No. 16/194,269, filed Nov. 16, 2018, which claims the benefit of U.S. Provisional Patent Application No. 62/764,965, filed Aug. 15, 2018, each of which is entirely incorporated herein by reference.

BACKGROUND

Cell physical and morphological properties can be used to study cell type and cell state and to diagnose diseases. Cell shape is one of the markers of cell cycle. Eukaryotic cells show physical changes in shape which can be cell-cycle dependent, such as a yeast cell undergoing budding or fission. Shape is also an indicator of cell state and can become an indicator used for clinical diagnostics. Blood cell shape may change due to many clinical conditions, diseases, and medications, such as the changes in red blood cells' morphologies resulting from parasitic infections. Other parameters such as features of cell membrane, nuclear-to-cytoplasm ratio, nuclear envelope morphology, and chromatin structure can also be used to identify cell type and disease state. In blood, for instance, different cell types are distinguished by factors such as cell size, cell shape, and nuclear shape.

Biologists and cytopathologists use cell size and morphology to identify cell type and diagnose disease. This is mainly done by some sort of microscopic imaging and manual analysis of the images. As a result, the existing methods are time consuming, subjective, qualitative, and prone to error. Cytopathologists, for instance, review slides prepared from different tissues using a light microscope and look for features that resemble characteristics of disease. This process is time-consuming and the results are subjective and may be impacted by factors such as the orientation of the stained cells, how the slide was prepared, and the expertise of the cytopathologists. Although there have been recent efforts to automate the analysis of cytology smears, there are still challenges. One of the main problems with the analysis of the smears is the existence of contaminant cells that are hard to avoid and make it difficult to detect rare cells or specific feature characteristics of disease. Other issues are the angles of the stained or smeared cells, which can obscure essential information for identification of a cell type or state. As such, there remains a need for improved methods and/or systems for cell analysis.

SUMMARY

In an aspect, the present disclosure provides a method of sorting a cell, comprising: (a) transporting a cell through a flow channel; (b) capturing a plurality of images of the cell from a plurality of different angles as the cell is transported through the flow channel; and (c) analyzing the plurality of images using a deep learning algorithm to sort the cell.

In some embodiments, the method further comprises rotating the cell as the cell is being transported through the flow channel. In some embodiments, the method further comprises applying a velocity gradient across the cell to rotate the cell. In some embodiments, the cell is flown in a first buffer at a first velocity, and wherein the applying the velocity gradient across the cell comprises co-flowing a second buffer at a second velocity. In some embodiments, an axis of the rotation of the cell and an additional axis of migration of the cell along the flow channel are different. In some embodiments, the axis of the rotation of the cell is perpendicular to the additional axis of the migration of the cell along the flow channel.

In some embodiments, the method further comprises focusing the cell into a streamline at a height within the flow channel as the cell is being transported through the flow channel. In some embodiments, the focusing comprises subjecting the cell under an inertial lift force, wherein the inertial lift force is characterized by a Reynolds number of greater than 1. In some embodiments, the inertial lift force is characterized by a Reynolds number of at least 20.

In some embodiments, the plurality of images is captured at a rate of about 10 frames per second to about 500,000 frames per second.

In some embodiments, the plurality of angles extends around the cell or over a portion of the cell.

In some embodiments, the plurality of images of the cell are captured from (1) a top side of the cell, (2) a bottom side of the cell, (3) a front side of the cell, (4) a rear side of the cell, (5) a left side of the cell, or (6) a right side of the cell. In some embodiments, the plurality of images of the cell are captured from at least two sides selected from the group consisting of: (1) a top side of the cell, (2) a bottom side of the cell, (3) a front side of the cell, (4) a rear side of the cell, (5) a left side of the cell, and (6) a right side of the cell.

In some embodiments, the method further comprises sorting the cell based on the analyzed plurality of images, by directing the cell to a selected channel of a plurality of channels downstream of the flow channel. In some embodiments, the plurality of channels excluding the selected channel are closed prior to directing the cell to the selected channel. In some embodiments, the plurality of channels excluding the selected channel are closed using pressure, an electric field, a magnetic field, or a combination thereof. In some embodiments, the method further comprises validating the sorting of the cell using a light. In some embodiments, the validating comprises determining information associated with the cell using blockage or scattering of the light. In some embodiments, the information associated with the cell comprises a size, shape, density, texture, or speed of the cell. In some embodiments, the validating comprises (i) providing at least two light spots on the selected channel by directing at least two lights towards the selected channel, and (ii) determining a travel time of the cell between the at least two light sports, wherein the at least two light spots are spaced apart by about 10 micrometer to about 1,000 micrometer. In some embodiments, the light comprises a laser. In some embodiments, the sorting comprises (i) directing a first cell to a first channel of the plurality of channels and (ii) directing a second cell to a second channel of the plurality of channels, wherein the first cell and the second cell have or are suspected of having one or more different features.

In some embodiments, the method further comprises sorting a plurality of cells at a rate of at least 10 cells per second, wherein the plurality of cells comprises the cell.

In some embodiments, the method further comprises sorting a plurality of cells comprising the cell using a classifier; and feeding data from the sorting back to the classifier in order to train the classifier for future sorting. In some embodiments, the classifier comprises a neural network. In some embodiments, the classifier is configured to perform classification of each of the plurality of cells, based on classification probabilities corresponding to a plurality of analyzed plurality of images of the plurality of cells.

In some embodiments, the cell is from a biological sample of a subject, and wherein the method further comprises determining a presence or an absence of a condition or an attribute in the subject based on the analyzed plurality of images. In some embodiments, the biological sample of the subject is selected from the group consisting of: blood, plasma, serum, urine, perilymph fluid, feces, saliva, semen, amniotic fluid, cerebrospinal fluid, bile, sweat, tears, sputum, synovial fluid, vomit, bone, heart, thymus, artery, blood vessel, lung, muscle, stomach, intestine, liver, pancreas, spleen, kidney, gall bladder, thyroid gland, adrenal gland, mammary gland, ovary, prostate gland, testicle, skin, adipose, eye, brain, infected tissue, diseased tissue, malignant tissue, calcified tissue, and healthy tissue. In some embodiments, the malignant tissue comprises tumor, sarcoma, leukemia, or a derivative thereof.

In some embodiments, the capturing comprises illuminating the cell with a strobe light with an exposure time of less than 1 millisecond, wherein the strobe light comprises a wavelength selected from the group consisting of: 470 nanometer (nm), 530 nm, 625 nm, and 850 nm.

In some embodiments, the method further comprises (i) analyzing each of the plurality of images using an ensemble of deep learning algorithms to classify the cell at each of the plurality of different images at each of the plurality of different angles, and (ii) aggregating a plurality of classifications of the cell from the analyzing to determine a final classification of the cell.

In some embodiments, the cell is from a maternal serum. In some embodiments, the method further comprises identifying a nucleated red blood cell (RBC), wherein presence of the nucleated RBC is indicative of a fetal abnormal condition. In some embodiments, the fetal abnormal condition is fetal aneuploidy.

In some embodiments, the method further comprises (i) predicting an arrival time of the cell at a sorting junction, and (ii) adjusting a velocity of the cell to modify the arrival time of the cell at the sorting junction if the predicted arrival time of the cell is (1) before completion of step (c) or (2) before completion of actuating one or more valves at the sorting junction. In some embodiments, the method further comprises determining a probability of the cell arriving at the sorting junction at the predicted arrival time. In some embodiments, the adjusting the velocity of the cell comprises decreasing the velocity of the cell. In some embodiments, the velocity of the cell is adjusted to delay the arrival time of the cell at the sorting junction. In some embodiments, the method further comprises (iii) detecting an actual arrival time of the cell at the sorting junction, and (iv) modifying one or more cell analysis algorithms and/or actuation signals of the one or more valves based on a comparison of the predicted arrival time and the actual arrival time. In some embodiments, (iv) is performed in real time.

In some embodiments, the method further comprises (i) providing a population of cells comprising the cell, (ii) analyzing a subpopulation of the population of cells for a first time to detect a target cell, (iii) if a number of the target cell in the subpopulation is above a predetermined threshold number, collect the subpopulation, and (iv) analyzing the subpopulation for a second time. In some embodiments, the method further comprises, in (ii), capturing one or more images of each cell of the subpopulation. In some embodiments, the method further comprises capturing a single image of each cell from a single angle. In some embodiments, the predetermined threshold number is at least 1 target cell. In some embodiments, the predetermined threshold number is at least 2 target cells. In some embodiments, the predetermined threshold number is at least 5 target cells. In some embodiments, the subpopulation comprises at least about 10 cells. In some embodiments, the subpopulation comprises at least about 50 cells. In some embodiments, the subpopulation comprises at least about 100 cells. In some embodiments, the method further comprises, in (iv), (1) capturing a plurality of images of each cell of the subpopulation, (2) analyzing each of the plurality of images, (3) classifying each cell of the subpopulation, and (4) sorting each cell of the subpopulation.

In some embodiments, the method further comprises (i) capturing one or more images of at least one of the sorted cells, and (ii) analyzing the one or more images using the deep learning algorithm to classify the at least one sorted cell. In some embodiments, the method further comprises modifying one or more cell analysis algorithms based on the analysis of the at least one sorted cell. In some embodiments, the method further comprises performing the modifying in real time.

In an aspect, the present disclosure provides a system for sorting a cell, comprising: a flow channel configured to transport a cell through the flow channel; an imaging device configured to capture a plurality of images of the cell from a plurality of different angles as the cell is transported through the flow channel; and a processor configured to analyze the plurality of images using a deep learning algorithm to sort the cell.

In some embodiments, the system is further configured to rotate the cell as the cell is being transported through the flow channel. In some embodiments, the system is further configured to apply a velocity gradient across the cell to rotate the cell. In some embodiments, the flow channel is configured to transport the cell in a first buffer at a first velocity through the flow channel, and wherein the system is further configured to co-flow a second buffer at a second velocity through the flow channel, thereby to apply the velocity gradient across the cell. In some embodiments, an axis of the rotation of the cell and an additional axis of migration of the cell along the flow channel are different. In some embodiments, the axis of the rotation of the cell is perpendicular to the additional axis of the migration of the cell along the flow channel.

In some embodiments, the system is further configured to focus the cell into a streamline at a height within the flow channel as the cell is being transported through the flow channel. In some embodiments, the system is configured to subject the cell under an inertial lift force to focus the cell, wherein the inertial lift force is characterized by a Reynolds number of greater than 1. In some embodiments, the inertial lift force is characterized by a Reynolds number of at least 20.

In some embodiments, a width or a height of the flow channel is non-uniform along an axis of the flow channel. In some embodiments, the width or the height of the flow channel gradually increases along a direction of the flow channel through which the cell is transported.

In some embodiments, the flow channel comprises walls that are formed to focus the cell into a streamline.

In some embodiments, the plurality of images is captured at a rate of about 10 frames per second to about 500,000 frames per second.

In some embodiments, the plurality of angles extends around the cell or over a portion of the cell.

In some embodiments, the plurality of images of the cell are captured from (1) a top side of the cell, (2) a bottom side of the cell, (3) a front side of the cell, (4) a rear side of the cell, (5) a left side of the cell, or (6) a right side of the cell. In some embodiments, the plurality of images of the cell are captured from at least two sides selected from the group consisting of: (1) a top side of the cell, (2) a bottom side of the cell, (3) a front side of the cell, (4) a rear side of the cell, (5) a left side of the cell, and (6) a right side of the cell.

In some embodiments, each of the plurality of images comprises a two-dimensional image or a three-dimensional image.

In some embodiments, the flow channel is configured to transport a plurality of cells through the flow channel, wherein the plurality of cells comprises the cell, and wherein the imaging device is further configured to capture one or more images of the plurality of cells as the plurality of cells are transported through the flow channel. In some embodiments, the imaging device is configured to capture a single image of the plurality of cells. In some embodiments, the imaging device is configured to individually capture one or more images of each of the plurality of cells. In some embodiments, the imaging device is configured to capture the one or more images of the plurality of cells from a plurality of different angles relative to each of the plurality of cells.

In some embodiments, the flow channel branches into a plurality of channels downstream of the flow channel, and wherein the system is configured to sort the cell based on the analyzed plurality of images, by directing the cell to a selected channel of the plurality of channels. In some embodiments, one or more of the plurality of channels comprises a valve configured to modulate flow through the one or more of the plurality of channels. In some embodiments, the valve is a pressure valve, an electric field valve, or a magnetic field valve. In some embodiments, the plurality of channels excluding the selected channel are closed prior to directing the cell to the selected channel. In some embodiments, the system further comprises a validation module configured to detect the cell after the cell has been sorted, and validate the sorting of the cell based on the detection. In some embodiments, the validation module is configured to provide light to the cell to determine information associated with the cell, wherein the detection is based on blockage of scattering of the light by the cell. In some embodiments, the information associated with the cell comprises a size, shape, density, texture, or speed of the cell. In some embodiments, the validation module is configured to (i) provide at least two light spots on the selected channel by directing at least two lights towards the selected channel, and (ii) determine a travel time of the cell between the at least two light sports, wherein the at least two light spots are spaced apart by about 10 micrometer to about 1,000 micrometer. In some embodiments, the light comprises a laser. In some embodiments, the system is configured to sort the cell by (i) directing a first cell to a first channel of the plurality of channels and (ii) directing a second cell to a second channel of the plurality of channels, wherein the first cell and the second cell have or are suspected of having one or more different features.

In some embodiments, the processor is configured to sort a plurality of cells at a rate of at least 10 cells per second, wherein the plurality of cells comprises the cell.

In some embodiments, the processor is configured to (i) use a classifier to sort a plurality of cells comprising the cell, and (ii) feed data from the sorting back to the classifier in order to train the classifier for future sorting. In some embodiments, the classifier comprises a neural network. In some embodiments, the classifier is configured to perform classification of each of the plurality of cells, based on classification probabilities corresponding to a plurality of analyzed plurality of images of the plurality of cells.

In some embodiments, the cell is from a biological sample of a subject, and wherein the method further comprises determining a presence or an absence of a condition or an attribute in the subject based on the analyzed plurality of images. In some embodiments, the biological sample of the subject is selected from the group consisting of: blood, plasma, serum, urine, perilymph fluid, feces, saliva, semen, amniotic fluid, cerebrospinal fluid, bile, sweat, tears, sputum, synovial fluid, vomit, bone, heart, thymus, artery, blood vessel, lung, muscle, stomach, intestine, liver, pancreas, spleen, kidney, gall bladder, thyroid gland, adrenal gland, mammary gland, ovary, prostate gland, testicle, skin, adipose, eye, brain, infected tissue, diseased tissue, malignant tissue, calcified tissue, and healthy tissue. In some embodiments, the malignant tissue comprises tumor, sarcoma, leukemia, or a derivative thereof.

In some embodiments, the imaging device is configured to capture the plurality of images by illuminating the cell with a strobe light with an exposure time of less than 1 millisecond, wherein the strobe light comprises a wavelength selected from the group consisting of: 470 nanometer (nm), 530 nm, 625 nm, and 850 nm.

In some embodiments, the processor is further configured to (i) analyze each of the plurality of images using an ensemble of deep learning algorithms to classify the cell at each of the plurality of different images at each of the plurality of different angles, and (ii) aggregate a plurality of classifications of the cell from the analyzing to determine a final classification of the cell.

In some embodiments, the cell is from a maternal serum. In some embodiments, the processor is configured to, based on the analyzing, identify a nucleated red blood cell (RBC), wherein presence of the nucleated RBC is indicative of a fetal abnormal condition. In some embodiments, the fetal abnormal condition is fetal aneuploidy.

In some embodiments, the system is further configured to (i) predict an arrival time of the cell at a sorting junction, and (ii) adjust a velocity of the cell to modify the arrival time of the cell at the sorting junction if the predicted arrival time of the cell is (1) before completion of the analyzing or (2) before completion of actuating one or more valves at the sorting junction. In some embodiments, the system is further configured to determine a probability of the cell arriving at the sorting junction at the predicted arrival time. In some embodiments, the adjusting the velocity of the cell comprises decreasing the velocity of the cell. In some embodiments, the velocity of the cell is adjusted to delay the arrival time of the cell at the sorting junction. In some embodiments, the system is further configured to (iii) detect an actual arrival time of the cell at the sorting junction, and (iv) modify one or more cell analysis algorithms and/or actuation signals of the one or more valves based on a comparison of the predicted arrival time and the actual arrival time. In some embodiments, (iv) is performed in real time.

In some embodiments, the system is configured to further comprising (i) analyze a subpopulation of a population of cells for a first time to detect a target cell, (ii) if a number of the target cell in the subpopulation is above a predetermined threshold number, collect the subpopulation, and (iii) analyze the subpopulation for a second time. In some embodiments, the imaging device is configured to capture one or more images of each cell of the subpopulation. In some embodiments, the imaging device is configured to capture a single image of each cell from a single angle. In some embodiments, the predetermined threshold number is at least 1 target cell. In some embodiments, the predetermined threshold number is at least 2 target cells. In some embodiments, the predetermined threshold number is at least 5 target cells. In some embodiments, the subpopulation comprises at least about 10 cells. In some embodiments, the subpopulation comprises at least about 50 cells. In some embodiments, the subpopulation comprises at least about 100 cells. In some embodiments, the system is configured to analyze the subpopulation for the second time by (1) capturing a plurality of images of each cell of the subpopulation, (2) analyzing each of the plurality of images, (3) classifying each cell of the subpopulation, and (4) sorting each cell of the subpopulation.

In some embodiments, the system is further configured to (i) capture one or more images of at least one of the sorted cells, and (ii) analyze the one or more images using the deep learning algorithm to classify the at least one sorted cell. In some embodiments, the imaging device or an additional imaging device is configured to capture the one or more images of the at least one of the sorted cells. In some embodiments, the processor or an additional processor is configured to analyze the one or more images using a deep learning algorithm to classify the at least one sorted cell. In some embodiments, the system is further configured to modify one or more cell analysis algorithms based on the analysis of the at least one sorted cell. In some embodiments, the modifying is performed in real time.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications, and NCBI accession numbers mentioned in this specification are herein incorporated by reference to the same extent as if each individual publication, patent, patent application, or NCBI accession number was specifically and individually indicated to be incorporated by reference. To the extent publications and patents, patent applications, or NCBI accession numbers incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

DETAILED DESCRIPTION

While various embodiments of the disclosure have been shown and described herein, it will be obvious to those skilled in the art that such embodiments are provided by way of example only. Numerous variations, changes, and substitutions may occur to those skilled in the art without departing from the disclosure. It should be understood that various alternatives to the embodiments of the disclosure described herein may be employed.

Unless defined otherwise, all technical and scientific terms used herein have the same meaning as commonly understood by one of ordinary skill in the art to which the present disclosure belongs. In case of conflict, the present application including the definitions will control. Also, unless otherwise required by context, singular terms shall include pluralities and plural terms shall include the singular.

Classification and/or Sorting Systems

In an aspect, the present disclosure describes a cell sorting system. The cell sorting system can comprise a flow channel configured to transport a cell through the channel. The cell sorting system can comprise an imaging device configured to capture an image of the cell from a plurality of different angles as the cell is transported through the flow channel. The cell sorting system can comprise a processor configured to analyze the image using a deep learning algorithm to enable sorting of the cell. The cell sorting system can be a cell classification system. In some cases, the flow channel can be configured to transport a solvent (e.g., liquid, water, media, alcohol, etc.) without any cell. The cell sorting system can have one or more mechanisms (e.g., a motor) for moving the imaging device relative to the channel. Such movement can be relative movement, and thus the moving piece can be the imaging device, the channel, or both. The processor can be further configured to control such relative movement.

Figures 1A, 1B:
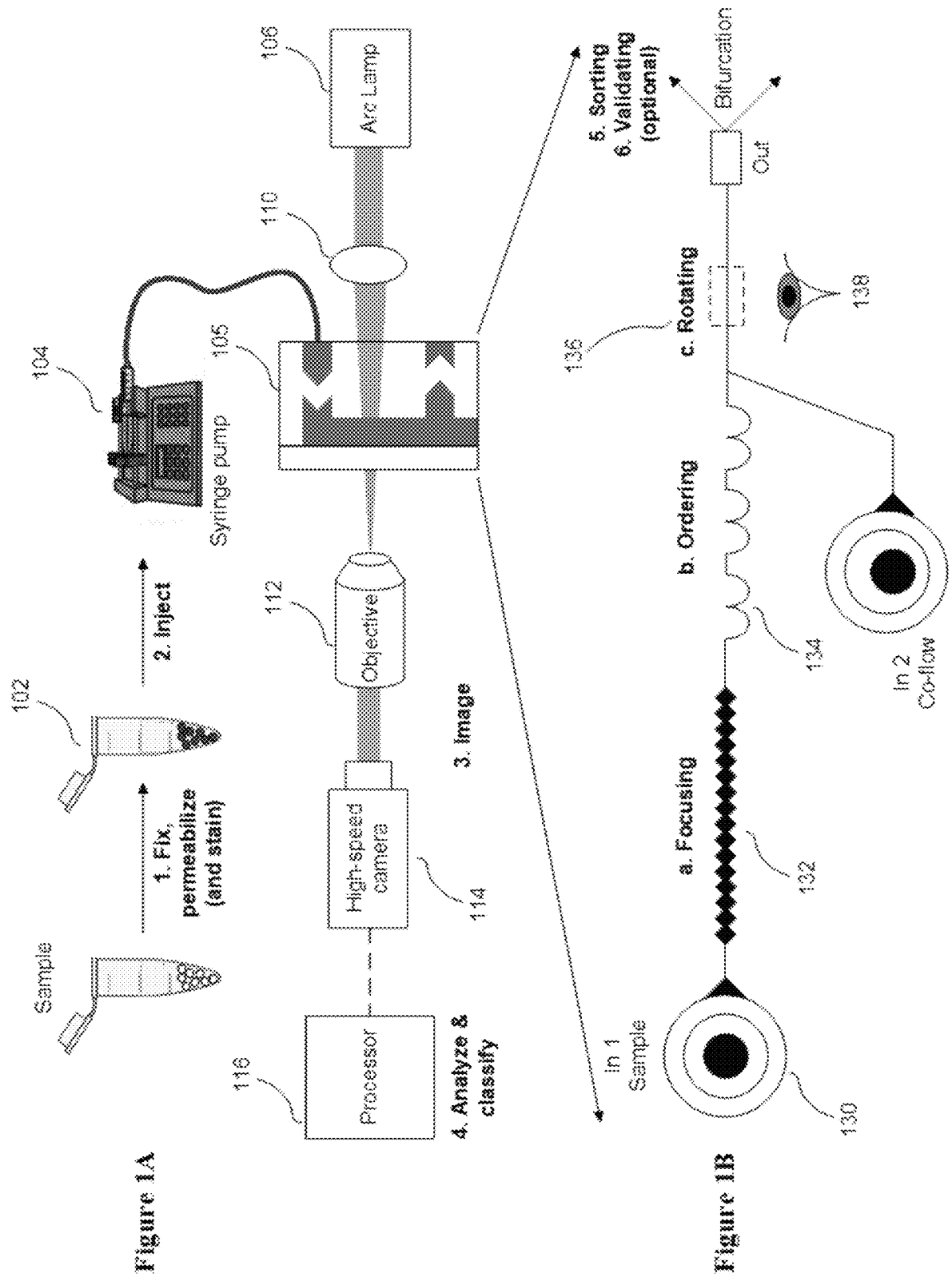
FIG. 1A conceptually illustrates a classification and/or sorting system in accordance with one embodiment of the disclosure.
FIG. 1B conceptually illustrates a microfluidic design of a flow cell in accordance with one embodiment of the disclosure.

In some embodiments, the disclosure provides a classification and/or sorting system as illustrated in FIG. 1A shows a schematic illustration of the cell sorting system with a flow cell design (e.g., a microfluidic design), with further details illustrated in FIG. 1B. In operation, a sample 102 is prepared and injected by a pump 104 (e.g., a syringe pump) into a flow cell 105, or flow-through device. In some embodiments, the flow cell 105 is a microfluidic device. Although FIG. 1A illustrates a classification and/or sorting system utilizing a syringe pump, any of a number of perfusion systems can be used such as (but not limited to) gravity feeds, peristalsis, or any of a number of pressure systems. In some embodiments, the sample is prepared by fixation and staining. In some examples, the sample comprises live cells. As can readily be appreciated, the specific manner in which the sample is prepared is largely dependent upon the requirements of a specific application.

In some embodiments, a cell suspension sample is prepared at concentrations ranging between $1\times10^4$-$5\times10^6$ cells/mL. In some embodiments, a cell suspension sample is prepared at concentrations ranging between $1\times10^4$-$5\times10^4$ cells/mL. In some embodiments, a cell suspension sample is prepared at concentrations ranging between $5\times10^4$-$1\times10^5$ cells/mL. In some embodiments, a cell suspension sample is prepared at concentrations ranging between $1\times10^5$-$5\times10^5$ cells/mL. In some embodiments, a cell suspension sample is prepared at concentrations ranging between $5\times10^5$-$1\times10^6$ cells/mL. In some embodiments, a cell suspension sample is prepared at concentrations ranging between $1\times10^6$-$5\times10^6$ cells/mL. In some embodiments, a cell suspension sample is prepared at concentrations ranging between $5\times10^4$-$5\times10^5$ cells/mL. In some embodiments, a cell suspension sample is prepared at concentrations ranging between $1\times10^4$-$5\times10^5$ cells/mL. In some embodiments, a cell suspension sample is prepared at concentrations ranging between $5\times10^4$-$1\times10^6$ cells/mL. In some embodiments, a cell suspension sample is prepared at concentrations ranging between $2\times10^5$-$5\times10^5$ cells/mL. In some embodiments, a cell suspension sample is prepared at concentrations ranging between $3\times10^5$-$5\times10^5$ cells/mL. In some embodiments, a cell suspension sample is prepared at concentrations ranging between $4\times10^5$-$5\times10^5$ cells/mL. In some embodiments, a cell suspension sample is prepared at concentrations ranging between $1\times10^5$-$4\times10^5$ cells/mL. In some embodiments, a cell suspension sample is prepared at concentrations ranging between $2\times10^5$-$4\times10^5$ cells/mL. In some embodiments, a cell suspension sample is prepared at concentrations ranging between $3\times10^5$-$4\times10^5$ cells/mL. In some embodiments, a cell suspension sample is prepared at concentrations ranging between $1\times10^5$-$3\times10^5$ cells/mL. In some embodiments, a cell suspension sample is prepared at concentrations ranging between $2\times10^5$-$3\times10^5$ cells/mL. In some embodiments, a cell suspension sample is prepared at concentrations ranging between $1\times10^5$-$2\times10^5$ cells/mL.

In some embodiments, a cell suspension sample is prepared at a concentration of about $1\times10^4$ cells/mL, about $5\times10^4$ cells/mL, about $1\times10^5$ cells/mL, about $2\times10^5$ cells/mL, about $3\times10^5$ cells/mL, about $4\times10^5$ cells/mL, about $5\times10^4$ cells/mL, about $5\times10^5$ cells/mL, about $1\times10^6$ cells/mL, or about $5\times10^6$ cells/mL.

The specific concentration utilized in a given classification and/or sorting system typically depends upon the capabilities of the system. Cells may be fixed and stained with colored dyes (e.g., Papanicolaou and Wright Giemsa methods). Classification and/or sorting systems in accordance with various embodiments of the disclosure can operate with live, fixed and/or Wright Giemsa-stained cells. Staining can help increase the contrast of nuclear organelles and improve classification accuracy. In some embodiments the cells in the sample are not labelled and/or stained. After preparation, the cell suspension sample can be injected into the microfluidic device using a conduit such as (but not limited to) tubing and a perfusion system such as (but not limited to) a flow unit.

Examples of the flow unit may be, but are not limited to, a syringe pump, a vacuum pump, an actuator (e.g., linear, pneumatic, hydraulic, etc.), a compressor, or any other suitable device to exert pressure (positive, negative, alternating thereof, etc.) to a fluid that may or may not comprise one or more particles (e.g., one or more cells to be classified, sorted, and/or analyzed). The flow unit may be configured to raise, compress, move, and/or transfer fluid into or away from the microfluidic channel. In some examples, the flow unit may be configured to deliver positive pressure, alternating positive pressure and vacuum pressure, negative pressure, alternating negative pressure and vacuum pressure, and/or only vacuum pressure. The flow cell of the present disclosure may comprise at least 1, 2, 3, 4, 5, 6, 7, 8, 9, 10, or more flow units. The flow cell may comprise at most 10, 9, 8, 7, 6, 5, 4, 3, 2, or 1 flow unit.

Each flow unit may be in fluid communication with at least 1, 2, 3, 4, 5, 6, 7, 8, 9, 10, or more sources of fluid. Each flow unit may be in fluid communication with at most 10, 9, 8, 7, 6, 5, 4, 3, 2, or 1 fluid. The fluid may contain the particles (e.g., cells). Alternatively, the fluid may be particle-free. The flow unit may be configured to maintain, increase, and/or decrease a flow velocity of the fluid within the microfluidic channel of the flow unit. Thus, the flow unit may be configured to maintain, increase, and/or decrease a flow velocity (e.g., downstream of the microfluidic channel) of the particles. The flow unit may be configured to accelerate or decelerate a flow velocity of the fluid within the microfluidic channel of the flow unit, thereby accelerating or decelerating a flow velocity of the particles.

The fluid may be liquid or gas (e.g., air, argon, nitrogen, etc.). The liquid may be an aqueous solution (e.g., water, buffer, saline, etc.). Alternatively, the liquid may be oil. In some cases, only one or more aqueous solutions may be directed through the microfluidic channels. Alternatively, only one or more oils may be directed through the microfluidic channels. In another alternative, both aqueous solution(s) and oil(s) may be directed through the microfluidic channels. In some examples, (i) the aqueous solution may form droplets (e.g., emulsions containing the particles) that are suspended in the oil, or (ii) the oil may form droplets (e.g., emulsions containing the particles) that are suspended in the aqueous solution.

In some embodiments, a syringe pump injects the sample at about 10 µL/min. In some embodiments, a syringe pump injects the sample at about 50 µL/min. In some embodiments, a syringe pump injects the sample at about 100 µL/min. In some embodiments, a syringe pump injects the sample at about 150 µL/min. In some embodiments, a syringe pump injects the sample at about 200 µL/min. In some embodiments, a syringe pump injects the sample at about 250 µL/min. In some embodiments, a syringe pump injects the sample at about 500 µL/min. In some embodiments, a syringe pump injects the sample at about 10 µL/min to about 500 µL/min, for example at about 10 µL/min to about 50 µL/min, about 10 µL/min to about 100 µL/min, about 10 µL/min to about 150 µL/min, about 10 µL/min to about 200 µL/min, about 10 µL/min to about 250 µL/min, about 10 µL/min to about 300 µL/min, about 10 µL/min to about 350 µL/min, about 10 µL/min to about 400 µL/min, or about 10 µL/min to about 450 µL/min.

As can readily be appreciated, any perfusion system, including but not limited to peristalsis systems and gravity feeds, appropriate to a given classification and/or sorting system can be utilized.

As noted above, the flow cell 105 can be implemented as a fluidic device that focuses cells from the sample into a single streamline that is imaged continuously. In the illustrated embodiment, the cell line is illuminated by a light source 106 (e.g., a lamp, such as an arc lamp) and an optical system 110 that directs light onto an imaging region 138 of the flow cell 105. An objective lens system 112 magnifies the cells by directing light toward the sensor of a high-speed camera system 114.

In some embodiments, a 10×, 20×, 40×, 60×, 80×, 100×, or 200× objective is used to magnify the cells. In some embodiments, a 10×, objective is used to magnify the cells. In some embodiments, a 20× objective is used to magnify the cells. In some embodiments, a 40× objective is used to magnify the cells. In some embodiments, a 60× objective is used to magnify the cells. In some embodiments, a 80× objective is used to magnify the cells. In some embodiments, a 100× objective is used to magnify the cells. In some embodiments, a 200× objective is used to magnify the cells. In some embodiments, a 10× to a 200× objective is used to magnify the cells, for example a 10×-20×, a 10×-40×, a 10×-60×, a 10×-80×, or a 10×-100× objective is used to magnify the cells.

As can readily be appreciated by a person having ordinary skill in the art, the specific magnification utilized can vary greatly and is largely dependent upon the requirements of a given imaging system and cell types of interest.

In some embodiments, one or more imaging devices may be used to capture images of the cell. In some aspects, the imaging device is a high-speed camera. In some aspects, the imaging device is a high-speed camera with a micro-second exposure time. In some instances, the exposure time is 1 millisecond. In some instances, the exposure time is between 1 millisecond (ms) and 0.75 millisecond. In some instances, the exposure time is between 1 ms and 0.50 ms. In some instances, the exposure time is between 1 ms and 0.25 ms. In some instances, the exposure time is between 0.75 ms and 0.50 ms. In some instances, the exposure time is between 0.75 ms and 0.25 ms. In some instances, the exposure time is between 0.50 ms and 0.25 ms. In some instances, the exposure time is between 0.25 ms and 0.1 ms. In some instances, the exposure time is between 0.1 ms and 0.01 ms. In some instances, the exposure time is between 0.1 ms and 0.001 ms. In some instances, the exposure time is between 0.1 ms and 1 microsecond (µs). In some aspects, the exposure time is between 1 µs and 0.1 µs. In some aspects, the exposure time is between 1 µs and 0.01 µs. In some aspects, the exposure time is between 0.1 µs and 0.01 µs. In some aspects, the exposure time is between 1 µs and 0.001 µs. In some aspects, the exposure time is between 0.1 µs and 0.001 µs. In some aspects, the exposure time is between 0.01 µs and 0.001 µs.

In some cases, the flow cell 105 may comprise at least 1, 2, 3, 4, 5, 6, 7, 8, 9, 10, or more imaging devices (e.g., the high-speed camera system 114) on or adjacent to the imaging region 138. In some cases, the flow cell may comprise at most 10, 9, 8, 7, 6, 5, 4, 3, 2, or 1 imaging device on or adjacent to the imaging region 138. In some cases, the flow cell 105 may comprise a plurality of imaging devices. Each of the plurality of imaging devices may use light from a same light source. Alternatively, each of the plurality of imaging devices may use light from different light sources. The plurality of imaging devices may be configured in parallel and/or in series with respect to one another. The plurality of imaging devices may be configured on one or more sides (e.g., two adjacent sides or two opposite sides) of the flow cell 105. The plurality of imaging devices may be configured to view the imaging region 138 along a same axis or different axes with respect to (i) a length of the flow cell 105 (e.g., a length of a straight channel of the flow cell 105) or (ii) a direction of migration of one or more particles (e.g., one or more cells) in the flow cell 105.

One or more imaging devices of the present disclosure may be stationary while imaging one or more cells, e.g., at the imaging region 138. Alternatively, one or more imaging devices may move with respect to the flow channel (e.g., along the length of the flow channel, towards and/or away from the flow channel, tangentially about the circumference of the flow channel, etc.) while imaging the one or more cells. In some examples, the one or more imaging devices may be operatively coupled to one or more actuators, such as, for example, a stepper actuator, linear actuator, hydraulic actuator, pneumatic actuator, electric actuator, magnetic actuator, and mechanical actuator (e.g., rack and pinion, chains, etc.).

In some cases, the flow cell 105 may comprise at least 1, 2, 3, 4, 5, 6, 7, 8, 9, 10, or more imaging regions (e.g., the imaging region 138). In some cases, the flow cell 105 may comprise at most 10, 9, 8, 7, 6, 5, 4, 3, 2, or 1 imaging region. In some examples, the flow cell 105 may comprise a plurality of imaging regions, and the plurality of imaging regions may be configured in parallel and/or in series with respect to each another. The plurality of imaging regions may or may not be in fluid communication with each other. In an example, a first imaging region and a second imaging region may be configured in parallel, such that a first fluid that passes through the first imaging region does not pass through a second imaging region. In another example, a first imaging region and a second imaging region may be configured in series, such that a first fluid that passes through the first imaging region also passes through the second imaging region.

In some embodiments, image sequences from cells are recorded at rates of about 10 frames/sec to about 10,000,000 frames/sec. In some embodiments, image sequences from cells are recorded at rates of at least about 10 frames/sec. In some embodiments, image sequences from cells are recorded at rates of at most about 10,000,000 frames/sec. In some embodiments, image sequences from cells are recorded at rates of about 10 frames/sec to about 100 frames/sec, about 10 frames/sec to about 1,000 frames/sec, about 10 frames/sec to about 10,000 frames/sec, about 10 frames/sec to about 100,000 frames/sec, about 10 frames/sec to about 1,000,000 frames/sec, about 10 frames/sec to about 10,000,000 frames/sec, about 100 frames/sec to about 1,000 frames/sec, about 100 frames/sec to about 10,000 frames/sec, about 100 frames/sec to about 100,000 frames/sec, about 100 frames/sec to about 1,000,000 frames/sec, about 100 frames/sec to about 10,000,000 frames/sec, about 1,000 frames/sec to about 10,000 frames/sec, about 1,000 frames/sec to about 100,000 frames/sec, about 1,000 frames/sec to about 1,000,000 frames/sec, about 1,000 frames/sec to about 10,000,000 frames/sec, about 10,000 frames/sec to about 100,000 frames/sec, about 10,000 frames/sec to about 1,000,000 frames/sec, about 10,000 frames/sec to about 10,000,000 frames/sec, about 100,000 frames/sec to about 1,000,000 frames/sec, about 100,000 frames/sec to about 10,000,000 frames/sec, or about 1,000,000 frames/sec to about 10,000,000 frames/sec. In some embodiments, image sequences from cells are recorded at rates of about 10 frames/sec, about 100 frames/sec, about 1,000 frames/sec, about 10,000 frames/sec, about 100,000 frames/sec, about 1,000,000 frames/sec, or about 10,000,000 frames/sec.

In some embodiments, image sequences from cells are recorded at rates of between 10,000-10,000,000 frames/sec using a high-speed camera, which may be color, monochrome, and/or imaged using any of a variety of imaging modalities including (but not limited to) the near-infrared spectrum. In some embodiments, image sequences from cells are recorded at rates of between 50,000-5,000,000 frames/sec. In some embodiments, image sequences from cells are recorded at rates of between 50,000-100,000 frames/sec. In some embodiments, image sequences from cells are recorded at rates of between 100,000-1,000,000 frames/sec. In some embodiments, image sequences from cells are recorded at rates of between 100,000-500,000 frames/sec. In some embodiments, image sequences from cells are recorded at rates of between 500,000-1,000,000 frames/sec. In some embodiments, image sequences from cells are recorded at rates of between 1,000,000-5,000,000 frames/sec.

In some embodiments, image sequences from cells are recorded at a rate of about 50,000 frames/sec, about 100,000 frames/sec, about 200,000 frames/sec, about 300,000 frames/sec, about 400,000 frames/sec, about 500,000 frames/sec, about 750,000 frames/sec, about 1,000,000 frames/sec, about 2,500,000 frames/sec, about 5,000,000 frames/sec, or about 10,000,000 frames/sec.

In some embodiments, the imaging device used in the present disclosure is an ultra-high speed camera, wherein images are recorded at a rate of up to 25,000,000 frames/sec. In some instances, the ultra-high speed camera runs at 20,000 revolutions per second. In some instances, the high-speed camera has a resolution of 616×920 pixels.

The imaging device(s) (e.g., the high-speed camera) of the imaging system can comprise an electromagnetic radiation sensor (e.g., IR sensor, color sensor, etc.) that detects at least a portion of the electromagnetic radiation that is reflected by and/or transmitted from the flow cell or any content (e.g., the cell) in the flow cell. The imaging device can be in operative communication with one or more sources (e.g., at least 1, 2, 3, 4, 5, or more) of the electromagnetic radiation. The electromagnetic radiation can comprise one or more wavelengths from the electromagnetic spectrum including, but not limited to x-rays (about 0.1 nanometers (nm) to about 10.0 nm; or about $10^{18}$ Hertz (Hz) to about $10^{16}$ Hz), ultraviolet (UV) rays (about 10.0 nm to about 380 nm; or about $8\times10^{16}$ Hz to about $10^{15}$ Hz), visible light (about 380 nm to about 750 nm; or about $8\times10^{14}$ Hz to about $4\times10^{14}$ Hz), infrared (IR) light (about 750 nm to about 0.1 centimeters (cm); or about $4\times10^{14}$ Hz to about $5\times10^{11}$ Hz), and microwaves (about 0.1 cm to about 100 cm; or about $10^8$ Hz to about $5\times10^{11}$ Hz). In some cases, the source(s) of the electromagnetic radiation can be ambient light, and thus the cell sorting system may not have an additional source of the electromagnetic radiation.

The imaging device(s) can be configured to take a two-dimensional image (e.g., one or more pixels) of the cell and/or a three-dimensional image (e.g., one or more voxels) of the cell.

In some embodiment, the imaging area is illuminated with a high-power light-emitting diode (LED) with exposure times that is less than 1 millisecond (msec) to help prevent motion blurring of cells. In some embodiment, the imaging area is illuminated with a high-power LED with exposure times that is less than 1 microsecond (μsec) to help prevent motion blurring of cells. In some embodiments the imaging device comprises a combination of a strobe light and a camera. Strobe light, strobe, stroboscopic lamp, and strobing light may be used interchangeably. In some instances, a strobe light is a device used to produce regular flashes of light. In some embodiments, a high-speed strobe light is used in combination with one or more cameras. In some instances, the high-speed strobe lights are capable of up to 2500 strobes per second. In some instances, the high-speed strobe lights are capable of up to 5000 strobes per second. In some instances, the high-speed strobe lights have a storage of electrical energy to pulse the LEDs wherein the energy can go up to 2000 watts when the LEDs are active. In some instances, the high-speed strobe light pulses the LED with up to 180 amps of DC current. In some instances, the strobe light is white. In some instances, the strobe light is blue with a wavelength of 470 nm. In some instances, the strobe light is green with a wavelength of 530 nm. In some instances, the strobe light is red with a wavelength of 625 nm. In some instances, the strobe light is infrared with a wavelength of 850 nm. In some embodiments, the imaging device comprises a combination of a strobe light and one or more cameras wherein the cameras are high-speed camera. In some embodiments, the imaging device comprises a combination of a high-speed strobe light and one or more cameras, wherein the cameras are high-speed cameras.

As can readily be appreciated, the exposure times can differ across different systems and can largely be dependent upon the requirements of a given application or the limitations of a given system such as but not limited to flow rates. Images are acquired and can be analyzed using an image analysis algorithm.

In some embodiments, the images are acquired and analyzed post-capture. In some aspects, the images are acquired and analyzed in real-time continuously. Using object tracking software, single cells can be detected and tracked while in the field of view of the camera. Background subtraction can then be performed. In a number of embodiments, the flow cell 106 causes the cells to rotate as they are imaged and multiple images of each cell are provided to a computing system 116 for analysis. In some embodiments, the multiple images comprise images from a plurality of cell angles.

The term "real time" or "real-time," as used interchangeably herein, generally refers to an event (e.g., an operation, a process, a method, a technique, a computation, a calculation, an analysis, an optimization, etc.) that is performed using recently obtained (e.g., collected or received) data. Examples of the event may include, but are not limited to, analysis of a one or more images of a cell to classify the cell, updating one or more deep learning algorithms (e.g., neural networks) for classification and sorting, controlling actuation of one or more valves by at a sorting bifurcation, etc. In some cases, a real time event may be performed almost immediately or within a short enough time span, such as within at least 0.0001 ms, 0.0005 ms, 0.001 ms, 0.005 ms, 0.01 ms, 0.05 ms, 0.1 ms, 0.5 ms, 1 ms, 5 ms, 0.01 seconds, 0.05 seconds, 0.1 seconds, 0.5 seconds, 1 second, or more. In some cases, a real time event may be performed almost immediately or within a short enough time span, such as within at most 1 second, 0.5 seconds, 0.1 seconds, 0.05 seconds, 0.01 seconds, 5 ms, 1 ms, 0.5 ms, 0.1 ms, 0.05 ms, 0.01 ms, 0.005 ms, 0.001 ms, 0.0005 ms, 0.0001 ms, or less.

The flow rate and channel dimensions can be determined to obtain multiple images of the same cell from a plurality of different angles (i.e., a plurality of cell angles). A degree of rotation between an angle to the next angle may be uniform or non-uniform. In some examples, a full 360° view of the cell is captured. In some embodiments, 4 images are provided in which the cell rotates 90° between successive frames. In some embodiments, 8 images are provided in which the cell rotates 45° between successive frames. In some embodiments, 24 images are provided in which the cell rotates 15° between successive frames. In some embodiments, at least three or more images are provided in which the cell rotates at a first angle between a first frame and a second frame, and the cell rotates at a second angle between the second frame and a third frame, wherein the first and second angles are different. In some examples, less than the full 360° view of the cell may be captured, and a resulting plurality of images of the same cell may be sufficient to classify the cell (e.g., determine a specific type of the cell).

The cell can have a plurality of sides. The plurality of sides of the cell can be defined with respect to a direction of the transport (flow) of the cell through the channel. In some cases, the cell can comprise a stop side, a bottom side that is opposite the top side, a front side (e.g., the side towards the direction of the flow of the cell), a rear side opposite the front side, a left side, and/or a right side opposite the left side. In some cases, the image of the cell can comprise a plurality of images captured from the plurality of angles, wherein the plurality of images comprise: (1) an image captured from the top side of the cell, (2) an image captured from the bottom side of the cell, (3) an image captured from the front side of the cell, (4) an image captured from the rear side of the cell, (5) an image captured from the left side of the cell, and/or (6) an image captured from the right side of the cell.

In some embodiments, a two-dimensional "hologram" of a cell can be generated by superimposing the multiple images of the individual cell. The "hologram" can be analyzed to automatically classify characteristics of the cell based upon features including but not limited to the morphological features of the cell.

In some embodiments, 1, 2, 3, 4, 5, 6, 7, 8, 9, or 10 images are captured for each cell. In some embodiments, 5 or more images are captured for each cell. In some embodiments, from 5 to 10 images are captured for each cell. In some embodiments, 10 or more images are captured for each cell. In some embodiments, from 10 to 20 images are captured for each cell. In some embodiments, 20 or more images are captured for each cell. In some embodiments, from 20 to 50 images are captured for each cell. In some embodiments, 50 or more images are captured for each cell. In some embodiments, from 50 to 100 images are captured for each cell. In some embodiments, 100 or more images are captured for each cell. In some cases, at least 1, 2, 3, 4, 5, 6, 7, 8, 9, 10, 15, 20, 30, 40, 50, or more images may be captured for each cell at a plurality of different angles. In some cases, at most 50, 40, 30, 20, 15, 10, 9, 8, 7, 6, 5, 4, 3, or 2 images may be captured for each cell at a plurality of different angles.

In some embodiments, the imaging device is moved so as to capture multiple images of the cell from a plurality of angles. In some aspects, the images are captured at an angle between 0 and 90 degrees to the horizontal axis. In some aspects, the images are captured at an angle between 90 and 180 degrees to the horizontal axis. In some aspects, the images are captured at an angle between 180 and 270 degrees to the horizontal axis. In some aspects, the images are captured at an angle between 270 and 360 degrees to the horizontal axis.

In some embodiments, multiple imaging devices (for e.g. multiple cameras) are used wherein each device captures an image of the cell from a specific cell angle. In some aspects, 2, 3, 4, 5, 6, 7, 8, 9, or 10 cameras are used. In some aspects, more than 10 cameras are used, wherein each camera images the cell from a specific cell angle.

As can readily be appreciated, the number of images that are captured is dependent upon the requirements of a given application or the limitations of a given system. In several embodiments, the flow cell has different regions to focus, order, and/or rotate cells. Although the focusing regions, ordering regions, and cell rotating regions are discussed as affecting the sample in a specific sequence, a person having ordinary skill in the art would appreciate that the various regions can be arranged differently, where the focusing, ordering, and/or rotating of the cells in the sample can be performed in any order. Regions within a microfluidic device implemented in accordance with an embodiment of the disclosure are illustrated in FIG. 1B. Flow cell 105 may include a filtration region 130 to prevent channel clogging by aggregates/debris or dust particles. Cells pass through a focusing region 132 that focuses the cells into a single streamline of cells that are then spaced by an ordering region 134. In some embodiments, the focusing region utilizes "inertial focusing" to form the single streamline of cells. In some embodiments, the focusing region utilizes 'hydrodynamic focusing" to focus the cells into the single streamline of cells. Optionally, prior to imaging, rotation can be imparted upon the cells by a rotation region 136. The optionally spinning cells can then pass through an imaging region 138 in which the cells are illuminated for imaging prior to exiting the flow cell. These various regions are described and discussed in further detail below. In some cases, the rotation region 136 may precede the imaging region 138. In some cases, the rotation region 136 may be a part (e.g., a beginning portion, a middle portion, and/or an end portion with respect to a migration of a cell within the flow cell) of the imaging region 138. In some cases, the imaging region 138 may be a part of the rotation region 136.

In some embodiments, a single cell is imaged in a field of view of the imaging device, e.g. camera. In some embodiments, multiple cells are imaged in the same field of view of the imaging device. In some aspects, 1, 2, 3, 4, 5, 6, 7, 8, 9, or 10 cells are imaged in the same field of view of the imaging device. In some aspects, up to 100 cells are imaged in the same field of view of the imaging device. In some instances, 10 to 100 cells are imaged in the field of view, for example, 10 to 20 cells, 10 to 30 cells, 10 to 40 cells, 10 to 50 cells, 10 to 60 cells, 10 to 80 cells, 10 to 90 cells, 20 to 30 cells, 20 to 40 cells, 20 to 50 cells, 20 to 60 cells, 20 to 70 cells, 20 to 80 cells, 20 to 90 cells, 30 to 40 cells, 40 to 50 cells, 40 to 60 cells, 40 to 70 cells, 40 to 80 cells, 40 to 90 cells, 50 to 60 cells, 50 to 70 cells, 50 to 80 cells, 50 to 90 cells, 60 to 70 cells, 60 to 80 cells, 60 to 90 cells, 70 to 80 cells, 70 to 90 cells, 90 to 100 cells are imaged in the same field of view of the imaging device.

In some cases, only a single cell may be allowed to be transported across a cross-section of the flow channel perpendicular to the axis of the flow channel. In some cases, a plurality of cells (e.g., at least 2, 3, 4, 5, or more cells; at most 5, 4, 3, 2, or 1 cell) may be allowed to be transported simultaneously across the cross-section of the flow channel perpendicular to the axis of the flow channel. In such a case, the imaging device (or the processor operatively linked to the imaging device) may be configured to track each of the plurality of cells as they are transported along the flow channel.

In some embodiments, the classification and/or sorting systems in accordance with various embodiments of the disclosure eliminate the variability involved in manual preparation of slides, which rely on expertise of the operator. Furthermore, image segmentation can be avoided. The classification and/or sorting system allows for high flow rates and high-throughputs can be achieved.

In some embodiments, the classification and/or sorting system includes an imaging system that can capture images at a rate of at least 100 cells/second and a computing system that can classify at a rate of at least 100 cells/second. In some embodiments, the classification and/or sorting system includes an imaging system that can capture images at a rate of at least 500 cells/second and a computing system that can classify at a rate of at least 500 cells/second. In some embodiments, the classification and/or sorting system includes an imaging system that can capture images at a rate of at least 1000 cells/second and a computing system that can classify at a rate of at least 1000 cells/second. In some embodiments, the classification and/or sorting system includes an imaging system that can capture images at a rate of at least 2000 cells/second and a computing system that can classify at a rate of at least 2000 cells/second. In some embodiments, the classification and/or sorting system includes an imaging system that can capture images at a rate of at least 5000 cells/second and a computing system that can classify at a rate of at least 5000 cells/second. In some embodiments, the classification and/or sorting system includes an imaging system that can capture images at a rate of at least 10,000 cells/second and a computing system that can classify at a rate of at least 10,000 cells/second.

In some embodiments, the classification and/or sorting system includes an imaging system that can capture images at a rate that is equal up to 100 cells/second and a computing system that can classify up to 100 cells/second. In some embodiments, the classification and/or sorting system includes an imaging system that can capture images at a rate that is equal up to 500 cells/second and a computing system that can classify up to 500 cells/second. In some embodiments, the classification and/or sorting system includes an imaging system that can capture images at a rate that is equal to up to 1000 cells/second and a computing system that can classify up to 1000 cells/second. In some embodiments, the classification and/or sorting system includes an imaging system that can capture images at a rate that is equal to up to 2000 cells/second and a computing system that can classify up to 2000 cells/second. In some embodiments, the classification and/or sorting system includes an imaging system that can capture images at a rate that is equal to up to 5000 cells/second and a computing system that can classify up to 5000 cells/second. In some embodiments, the classification and/or sorting system includes an imaging system that can capture images at a rate that is equal to up to 10,000 cells/second and a computing system that can classify up to 10,000 cells/second.

The imaging system can include, among other things, a camera, an objective lens system and a light source. In a number of embodiments, flow cells similar to those described above can be fabricated using standard 2D microfluidic fabrication techniques, requiring minimal fabrication time and cost.

Although specific classification and/or sorting systems, flow cells, and microfluidic devices are described above with respect to FIGS. 1A and 1B, classification and/or sorting systems can be implemented in any of a variety of ways appropriate to the requirements of specific applications in accordance with various embodiments of the disclosure. Specific elements of microfluidic devices that can be utilized in classification and/or sorting systems in accordance with some embodiments of the disclosure are discussed further below.

Microfluidic Device Fabrication

Microfluidic devices in accordance with several embodiments of the disclosure can be fabricated using a variety of methods. In some embodiments, a combination of photolithography and mold casting is used to fabricate a microfluidic device. Conventional photolithography typically involves the use of photoresist and patterned light to create a mold containing a positive relief of the desired microfluidic pattern on top of a substrate, typically a silicon wafer. Photoresist is a photo-curable material that can be used in photolithography to create structures with feature sizes on the order of micrometers (μm). During fabrication, the photoresist can be deposited onto a substrate. The substrate can be spun to create a layer of photoresist with a targeted desired height. The photoresist layer can then be exposed to light, typically UV light (depending on the type of photoresist), through a patterned mask to create a cured pattern of photoresist. The remaining uncured portions can be developed away, leaving behind a positive relief mold that can be used to fabricate microfluidic devices.

From the mold, material can be cast to create a layer containing a negative relief pattern. Inlet and outlet holes can be formed at appropriate regions, and the device can then be bonded to a backing to create a flow-through device, or flow cell, with flow channels (e.g., microfluidic channels). A cross-section of the flow channel can have a width and a height. The cross-section may be perpendicular to an axis of the flow channel (e.g., a direction of the flow of the solvent with or without cells inside the flow channel). The width and the height of the flow channel can be perpendicular to each other. The width and/or the height of the flow channel can be uniform or non-uniform along the axis of the flow channel. In some cases, the width or the height of the flow channel can increase or decrease (e.g., gradually or rapidly) along a direction of the flow channel through which the cell is transported. In some cases, the width or the height of the flow channel can increase along a section of the flow channel, and decrease along a different section of the flow channel.

The width or the height of the cross-section of the flow channel can be about 1 μm to about 500 μm. The width or the height of the cross-section of the flow channel can be at least about 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 200 μm, 300 μm, 400 μm, 500 μm, or more. The width or the height of the cross-section of the flow channel can be at most about 500 µm, 400 µm, 300 µm, 200 µm, 100 µm, 90 µm, 0 µm, 0 µm, 60 µm, 50 µm, 40 µm, 30 µm, 20 µm, 10 µm, 9 µm, 8 µm, 7 µm, 6 µm, 5 µm, 4 µm, 3 µm, 2 µm, 1 µm, or less.

The width or the height of the channel can increase or decrease along the direction of the flow channel at about 0.01 percent per µm (%/µm) to about 1000%/µm. The increase of decrease of the width or height of the channel along the direction of the flow channel can be at least about 0.01%/µm, 0.05%/µm, 0.1%/µm, 0.5%/µm, 1%/µm, 5%/µm, 10%/µm, 50%/µm, 100%/µm, 500%/µm, 1000%/µm, or more. The increase of decrease of the width or height of the channel along the direction of the flow channel can be at most about 1000%/µm, 500%/µm, 100%/µm, 50%/µm, 10%/µm, 5%/µm, 1%/µm, 0.5%/µm, 0.1%/µm, 0.05%/µm, 0.01%/µm, or less.

One or more flow channels of the flow cell of the present disclosure may have various shapes and sizes. For example, at least a portion of the flow channel (e.g., the focusing region 132, the ordering region 134, the rotation region 136, the imaging region 138, connecting region therebetween, etc.) may have a cross-section that is circular, triangular, square, rectangular, pentagonal, hexagonal, or any partial shape or combination of shapes thereof.

In some embodiments, the system of the present disclosure comprises straight channels with rectangular or square cross-sections. In some aspects, the system of the present disclosure comprises straight channels with round cross-sections. In some aspects, the system comprises straight channels with half-ellipsoid cross-sections. In some aspects, the system comprises spiral channels. In some aspects, the system comprises round channels with rectangular cross-sections. In some aspects, the system comprises round channels with rectangular channels with round cross-sections. In some aspects, the system comprises round channels with half-ellipsoid cross-sections. In some aspects, the system comprises channels that are expanding and contracting in width with rectangular cross-sections. In some aspects, the system comprises channels that are expanding and contracting in width with round cross-sections. In some aspects, the system comprises channels that are expanding and contracting in width with half-ellipsoid cross-sections.

In some embodiments utilizing a rotation section, a two-layer fabrication process can be used to orient the rotation section so that imaging of the cells as they rotate will provide images of cells at different angles with a more accurate representation of cellular features.

As can be readily appreciated, the microfluidic device can be fabricated using a variety of materials as appropriate to the requirements of the given application. In imaging applications, the microfluidic device is typically made of an optically transparent material such as (but not limited to) polydimethylsiloxane (PDMS). In some embodiments, the microfluidic device is made of silicon. In some embodiments, the microfluidic device is made of low-temperature cofired ceramic (LTCC). In some embodiments, the microfluidic device is made of thermoset polyester (TPE). In some embodiments, the microfluidic device is made of polystyrene (PS). In some embodiments, the microfluidic device is made of polycarbonate (PC). In some embodiments, the microfluidic device is made of poly-methyl methacrylate (PMMA). In some embodiments, the microfluidic device is made of poly(ethylene glycol) diacrylate (PEGDA). In some embodiments, the microfluidic device is made of polyfluoropolyether diol methacrylate (PFPE-DMA). In some embodiments, the microfluidic device is made of polyurethane (PU).

Although a specific method of microfluidic device fabrication is discussed, any of a variety of methods can be implemented to fabricate a microfluidic device utilized in accordance with various embodiments of the disclosure as appropriate to the requirements of a given application.

Microfluidic Filters

Microfluidic devices in accordance with several embodiments of the disclosure can include one or more microfluidic filters at the inlets, or further down, of the microfluidic device to prevent channel clogging. In other embodiments, filtration can occur off device. The specific dimensions and patterns of the filters and the microfluidic channel can vary and are largely dependent upon the sizes of the cells of interest and the requirements of a given application. Any of a variety of microfluidic filter systems can be implemented on microfluidic devices utilized in accordance with various embodiments of the disclosure as appropriate to the requirements of a given flow application.

Focusing Regions

The flow channel can comprise one or more walls that are formed to focus one or more cells into a streamline. The flow channel can comprise a focusing region comprising the wall(s) to focus the cell(s) into the streamline. Focusing regions on a microfluidic device can take a disorderly stream of cells and utilize a variety of forces (for e.g. inertial lift forces (wall effect and shear gradient forces) or hydrodynamic forces) to focus the cells within the flow into a streamline of cells. In some embodiments, the cells are focused in a single streamline. In some examples, the cells are focused in multiple streamlines, for example at least 2, at least 3, at least 4, at least 5, at least 6, at least 7, at least 8, at least 9, or at least 10 streamlines.

The focusing region receives a flow of randomly arranged cells via an upstream section. The cells flow into a region of contracted and expanded sections in which the randomly arranged cells are focused into a single streamline of cells. The focusing is driven by the action of inertial lift forces (wall effect and shear gradient forces) acting on cells at Reynolds numbers>1, where channel Reynolds number is defined as follows: $Re_c = \rho U_m W/\mu$, where $U_m$ is the maximum fluid velocity, $\rho$ is the fluid density, $\mu$ is the fluid viscosity, and W is the channel dimension. In some embodiments, Reynolds numbers around 20-30 can be used to focus particles from about 10 µm to about 20 In some embodiments, the Reynolds number is such that laminar flow occurs within the microfluidic channels. As can readily be appreciated, the specific channel Reynolds number can vary and is largely determined by the characteristics of the cells for which the microfluidic device is designed, the dimensions of the microfluidic channels, and the flow rate controlled by the perfusion system. The Reynolds number of the flow channel of the present disclosure may or may not depend on one or more dimensional parameters (e.g., radius, diameter, cross-sectional area, volume, etc.) of a particle (e.g., a cell) flowing through the flow channel.

In some embodiments, the focusing region is formed with curvilinear walls that form periodic patterns. In some embodiments, the patterns form a series of square expansions and contractions. In other embodiments, the patterns are sinusoidal. In further embodiments, the sinusoidal patterns are skewed to form an asymmetric pattern. The focusing region can be effective in focusing cells over a wide range of flow rates. In the illustrated embodiment, an asymmetrical sinusoidal-like structure is used as opposed to square expansions and contractions. This helps prevent the formation of secondary vortices and secondary flows behind the particle flow stream. In this way, the illustrated structure allows for faster and more accurate focusing of cells to a single lateral equilibrium position. Spiral and curved channels can also be used in an inertia regime; however, these can complicate the integration with other modules. Finally, straight channels where channel width is greater than channel height can also be used for focusing cells onto single lateral position. However, in this case, since there will be more than one equilibrium position in the z-plane, imaging can become problematic, as the imaging focal plane is preferably fixed. As can readily be appreciated, any of a variety of structures that provide a cross section that expands and contracts along the length of the microfluidic channel or are capable of focusing the cells can be utilized as appropriate to the requirements of specific applications.

The cell sorting system can be configured to focus the cell at a width and/or a height within the flow channel along an axis of the flow channel. The cell can be focused to a center or off the center of the cross-section of the flow channel. The cell can be focused to a side (e.g., a wall) of the cross-section of the flow channel. A focused position of the cell within the cross-section of the channel may be uniform or non-uniform as the cell is transported through the channel.

While specific implementations of focusing regions within microfluidic channels are described above, any of a variety of channel configurations that focus cells into a single streamline can be utilized as appropriate to the requirements of a specific application in accordance with various embodiments of the disclosure.

Ordering Regions

Microfluidic channels can be designed to impose ordering upon a single streamline of cells formed by a focusing region in accordance with several embodiments of the disclosure. Microfluidic channels in accordance with some embodiments of the disclosure include an ordering region having pinching regions and curved channels. The ordering region orders the cells and distances single cells from each other to facilitate imaging. In some embodiments, ordering is achieved by forming the microfluidic channel to apply inertial lift forces and Dean drag forces on the cells. Dean flow is the rotational flow caused by fluid inertia. The microfluidic channel can be formed to create secondary flows that apply a Dean drag force proportional to the velocity of the secondary flows. Dean drag force scales with about $\rho U_m^2 \alpha D_h^2/R$, where $\rho$ is the fluid density, Um is the maximum fluid velocity, $D_h=2WH/(W+H)$ is the channel hydraulic diameter, $\alpha$ is the particle dimension, and R is the curvature radius. The force balance between inertial lift and Dean drag forces determines particle equilibrium position.

Depending on the particle size, the relative interior and exterior radii of curvature ($R_{1in,out}$) of the channel and channel height ($H_C$) of the microfluidic channel can be determined to reach equilibrium at desired locations. Different combinations of curved and pinching regions (and their parameters) can be used to achieve desired distance between particles. Channel width in the pinching region can be adjusted such that the cells will not be squeezed through the channels, causing possible damage to the cell membrane (the cells can, however, be slightly deformed without touching the channel walls while traveling through the pinching regions). Additionally, the squeezing could cause debris/residues from cell membrane left on the channel walls, which will change the properties of the channel. The ordering in the pinching regions is driven by instantaneous change in channel fluidic resistance upon arrival of a cell/particle. Since the channel width in this region is close to cell/particle dimensions, when a cell arrives at the pinching region, the channel resistance increases. Since the whole system is pressure-regulated (constant pressure), this can cause an instantaneous decrease in flow rate and therefore spacing of the cells. The length and width of pinching region can be adjusted to reach desired spacing between cells. The curved channel structure can also help with focusing cells to a single z position, facilitating imaging.

Different geometries, orders, and/or combinations can be used. In some embodiments, pinching regions can be placed downstream from the focusing channels without the use of curved channels. Adding the curved channels helps with more rapid and controlled ordering, as well as increasing the likelihood that particles follow a single lateral position as they migrate downstream. As can readily be appreciated, the specific configuration of an ordering region is largely determined based upon the requirements of a given application.

Cell Rotating Regions and Imaging Regions

Architecture of the microfluidic channels of the flow cell of the present disclosure may be controlled (e.g., modified, optimized, etc.) to modulate cell flow along the microfluidic channels. Examples of the cell flow may include (i) cell focusing (e.g., into a single streamline) and (ii) rotation of the one or more cells as the cell(s) are migrating (e.g., within the single streamline) down the length of the microfluidic channels. In some embodiments, microfluidic channels can be configured to impart rotation on ordered cells in accordance with a number of embodiments of the disclosure. One or more cell rotation regions (e.g., the cell rotation region 136) of microfluidic channels in accordance with some embodiments of the disclosure use co-flow of a particle-free buffer to induce cell rotation by using the co-flow to apply differential velocity gradients across the cells. In some cases, a cell rotation region may introduce co-flow of at least 1, 2, 3, 4, 5, or more buffers (e.g., particle-free, or containing one or more particles, such as polymeric or magnetic particles) to impart rotation on one or more cells within the channel. In some cases, a cell rotation region may introduce co-flow of at most 5, 4, 3, 2, or 1 buffer to impart the rotation of one or more cells within the channel. In some examples, the plurality of buffers may be co-flown at a same position along the length of the cell rotation region, or sequentially at different positions along the length of the cell rotation region. In some examples, the plurality of buffers may be the same or different. In several embodiments, the cell rotation region of the microfluidic channel is fabricated using a two-layer fabrication process so that the axis of rotation is perpendicular to the axis of cell downstream migration and parallel to cell lateral migration.

Cells may be imaged in at least a portion of the cell rotating region, while the cells are tumbling and/or rotating as they migrate downstream. Alternatively or in addition to, the cells may be imaged in an imaging region that is adjacent to or downstream of the cell rotating region. In some examples, the cells may be flowing in a single streamline within a flow channel, and the cells may be imaged as the cells are rotating within the single streamline. A rotational speed of the cells may be constant or varied along the length of the imaging region. This may allow for the imaging of a cell at different angles (e.g., from a plurality of images of the cell taken from a plurality of angles due to rotation of the cell), which may provide more accurate information concerning cellular features than can be captured in a single image or a sequence of images of a cell that is not rotating to any significant extent. This also allow a 3D reconstruction of the cell using available software since the angles of rotation across the images are known. Alternatively, every single image of the sequence of image many be analyzed individually to analyze (e.g., classify) the cell from each image. In some cases, results of the individual analysis of the sequence of images may be aggregated to determine a final decision (e.g., classification of the cell).

In some embodiments, a similar change in velocity gradient across the cell is achieved by providing a change in channel height (i.e., the dimension that is the smaller of the two dimensions of the cross section of the microfluidic channel and the dimension perpendicular to the imaging plane). This increase in channel height should be such that the width continues to be greater than the height of the channel. Also in the case of increasing channel height, there can be a shift in cell focusing position in the height dimension, which should be accounted for during imaging and adjustment of the imaging focal plane. In an example, the channel height may be increased by (i) changing a bottom surface of the channel (e.g., depressing the bottom surface of the channel) and/or (ii) changing a top surface of the channel (e.g., raising the top surface of the channel).

In some embodiments, a cell rotation region of a microfluidic channel incorporates an injected co-flow prior to an imaging region in accordance with an embodiment of the disclosure. Co-flow may be introduced in the z plane (perpendicular to the imaging plane) to spin the cells. Since the imaging is done in the x-y plane, rotation of cells around an axis parallel to the y-axis provides additional information by rotating portions of the cell that may have been occluded in previous images into view in each subsequent image. Due to a change in channel dimensions, at point xo, a velocity gradient is applied across the cells, which can cause the cells to spin. The angular velocity of the cells depends on channel and cell dimensions and the ratio between Q1 (main channel flow rate) and Q2 (co-flow flow rate) and can be configured as appropriate to the requirements of a given application. In some embodiments, a cell rotation region incorporates an increase in one dimension of the microfluidic channel to initiate a change in the velocity gradient across a cell to impart rotation onto the cell. In some aspects, a cell rotation region of a microfluidic channel incorporates an increase in the z-axis dimension of the cross section of the microfluidic channel prior to an imaging region in accordance with an embodiment of the disclosure. The change in channel height can initiate a change in velocity gradient across the cell in the z axis of the microfluidic channel, which can cause the cells to rotate as with using co-flow.

Although specific techniques for imparting velocity gradients upon cells are described above, any of a variety of techniques can be utilized to impart rotation on a single streamline of cells as appropriate to the requirements of specific applications in accordance with various embodiments of the disclosure.

Flowing Cells

In some embodiments, the system and methods of the present disclosure focuses the cells in microfluidic channels. The term focusing as used herein broadly means controlling the trajectory of cell/cells movement and comprises controlling the position and/or speed at which the cells travel within the microfluidic channels. In some embodiments controlling the lateral position and/or the speed at which the particles travel inside the microfluidic channels, allows to accurately predict the time of arrival of the cell at a bifurcation. The cells may then be accurately sorted. The parameters critical to the focusing of cells within the microfluidic channels include, but are not limited to channel geometry, particle size, overall system throughput, sample concentration, imaging throughput, size of field of view, and method of sorting.

Figure 5:
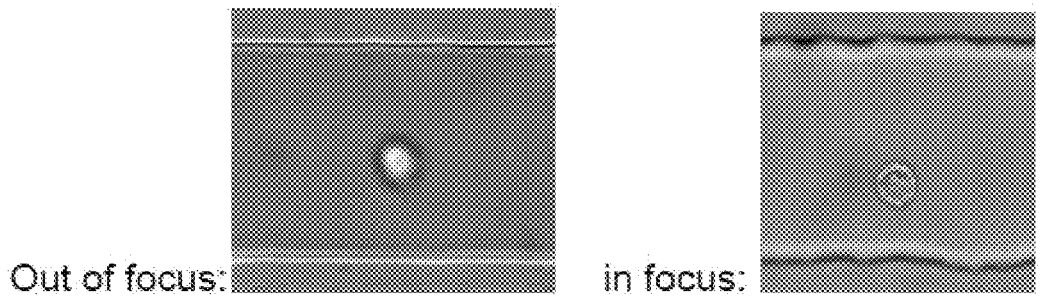
FIG. 5 conceptually illustrates an out-of-focus cell and an in-focus cell using inertia-based z focusing.

In some embodiments the focusing is achieved using inertial forces. In some embodiments, the system and methods of the present disclosure focus cells to a certain height from the bottom of the channel using inertial focusing (Dino Di Carlo, 2009, Lab on a Chip, which is incorporated herein by reference in its entirety). In these embodiments, the distance of the cells from the objective is equal and images of all the cells will be clear. As such, cellular details, such as nuclear shape, structure, and size appear clearly in the outputted images with minimal blur. In some aspects, the system disclosed herein has an imaging focusing plane that is adjustable. In some aspects, the focusing plane is adjusted by moving the objective or the stage. In some aspects, the best focusing plane is found by recording videos at different planes and the plane wherein the imaged cells have the highest Fourier magnitude, thus, the highest level of detail and highest resolution, is the best plane (FIG. 5).

Figure 6A:
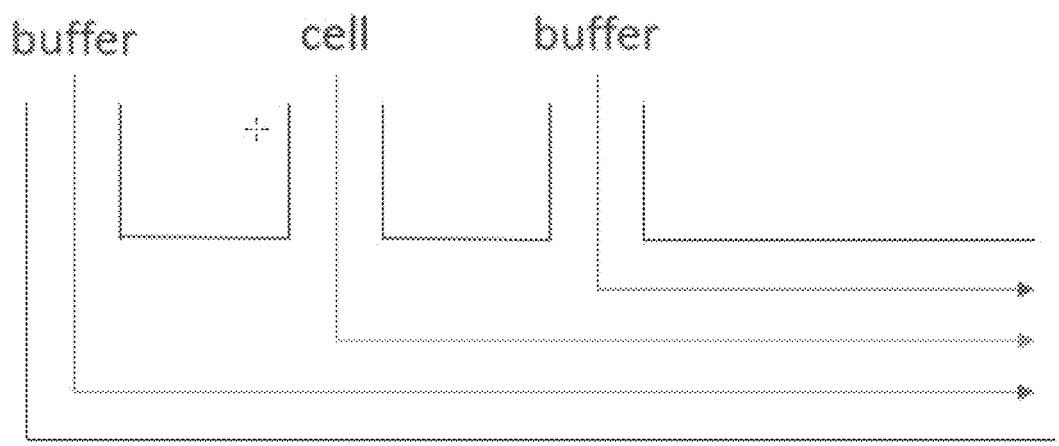
FIGS. 6A through 6D conceptually illustrate non-limiting examples of co-flow designs.

In some embodiments, the system and methods of the present disclosure utilize a hydrodynamic-based z focusing system to obtain a consistent z height for the cells of interests that are to be imaged. In some aspects, the design comprises hydrodynamic focusing using multiple inlets for main flow and side flow. In some aspects, the hydrodynamic-based z focusing system is a triple-punch design (FIG. 6A). In some aspects, the design comprises hydrodynamic focusing with three inlets, wherein the two side flows pinch cells at the center. For certain channel designs, dual z focus points may be created, wherein a double-punch design similar to the triple-punch design may be used to send objects to one of the two focus points to get consistent focused images. In some aspects, the design comprises hydrodynamic focusing with 2 inlets, wherein only one side flow channel is used and cells are focused near channel wall. In some aspects, the hydrodynamic focusing comprises side flows that do not contain any cells and a middle inlet that contains cells. The ratio of the flow rate on the side channel to the flow rate on the main channel determines the width of cell focusing region. In some aspects, the design is a combination of the above. In all aspects, the design is integrable with the bifurcation and sorting mechanisms disclosed herein. In some aspects, the hydrodynamic-based z focusing system is used in conjunction with inertia-based z focusing.

Figure 6B:
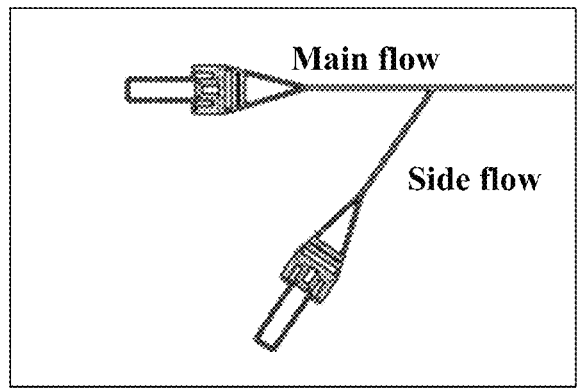
Figure 6C:
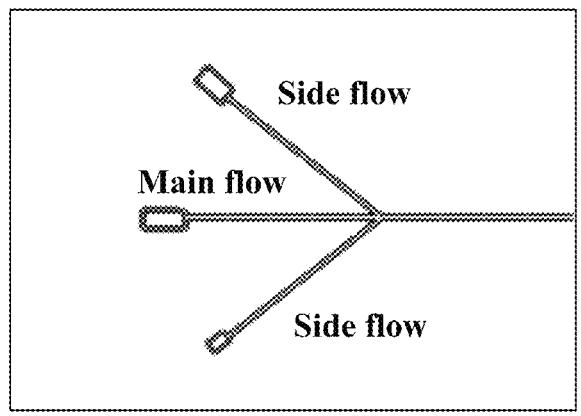
Figure 6D:
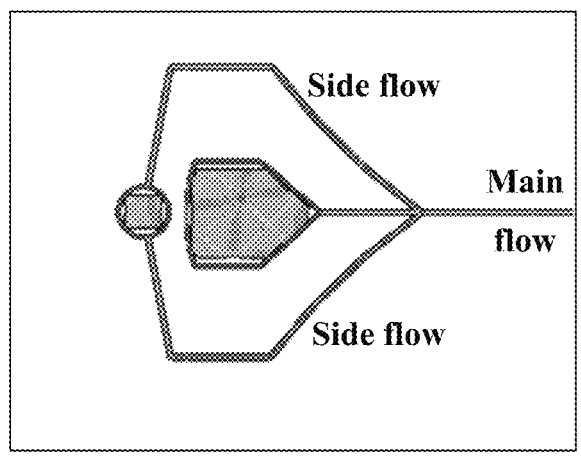

FIG. 6B illustrates an example of a single side-flow system for hydrodynamic focusing. A top inlet may direct flow of a solution with one or more particles across a main channel (going across the schematic from left to right), and a side inlet (beneath the top inlet) may direct a side flow to the main channel, thereby focusing the particle(s) near a wall of the main channel. FIGS. 6C and 6D illustrates examples of double side-flow system for hydrodynamic focusing. A main inlet (a large inlet with a pentagonal shape) may direct flow of a solution with one or more particles across a main channel (going across the schematic from left to right), and two side channels may each direct a side flow to the main channel, thereby focusing the particle(s) towards the center of the main channel. In some cases, the two side channels may be in fluid communication with two separate side inlets, as illustrated in FIG. 6C. In some cases, the two side channels may be in fluid communication with a single, shared inlet, as illustrated in FIG. 6D.

In some embodiments, the terms "particles", "objects", and "cells" are used interchangeably. In some aspects, the cell is a live cell. In some aspects, the cell is a fixed cell (e.g., in methanol or paraformaldehyde). In some cases, one or more cells may be coupled (e.g., attached covalently or non-covalently) to a substrate (e.g., a polymeric bead or a magnetic bead) while flowing through the flow cell. In some cases, the cell(s) may not be coupled to any substrate while flowing through the flow cell.

Method to Control Particle Arrival Times

Figure 2:
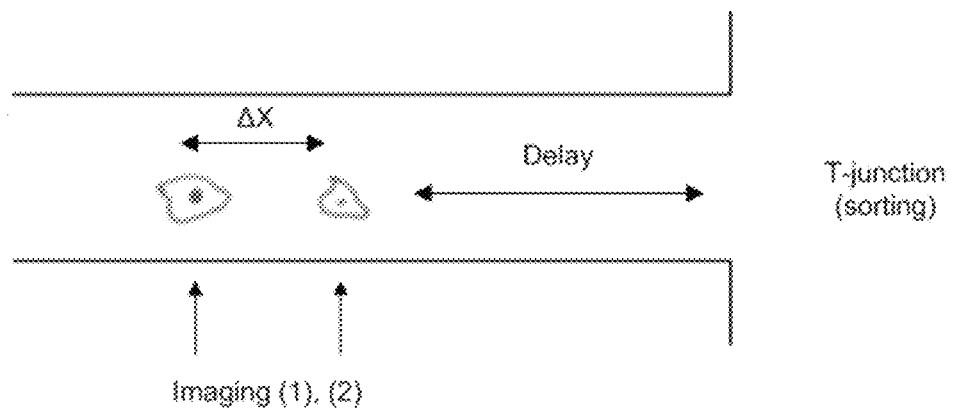
FIG. 2 conceptually illustrates an exemplary long flow channel with controlled length to ensure that the objects in the system arrive at the bifurcation exactly when the decision is made and valve actuation is completed.

In various embodiments, the systems and methods of the present disclosure sort the cells by ensuring that the cells in the system arrive at the bifurcation exactly when the decision is made and valve actuation is completed. In some aspects, ensuring that the objects arrive at the bifurcation exactly when (or prior to when) the decision is made and the valve actuation is completed is achieved by controlling length of the microfluidic channels. In some embodiments the channel is a long channel and the length of the channel is determined based on factors that include, but are not limited to, (i) the estimated time of decision making, (ii) latency and opening window of switching mechanism, such as valves, and (iii) velocity of the particles (FIG. 2).

Figure 3:
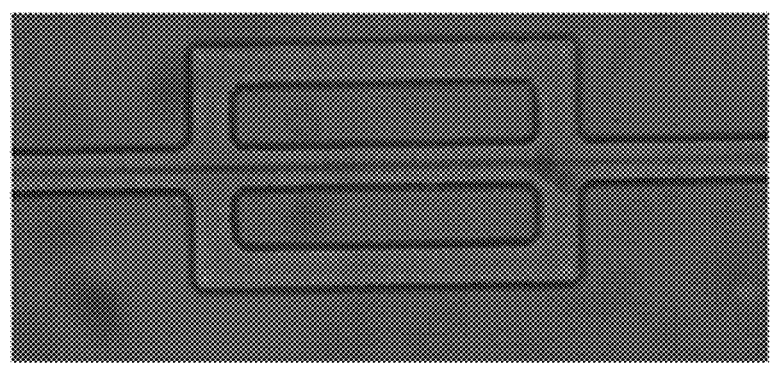
FIG. 3 conceptually illustrates an exemplary three-branch channel design.

In some embodiments, ensuring that the objects arrive at the bifurcation exactly when (or prior to when) the decision is made and the valve actuation is completed is achieved by controlling the velocity of the cells. Controlling the velocity of the cells may comprise increasing the velocity of the cells, decreasing the velocity of the cells, increasing acceleration of the cells, and/or decreasing acceleration of the cells. In some examples, this is achieved by branching the microfluidic channels. In these examples one or more branches are used to guide the fluid into one or more of multiple channels, thereby modifying (e.g., dropping) the velocity of fluid and particles in any one channel while keeping particles in focus. In some aspects, the factor by which the velocity is modified (e.g., dropped) depends on parameters including but limited to number of channels, relative width of channels, and/or relative height of channels. An exemplary snapshot of a 3-branch design with particles focused to center is shown in (FIG. 3). In some embodiments the microfluidic channel is divided into 2, 3, 4, 5, 6, 7, 8, 9, or 10 branches.

In some embodiments, ensuring that the particles arrive at the bifurcation exactly when the decision is made and the valve actuation is completed is achieved by a gradual change (e.g., increase or decrease) in width and/or height of the channel. In some examples, the velocity of the particles can be decreased in a controlled manner by guiding the particles into a wider and/or taller channel. In some examples, the velocity of the particles can be increased in a controlled manner by guiding the particles into a wider and/or taller channel. In some embodiments, the angle and/or length of expansion are designed to avoid particles from changing trajectory. This will prevent the particles from getting out of focus.

In some embodiments, ensuring that the particles arrive at the bifurcation exactly when (or prior to when) the decision is made and the valve actuation is completed is achieved by designs within the microfluidic channels. Such designs include but are not limited to curved and/or spiral designs that can delay particles before they arrive at bifurcation, while keeping their lateral positions as well as their relative longitudinal position to each other constant and controlled.

In some embodiments, controlling the velocity of the particles while they are traveling (e.g., flowing) in the microfluidic channel may be achieved by using one or more flow units, e.g., syringe pumps, as provided in the present disclosure.

In some embodiments, the length of the channel may be fixed (or constant) during operation of the flow cell. Alternatively, the length of at least a portion of the channel may be modified (e.g., by stretching, shortening, or bending the at least the portion of the channel), thereby to modify the arrival time of the cells at the bifurcation. The one or both ends and/or one or more sides of the at least the portion of the channel may be operatively coupled to one or more actuators to modify the length of the at least the portion of the channel. Such modified portion of the channel may be disposed prior to or subsequent to the imaging region of the flow cell.

In some aspects, the methods and the systems disclosed herein ensure that the particles arrive at the bifurcation exactly when (or prior to when) the decision is made and valve actuation is completed, as well as ensure that the lateral position of the particles upon their arrival is controlled.

In some aspects, the methods and the systems disclosed herein may comprise determining that the predicted arrival time of a particle (e.g., a cell) at the bifurcation is later than a predetermined duration of time subsequent to (i) when the decision of cell classification is made and (ii) when valve actuation is completed. In such cases, the velocity of the cell's migration along the microfluidic channel and towards the bifurcation may be increased to improve efficiency (e.g., reduce time) of the classification and sorting, yet without negatively affecting efficiency and/or accuracy of the classification and sorting results. In some cases, the predetermined duration of time may be at least 0.00001 seconds, 0.00005 seconds, 0.0001 seconds, 0.0005 seconds, 0.001 seconds, 0.005 seconds, 0.01 seconds, 0.05 seconds, 0.1 seconds, 0.5 seconds, 1 seconds, 5 seconds, 10 seconds, or more. In some cases, the predetermined duration of time may be at most 10 seconds, 5 seconds, 1 second, 0.5 seconds, 0.1 seconds, 0.05 seconds, 0.01 seconds, 0.005 seconds, 0.001 seconds, 0.0005 seconds, 0.0001 seconds, 0.00005 seconds, 0.00001 seconds, or less.

In some embodiments, the methods and the systems disclosed herein may comprise determining predicted arrival times of a particle at a plurality of locations of the flow channel. In some embodiments, the methods and the systems disclosed herein may comprise determining predicted arrival times of a plurality of particles at the bifurcation. In some embodiments, the methods and the systems disclosed herein may comprise determining predicted arrival times of a plurality of particles at a plurality of bifurcations.

In some embodiments, predicting the arrival time of a particle at the bifurcation may comprise determining (e.g., calculating) a probability (i.e., likelihood) of the particle arriving at the bifurcation at the predicted arrival time. The predicted arrival time may have a probability (on a scale from 0 to 1.0) of at least, 0.5, 0.55, 0.6, 0.65, 0.7, 0.75, 0.8, 0.85, 0.9, 0.95, or more (e.g., 1.0). The predicted arrival time may have a probability (on a scale from 1.0 to 0) of at most 1, 0.95, 0.9, 0.85, 0.8, 0.75, 0.7, 0.65, 0.6, 0.55, 0.5, or less. In some embodiments, one or more algorithms for predicting the arrival time may be updated in real time (e.g., by comparing it to an actual arrival time that is measured), thereby to generate a predicted arrival time with a higher probability.

Imaging and Classification

A variety of techniques can be utilized to classify images of cells captured by classification and/or sorting systems in accordance with various embodiments of the disclosure. In some embodiments, the image captures are saved for future analysis/classification either manually or by image analysis software. Any suitable image analysis software can be used for image analysis. In some embodiments, image analysis is performed using OpenCV. In some embodiments, analysis and classification is performed in real time. In some embodiments images are captured at frame rates between 10-10, 000,000 frames per second, for example between 10 frames/sec to about 100 frames/sec, about 10 frames/sec to about 1,000 frames/sec, about 10 frames/sec to about 10,000 frames/sec, about 10 frames/sec to about 100,000 frames/sec, about 10 frames/sec to about 1,000,000 frames/sec, about 10 frames/sec to about 10,000,000 frames/sec, about 100 frames/sec to about 1,000 frames/sec, about 100 frames/sec to about 10,000 frames/sec, about 100 frames/sec to about 100,000 frames/sec, about 100 frames/sec to about 1,000,000 frames/sec, about 100 frames/sec to about 10,000,000 frames/sec, about 1,000 frames/sec to about 10,000 frames/sec, about 1,000 frames/sec to about 100,000 frames/sec, about 1,000 frames/sec to about 1,000,000 frames/sec, about 1,000 frames/sec to about 10,000,000 frames/sec, about 10,000 frames/sec to about 100,000 frames/sec, about 10,000 frames/sec to about 1,000,000 frames/sec, about 10,000 frames/sec to about 10,000,000 frames/sec, about 100,000 frames/sec to about 1,000,000 frames/sec, about 100,000 frames/sec to about 10,000,000 frames/sec, or about 1,000,000 frames/sec to about 10,000,000 frames/sec and classification is performed in real time. In some embodiments images are captured at frame rates between 100,000 and 500,000 frames per second and classification is performed in real time. In some aspects, images are captured at frame rates between 200,000 and 500,000 frames per second and classification is performed in real time. In some aspects, images are captured at frame rates between 300,000 and 500,000 frames per second and classification is performed in real time. In some aspects, images are captured at frame rates between 300,000 and 500,000 frames per second and classification is performed in real time. In some aspects, images are captured at frame rates between 400,000 and 500,000 frames per second and classification is performed in real time.

In some embodiments, the objects placed in the system disclosed herein flow at very high speeds through the channels of the system in order to maintain a high throughput and highly effective inertia focusing. In some aspects, the system of the present disclosure comprises a very high-speed camera with microsecond exposure time to decrease blur in outputted images. In some aspects, the high-speed camera captures images at frame rates between 200,000 and 500,000 frames per second. In some aspects, the high-speed camera captures images at frame rates between 300,000 and 500,000 frames per second. In some aspects, the high-speed camera captures images at frame rates between 300,000 and 500,000 frames per second. In some aspects, the high-speed camera captures images at frame rates between 400,000 and 500,000 frames per second. In some aspects, the system comprises a high-speed strobing light. In some aspects, the system comprises a high-speed strobing light with a slower camera, wherein multiple snapshots of the same object may be imaged onto one image frame (e.g., a single image frame), which may be and separated later with the feature extraction and classification algorithm disclosed herein.

Figure 4:
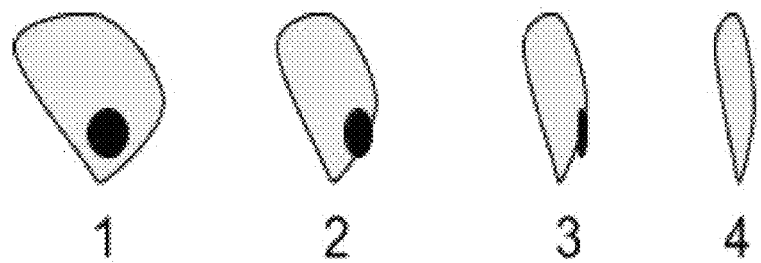
FIG. 4 conceptually illustrates a particle rotating as it moves through the channel.

In some embodiments, the system and methods of the present disclosure comprise collecting a plurality of images of objects in the flow. In some aspects, the plurality of images comprises at least 20 images of cells. In some aspects, the plurality of images comprises at least 19, 18, 17, 16, 15, 14, 13, 12, 11, 10, 9, 8, 7, 6, 5, 4, 3, or 2 images of cells. In some embodiments, the plurality of images comprises images from multiple cell angles. In some aspects, the plurality of images, comprising images from multiple cell angles, help derive extra features from the particle which would typically be hidden if the particle is imaged from a single point-of-view. In some aspects, without wishing to be bound by theory, the plurality of images, comprising images from multiple cell angles, help derive extra features from the particle which would typically be hidden if a plurality of images are combined into a multi-dimensional reconstruction (e.g., a two-dimensional hologram or a three-dimensional reconstruction). In some examples, the microfluidic system may be configured such that the particle (e.g., a cell) is induced to rotate as it moves through the microfluidic channel (FIG. 4). Examples of a plurality of images 1, 2, 3, and 4 of a rotating cell is shown in FIG. 4.

In some embodiments, the systems and methods of present disclosure allow for a tracking ability, wherein the system and methods track a particle (e.g., cell) under the camera and maintain the knowledge of which frames belong to the same particle. In some embodiments, the particle is tracked until it has been classified and/or sorted. In some cases, the particle may be tracked by one or more morphological (e.g., shape, size, area, volume, texture, thickness, roundness, etc.) and/or optical (e.g., light emission, transmission, reflectance, absorbance, fluorescence, luminescence, etc.) characteristics of the particle. In some examples, each particle may be assigned a score (e.g., a characteristic score) based on the one or more morphological and/or optical characteristics, thereby to track and confirm the particle as the particle travels through the microfluidic channel.

In some embodiments, the systems and methods of the disclosure comprise imaging a single particle in a particular field of view of the camera. In some aspects, the system and methods of the present disclosure image multiple particles in the same field of view of camera. Imaging multiple particles in the same field of view of the camera can provide additional advantages, for example it will increase the throughput of the system by batching the data collection and transmission of multiple particles. In some instances, at least about 2, 3, 4, 5, 6, 7, 8, 9, 10, 20, 30, 40, 50, 60, 70, 80, 90, 100, or more particles are imaged in the same field of view of the camera. In some instances, 100 to 200 particles are imaged in the same field of view of the camera. In some instances, at most about 100, 90, 80, 70, 60, 50, 40, 30, 20, 10, 9, 8, 7, 6, 5, 4, 3, or 2 particles are imaged in the same field of view of the camera. In some cases, the number of the particles (e.g., cells) that are imaged in the same field of view may not be changed throughout the operation of the flow cell. Alternatively, the number of the particles (e.g., cells) that are imaged in the same field of view may be changed in real-time throughout the operation of the flow cell, e.g., to increase speed of the classification and/or sorting process without negatively affecting quality or accuracy of the classification and/or soring process.

The imaging region maybe downstream of the focusing region and the ordering region. Thus, the imaging region may not be part of the focusing region and the ordering region. In an example, the focusing region may not comprise or be operatively coupled to any imaging device that is configured to capture one or more images to be used for particle analysis (e.g., cell classification).

Feature Extraction and Classification

In some embodiments, the analysis of the images and/or classification of the particles are performed manually, for example by a human being. In some embodiments, the classification is performed by one or more classifiers. In some embodiments, the classifier is an automated classifier. In some embodiments, the classifier is trained to perform outcome determination based on cell feature and/or pattern recognition. The cell features and/or cell patterns include, but are not limited to, recognition of cell shape, cell diameter, nuclear shape, nuclear diameter, nuclear texture, nuclear edges, nuclear area, nuclear average intensity, nucleus to cytoplasm ratio, cell texture, cell edges, cell area, cell average intensity, DNA content (pgDNA) of the cells and/or the like.

Figure 7:
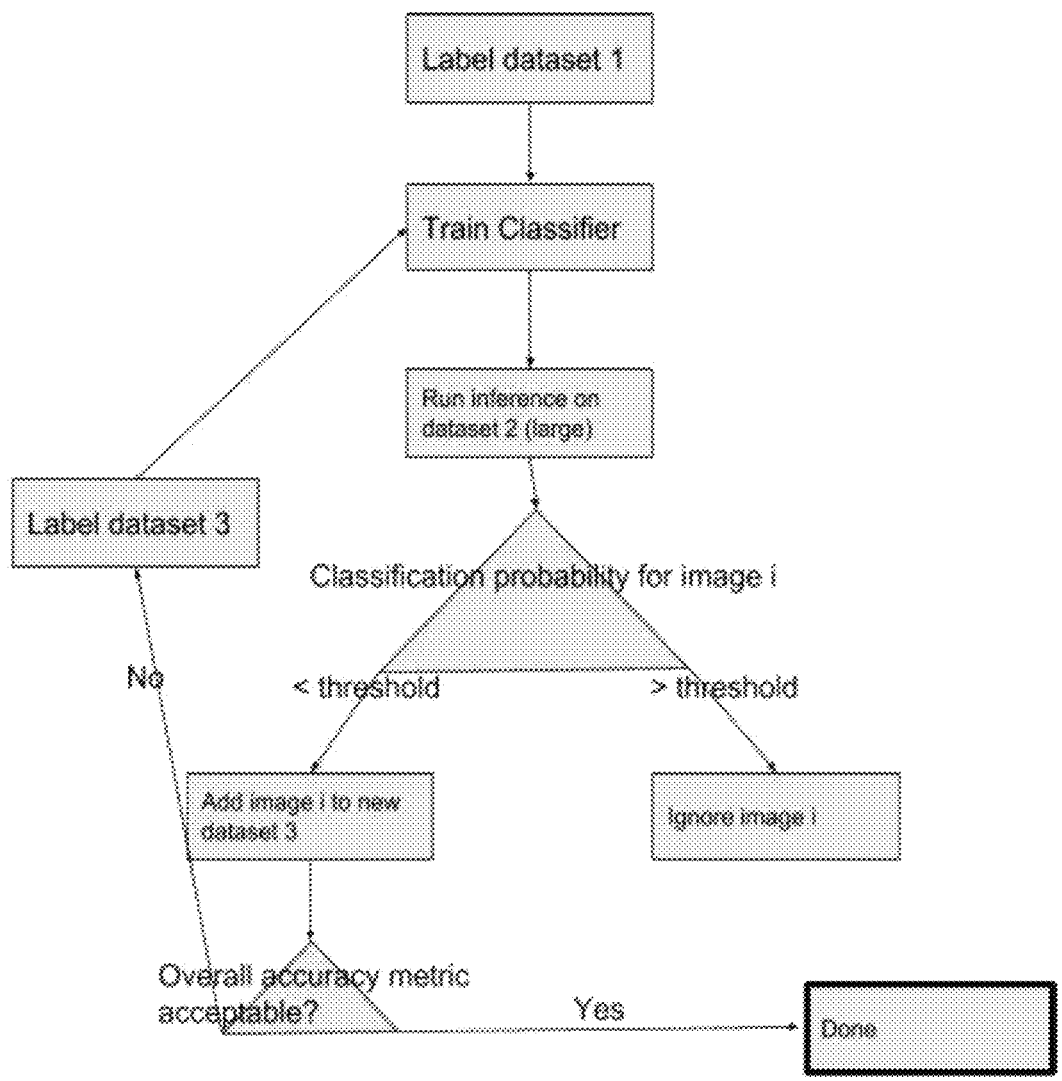
FIG. 7 conceptually illustrates the adaptive labeling framework.

In some embodiments, the one or more classifiers used in the system and methods of the present disclosure are trained using an adaptive labeling approach. In such training approach a classifier is first trained with a first set of known cells. The classifier is then allowed to classify cells in a second set of cells, such that the classifier classifies each cell in the second set of cells with a classification probability, wherein the classification probability is a representation of the classifier's certainty about the classification of a particular cell. After the classification of the second set of cells, cells classified with a classification probability lower than a predefined threshold are selected. These selected cells will represent cases where the classifier is "unsure" about the class. In some cases, this uncertainty may be due to sparsity of that particular type of cells in the first set of known cells. Once, the cells classified with a lower than the pre-defined threshold have been selected, the classifier is trained in a next round to classify these selected cells. In some embodiments, these steps can be repeated till a majority of cells, for e.g. greater than 50% of cells, greater than 55% of cells, greater than 60% of cells, greater than 65% of cells, greater than 70% of cells, greater than 75% of cells, greater than 80% of cells, greater than 85% of cells, greater than 90% of cells, greater than 91% of cells, greater than 91% of cells, greater than 92% of cells, greater than 93% of cells, greater than 94% of cells, greater than 95% of cells, greater than 96% of cells, greater than 97% of cells, greater than 98% of cells, greater than 99% of cells, or 100% of cells are classified with the classification probability equal to or greater than a predefined threshold. The technique is outlined in FIG. 7.

In some cases, the classifier of the present disclosure may be provided with one or more initial distinguishing characteristics (e.g., morphological features) of the first set of known cells during the first training. The classifier may discover one or more additional characteristics of the first set of known cells after the first training. The additional characteristic(s) may be used (i) in conjunction with or (ii) in place of some of the initial distinguishing characteristic(s) during the actual cell classification. In some cases, the classifier may not be provided with any initial distinguishing characteristics of the first set of known cells during the first training. The classifier may be allowed to discover one or more characteristics of the first set of known cells during the first training, and such characteristic(s) may be used during the actual cell classification. The deep learning algorithm that utilizes such classifier may continuously update and revise the classifier (e.g., update and revise distinguishing characteristics of target cells) during multiple rounds of cell classification and sorting.

In some examples, the predefined threshold is a classification probability of greater than 0.50. In some examples, the predefined threshold is a classification probability that is greater than 0.60. In some examples, the predefined threshold is a classification probability that is greater than 0.65, 0.70, 0.75, 0.80, 0.85, 0.90, 0.91, 0.92, 0.93, 0.94, 0.95, 0.96, 0.97, 0.98, or greater than 0.99. In some instances, the threshold probability is a classification probability of 1. In various embodiments, the classification probability is calculated based on validation tests. The validations tests can range from biological validations to software and simulation validations.

In some embodiments, the systems and methods disclosed herein use enhanced neural network designed specifically for cell image classification, for e.g. for single cell image classification. Accordingly, provided herein is a general framework that modifies a convolution neural architecture for single cell image classification. In some aspects, the enhanced neural network is designed by modification of known neural networks designed to work well with ordinary images, such as the image-net. In some aspects the enhanced neural networks are designed by the modification of neural networks such as AlexNet, VGGNet, GoogLeNet, ResNet (residual networks), DenseNet, and Inception networks. In some examples, the enhanced neural networks are designed by modification of ResNet (e.g. ResNet 18, ResNet 34, ResNet 50, ResNet 101, and ResNet 152) or inception networks. In some aspects, the modification comprises a series of network surgery operations that are mainly carried out to improve including inference time and/or inference accuracy.

In some embodiments the modification of the known neural networks comprises shrinking one or more late stage layers of the known neural network. In some example, shrinking the one or more late stage layers results in improved inference time of the neural network. In some instances, later-stage layers play less important roles in cell image data due to the visual features in cell images having lower complexity than objects found in image-net set or similar datasets.

In some aspects, shrinkage of late-stage layers may result in an accuracy loss. In some embodiments, such loss may be compensated at least partially by the addition of back hidden layers to earlier parts of the network. In some examples, shrinking the late stage layers and adding them to an earlier part of the neural network improves accuracy of the classifier even more than keeping them in the late layers.

In various examples, the early vs. late layers are distinguished by their distance to the input layer and/or depth.

Figure 8:
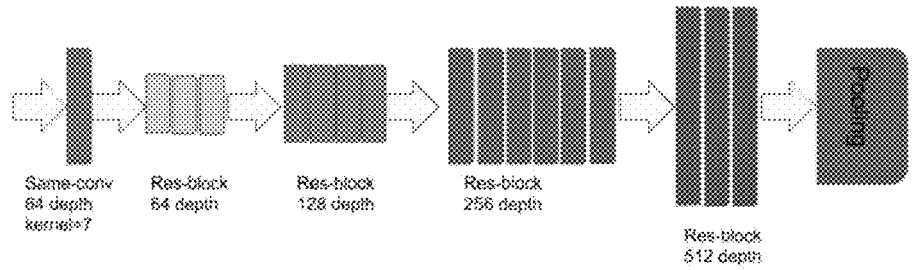
FIG. 8 conceptually illustrates the modifications made to Resnet50, wherein early layers are elongated in exchange of shrinkage of late-stage layers, in order to enhance it and improve its accuracy.
Figure 8:
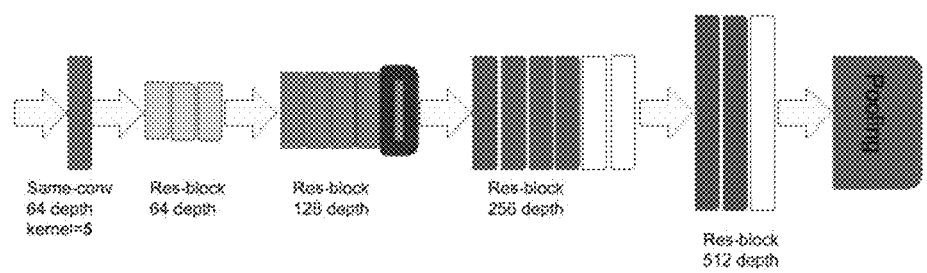

An exemplary enhanced neural network designed by the methods disclosed herein is shown in FIG. 8. The exemplary enhanced neural network is designed by modification of a residual learning network known as ResNet 50. In the modification exemplified, one block of 512 depth and two blocks of 256 depth, both of which are late stage residual layers are removed, and one block is added to the 128 block, which comes earlier in the network. In this particular example, the removal of late stage blocks improved the inference time, and the addition of the 128 depth block gained back and even improved the inference accuracy which was initially feasible with the standard ResNet 50.

In some embodiments, the use of the enhanced neural networks as disclosed herein improves the inference time, wherein the increase in the inference time is calculated as a percent increase using the formula: Percentage increase in the inference time=(inference time using the enhanced neural network-inference time using the known neural network)/inference time using the known neural network×100. In some embodiments, the use of the enhanced neural networks as disclosed herein improves the inference time by at least 10% as compared to the inference time with the known network the enhanced network is derived from. In some examples, the inference time is improved by at least 20%, at least 30%, at least 40%, at least 50%, at least 60%, at least 70%, at least 80%, at least 90%, at least 100%, at least 150%, at least 200%, at least 250%, at least 300%, at least 350%, at least 400%, at least 450%, at least 500%. In some embodiments, the inference accuracy of the enhanced neural networks is improved by at least 10%, at least 20%, at least 30%, at least 40%, at least 50%, at least 60%, at least 70%, at least 80%, at least 90%, at least 100%, at least 150%, at least 200%, at least 250%, at least 300%, at least 350%, at least 400%, at least 450%, at least 500%.

Figure 9:
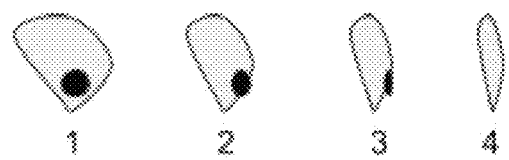
FIG. 9 conceptually illustrates the multi-view ensemble inference framework.
Figure 9:
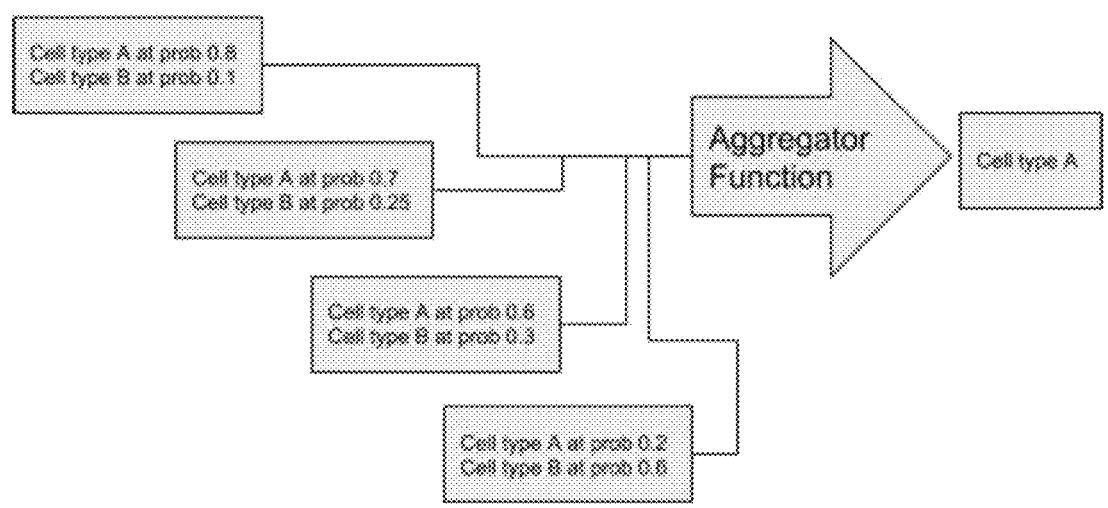

In some embodiments, the accuracy of the system and/or methods disclosed herein is improved by using multiple images belonging to the same cell to assist and increase the accuracy of a classifier. FIG. 9 illustrates this embodiment. In some embodiments, the multiple images comprise images obtained from multiple cell angles. In some embodiments, the images from the multiple cell angles are captured as the cell is rotating in the microfluidic channel. In some embodiments, the images from multiple cell angles are captured by moving one or more imaging devices as the particle passes through the microfluidic channel. In some embodiments, the images from multiple cell angles are captured by multiple imaging devices positioned to capture particle images from specific particle angles. In some embodiments, the images from multiple cell angles are captured by a single imaging device (e.g., a single high-speed camera) to capture particle images from multiple particle angles.

In some embodiments, the accuracy of the systems and methods disclosed herein is further improved by utilizing ensemble methods for classification. The ensemble methods disclosed herein use a set of classifiers which have been trained based on different neural networks, with different initial conditions, etc. The set of classifiers are then allowed to classify the particle and the results from each of the classifier in the set of classifiers are aggregated to determine a final classification of the particle. In some embodiments at least 2, at least 3, at least 4, at least 5, at least 6, at least 7, at least 8, at least 9, or at least 10 classifiers are used. In some cases, deep learning algorithms with ensemble methods may be used for cell classification at multiple angles. A cell may be transported through a flow channel. A plurality of images of the cell from a plurality of different angles may be captured (e.g., due to rotation of the cell, rotational movement of the imaging device, or using a plurality of imaging devices). Subsequently, each of the plurality of images may be analyzed using the deep learning algorithm to classify the cell at each of the plurality of different images at each of the plurality of different angles. As shown in FIG. 9, the analysis may determine a probability of the cell being classified as a specific target cell (e.g., at angle 1, the cell may be cell type A with a probability of 0.8, while the cell may be cell type B with a probability of 0.1). Afterwards, a plurality of such classifications of the cell from the analyzing may be combined (e.g., using an aggregator function) to determine a final classification of the cell.

Figure 10:
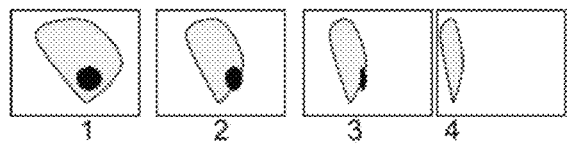
FIG. 10 conceptually illustrates the multi-view to multi-channel data framework.
Figure 10:
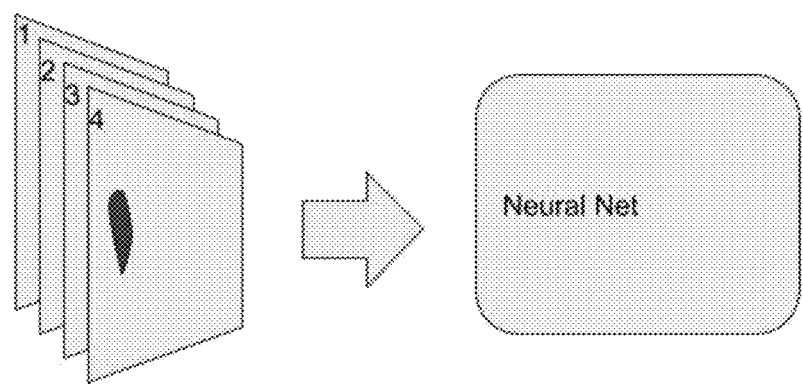

In some embodiments, the system and methods of the present disclosure leverage the multi-view nature of the acquired data by concatenating images obtained from multiple cell angles in a single training or inference procedure to the classifier. In some aspects, the concatenating is similar to that carried out in traditional neural nets to concatenate red green blue (RGB) colors. In some aspects, the present disclosure concatenates separate images belonging to the same cell or particle, wherein both training and classification procedures are sped up since only one inference operation is carried out per cell. FIG. 10 illustrates this embodiment.

In some cases, the plurality of images of the cell from a plurality of angles may be analyzed (e.g., fed into one or more deep learning classifiers) to determine a degree of focus of the cell in each of the plurality of images. In some cases, a probability of the cell being in focus on the image may be determined. The classifiers (e.g., the neural networks operatively coupled to the flow cell) may determine whether the cell is in focus or out of focus (i.e., "blurry") in each of the plurality of images. The classifiers may be provided with one or more parameters (e.g., Fourier transformation algorithms, intensity comparison algorithms, etc.) that can be utilized to determine the degree of focus of the cell in each picture. Alternatively, the classifiers may not be provided with such tools, and the classifiers may learn and discover ("learn") its own parameters, definitions, or characteristics to determine whether the degree of focus of the cell in each image. When some (or majority) of the plurality of images are determined to be out of focus, the deep learning algorithm may update one or more mechanisms of cell flow (e.g., inertia-based z focusing provided herein) to adjust position of a streamline of cells within the microfluidic channel and improve focusing. In some embodiments, different deep learning neural networks may be utilized for the classification of cells and the focusing analysis of the plurality of images. In some embodiments, the same deep learning neural networks may be utilized for both classification of cells and focusing analysis of the plurality of images.

In some cases, one or more parameters of the imaging device(s) (e.g., depth of field, shutter speed, etc.) may be modified (e.g., in real time) based on the degree of focus of the cell to improve focusing. In some cases, one or more other parameters of flow cell (e.g., flow velocity, co-flow, cell rotation, cell density in the fluid, etc.) may be modified (e.g., in real time) based on the degree of focus of the cell to improve focusing.

Sorting

In some embodiments, the systems and the methods of the present disclosure actively sorts a stream of particles. The term sort or sorting as used herein refers to physically separating particles, for e.g. cells, with one or more desired characteristics. The desired characteristic(s) can comprise a feature of the cell(s) analyzed and/or obtained from the image(s) of the cell. Examples of the feature of the cell(s) can comprise a size, shape, volume, electromagnetic radiation absorbance and/or transmittance (e.g., fluorescence intensity, luminescence intensity, etc.), or viability (e.g., when live cells are used).

The flow channel can branch into a plurality of channels, and the cell sorting system can be configured to sort the cell by directing the cell to a selected channel of the plurality of channels based on the analyzed image of the cell. The analyzed image may be indicative of one or more features of the cell, wherein the feature(s) are used as parameters of cell sorting. In some cases, one or more channels of the plurality of channels can have a plurality of sub-channels, and the plurality of sub-channels can be used to further sort the cells that have been sorted once.

Cell sorting may comprise isolating one or more target cells from a population of cells. The target cell(s) may be isolated into a separate reservoir that keeps the target cell(s) separate from the other cells of the population. Cell sorting accuracy may be defined as a proportion (e.g., a percentage) of the target cells in the population of cells that have been identified and sorted into the separate reservoir. In some cases, the cell sorting accuracy of the flow cell provided herein may be at least 80%, 81%, 82%, 83%, 84%, 85%, 86%, 87%, 88%, 89%, 90%, 91%, 92%, 93%, 94%, 95%, 96%, 97%, 98%, 99%, or more (e.g., 99.9% or 100%). In some cases, the cell sorting accuracy of the flow cell provided herein may be at most 100%, 99%, 98%, 7%, 96%, 95%, 94%, 93%, 92%, 91%, 90%, 89%, 88%, 87%, 86%, 85%, 84%, 83%, 82%, 81%, 80%, or less.

In some cases, cell sorting may be performed at a rate of at least 1 cell/second, 5 cells/second, 10 cells/second, 50 cells/second, 100 cells/second, 500 cells/second, 1,000 cells/second, 5,000 cells/second, 10,000 cells/second, 50,000 cells/second, or more. In some cases, cell sorting may be performed at a rate of at most 50,000 cells/second, 10,000 cells/second, 5,000 cells/second, 1,000 cells/second, 500 cells/second, 100 cells/second, 50 cells/second, 10 cells/second, 5 cells/second, 1 cell/second, or less.

In some aspects, the systems and methods disclosed herein use an active sorting mechanism. In various embodiments, the active sorting is independent from analysis and decision making platforms and methods. In various embodiments the sorting is performed by a sorter, which receives a signal from the decision making unit (e.g. a classifier), or any other external unit, and then sorts cells as they arrive at the bifurcation. The term bifurcation as used herein refers to the termination of the flow channel into two or more channels, such that cells with the one or more desired characteristics are sorted or directed towards one of the two or more channels and cell without the one or more desired characteristics are directed towards the remaining channels. In some embodiments, the flow channel terminates into at least 2, 3, 4, 5, 6, 7, 8, 9, 10, or more channels. In some embodiments, the flow channel terminates into at most 10, 9, 8, 7, 6, 5, 4, 3, or 2 channels. In some embodiments, the flow channel terminates in two channels and cells with one or more desired characteristics are directed towards one of the two channels (the positive channel), while cells without the one or more desired characteristics are directed towards the other channel (the negative channel). In some embodiments, the flow channel terminates in three channels and cells with a first desired characteristic are directed to one of the three channels, cells with a second desired characteristic are directed to another of the three channels, and cells without the first desired characteristic and the second desired characteristic are directed to the remaining of the three channels.

In some embodiments, the sorting is performed by a sorter. The sorter may function by predicting the exact time at which the particle will arrive at the bifurcation. To predict the time of particle arrival, the sorter can use any applicable method. In some examples, the sorter predicts the time of arrival of the particle by using (i) velocity of particles (e.g., downstream velocity of a particle along the length of the microfluidic channel) that are upstream of the bifurcation and (ii) the distance between velocity measurement/calculation location and the bifurcation. In some examples, the sorter predicts the time of arrival of the particles by using a constant delay time as an input.

In some cases, prior to the cell's arrival at the bifurcation, the sorter may measure the velocity of a particle (e.g., a cell) at least 1, 2, 3, 4, 5, or more times. In some cases, prior to the cell's arrival at the bifurcation, the sorter may measure the velocity of the particle at most 5, 4, 3, 2, or 1 time. In some cases, the sorter may use at least 1, 2, 3, 4, 5, or more sensors. In some cases, the sorter may use at most 5, 4, 3, 2, or 1 sensor. Example of the sensor(s) may be an imaging device (e.g., a camera such as a high-speed camera), one- or multi-point light (e.g., laser) detector, etc. In some cases, the sorter may use any one of the imaging devices (e.g., the high-speed camera system 114) disposed at or adjacent to the imaging region 138. In some examples, the same imaging device(s) may be used to capture one or more images of a cell as the cell is rotating and migrating within the channel, and the one or more images may be analyzed to (i) classify the cell and (ii) measure a rotational and/or lateral velocity of the cell within the channel and predict the cell's arrival time at the bifurcation. In some examples, the sorter may use one or more sensors that are different than the imaging devices of the imaging region 138. The sorter may measure the velocity of the particle (i) upstream of the imaging region 138, (ii) at the imaging region 138, and/or (iii) downstream of the imaging region 138.

The sorter may comprise or be operatively coupled to a processor, such as a computer processor. Such processor may be the processor 116 that is operatively coupled to the imaging device 114 or a different processor. The processor may be configured to calculate the velocity of a particle (rotational and/or downstream velocity of the particle) an predict the time of arrival of the particle at the bifurcation. The processor may be operatively coupled to one or more valves of the bifurcation. The processor may be configured to direct the valve(s) to open and close any channel in fluid communication with the bifurcation. The processor may be configured to predict and measure when operation of the valve(s) (e.g., opening or closing) is completed.

In some examples, the sorter may comprise a self-included unit (e.g., comprising the sensors, such as the imaging device(s)) which is capable of (i) predicting the time of arrival of the articles and/or (ii) detecting the particle as it arrives at the bifurcation. In order to sort the particles, the order at which the particles arrive at the bifurcation, as detected by the self-included unit, may be matched to the order of the received signal from the decision making unit (e.g. a classifier). In some aspects, controlled particles are used to align and update the order as necessary. In some examples, the decision making unit may classify a first cell, a second cell, and a third cell, respectively, and the sorter may confirm that the first cell, the second cell, and the third cell are sorted, respectively in the same order. If the order is confirmed, the classification and sorting mechanisms (or deep learning algorithms) may remain the same. If the order is different between the classifying and the sorting, then the classification and/or sorting mechanisms (or deep learning algorithms) may be updated or optimized, either manually or automatically. In some aspects, the controlled particles may be cells (e.g., live or dead cells).

In some aspects, the controlled particles may be special calibration beads (e.g., plastic beads, metallic beads, magnetic beads, etc.). In some embodiments the calibration beads used are polystyrene beads with size ranging between about 1 µM to about 50 µM. In some embodiments the calibration beads used are polystyrene beads with size of least about 1 µM. In some embodiments the calibration beads used are polystyrene beads with size of at most about 50 µM. In some embodiments the calibration beads used are polystyrene beads with size ranging between about 1 µM to about 3 µM, about 1 µM to about 5 µM, about 1 µM to about 6 µM, about 1 µM to about 10 µM, about 1 µM to about 15 µM, about 1 µM to about 20 µM, about 1 µM to about 25 µM, about 1 µM to about 30 µM, about 1 µM to about 35 µM, about 1 µM to about 40 µM, about 1 µM to about 50 µM, about 3 µM to about 5 µM, about 3 µM to about 6 µM, about 3 µM to about 10 µM, about 3 µM to about 15 µM, about 3 µM to about 20 µM, about 3 µM to about 25 µM, about 3 µM to about 30 µM, about 3 µM to about 35 µM, about 3 µM to about 40 µM, about 3 µM to about 50 µM, about 5 µM to about 6 µM, about 5 µM to about 10 µM, about 5 µM to about 15 µM, about 5 µM to about 20 µM, about 5 µM to about 25 µM, about 5 µM to about 30 µM, about 5 µM to about 35 µM, about 5 µM to about 40 µM, about 5 µM to about 50 µM, about 6 µM to about 10 µM, about 6 µM to about 15 µM, about 6 µM to about 20 µM, about 6 µM to about 25 µM, about 6 µM to about 30 µM, about 6 µM to about 35 µM, about 6 µM to about 40 µM, about 6 µM to about 50 µM, about 10 µM to about 15 µM, about 10 µM to about 20 µM, about 10 µM to about 25 µM, about 10 µM to about 30 µM, about 10 µM to about 35 µM, about 10 µM to about 40 µM, about 10 µM to about 50 µM, about 15 µM to about 20 µM, about 15 µM to about 25 µM, about 15 µM to about 30 µM, about 15 µM to about 35 µM, about 15 µM to about 40 µM, about 15 µM to about 50 µM, about 20 µM to about 25 µM, about 20 µM to about 30 µM, about 20 µM to about 35 µM, about 20 µM to about 40 µM, about 20 µM to about 50 µM, about 25 µM to about 30 µM, about 25 µM to about 35 µM, about 25 µM to about 40 µM, about 25 µM to about 50 µM, about 30 µM to about 35 µM, about 30 µM to about 40 µM, about 30 µM to about 50 µM, about 35 µM to about 40 µM, about 35 µM to about 50 µM, or about 40 µM to about 50 µM. In some embodiments the calibration beads used are polystyrene beads with size of about 1 µM, about 3 µM, about 5 µM, about 6 µM, about 10 µM, about 15 µM, about 20 µM, about 25 µM, about 30 µM, about 35 µM, about 40 µM, or about 50 µM.

In some embodiments, the sorter (or an additional sensor disposed at or adjacent to the bifurcation) may be configured to validate arrival of the particles (e.g., the cells) at the bifurcation. In some examples, the sorter may be configured to measure an actual arrival time of the particles (e.g., the cells) at the bifurcation. The sorter may analyze (e.g., compare) the predicted arrival time, the actual arrival time, the velocity of the particles downstream of the channel prior to any adjustment of the velocity, and/or a velocity of the particles downstream of the channel subsequent to such adjustment of the velocity. Based on the analyzing, the sorter may modify any operation (e.g., cell focusing, cell rotation, controlling cell velocity, cell classification algorithms, valve actuation processes, etc.) of the flow cell. The validation by the sorter may be used for closed-loop and real-time update of any operation of the flow cell.

In some embodiments, the sorters used in the systems and methods disclosed herein are self-learning cell sorting systems or intelligent cell sorting systems. These sorting systems can continuously learn based on the outcome of sorting. For example, a sample of cells is sorted, the sorted cells are analyzed, and the results of this analysis are fed back to the classifier. In some examples, the cells that are sorted as "positive" (i.e., target cells or cells of interest) may be analyzed and validated. In some examples, the cells that are sorted as "negative" (i.e., non-target cells or cells not of interest) may be analyzed and validated. In some examples, both positive and negative cells may be validated. Such validation of sorted cells (e.g., based on secondary imaging and classification) may be used for closed-loop and real-time update of the primary cell classification algorithms.

In some aspects, the sorters used in the systems and methods disclosed herein do not rely on "supervised labels." In some aspects, the sorters can identify "different looking" sub-populations in a sample, wherein the system automatically identifies and clusters different cell types, in the way of unsupervised learning or semi-supervised learning, by running and collecting their features, thus, by imaging them. In some aspects, the system works by running the sample for a few seconds, wherein the classifier then "learns" the components of the sample, then the actual sorting of those classes begins. In some aspects, the system is a sorter system where the sorting decision is made by artificial intelligence (AI), such as deep learning.

In some embodiments, the system and methods of the present disclosure comprise a cascaded sorting system, wherein a first step bulk sorting is carried out, wherein a subgroup of particles in a sample are monitored sequentially or simultaneously for a positive particle (for example for a cell with one or more desired characteristics), and if any positive particle is detected in the subgroup of particles then, the subgroup of particles is subjected to further sorting. In some embodiments, the cascade sorting comprises capturing an image of a subgroup of a plurality of cells as the plurality of cells pass through a first flow channel; and analyzing the image for a feature. Following which, if the feature is detected then one or more cells in the subgroup are imaged again. In some embodiments, the first step comprises imaging 10 to 100 cells at a time and if any positive cell is detected, the group of 10 to 100 cells is sent to one side of the bifurcation and analyzed again. In some aspects, the first step comprises imaging 20 to 100 cells at a time. In some aspects, the first step comprises imaging 30 to 100 cells at a time. In some aspects, the first step comprises imaging 40 to 100 cells at a time. In some aspects, the first step comprises imaging 50 to 100 cells monitored at a time. In some aspects, the first step comprises imaging 50 to 100 cells at a time. In some aspects, the first step comprises imaging 60 to 100 cells at a time. In some aspects, the first step comprises imaging 70 to 100 cells at a time. In some aspects, the first step comprises imaging 80 to 100 cells at a time. In some aspects, the first step comprises imaging 90 to 100 cells at a time. In some aspects, the first step is followed by a next phase sorting of the subgroup of cells according to the methods described herein. In some embodiments, the next phase sorting is performed by directing the subgroup of cells to a second flow channel and by imaging the cells in the subgroup, single cell at a time according to the methods described herein.

In some examples, a sample of cells may be divided into multiple subgroups of cells. A size of each subgroup of cells may be at least 10, 20, 30, 40, 50, 60, 70, 80, 90, 100, or more cells. The size of each subgroup of cells may be at most 100, 90, 80, 70, 60, 50, 40, 30, 20, 10, or less cells. In a first phase of the cascade sorting, the subgroup of cells may be imaged and analyzed to detect presence of a target cell. If a number of the target cell in the subgroup (or a proportion thereof in the subgroup) is above a predetermined threshold value, then the entire subgroup of cells may be collected or directed for a second phase of the cascade sorting. The predetermined threshold value may be at least 1, 2, 3, 4, 5, 6, 7, 8, 9, 10, or more cells. The predetermined threshold value may be at most 10, 9, 8, 7, 6, 5, 4, 3, 2, or 1 cell. The predetermined proportion may be at least 1%, 2%, 3%, 4%, 5%, 6%, 7%, 8%, 9%, 10%, or more of the subgroup. The predetermined proportion may be at most 10%, 9%, 8%, 7%, 6%, 5%, 4%, 3%, 2%, 1%, or less of the subgroup. In some examples, the entire subgroup may be analyzed during the first phase before making the decision to proceed to the second phase. In some examples, only a portion of the subgroup may be analyzed, and when the predetermined threshold value is reached, the subgroup of cells may be directed to the second phase. During the second phase, the subgroup of cells may be directed back to the same imaging region for classification and sorting of each of the subgroup of cells. Alternatively, the subgroup of cells may be directed to a different imaging region for classification and sorting of each of the subgroup of cells. In another alternative, the subgroup of cells may be collected and stored (e.g., in a reservoir in fluid communication with the flow cell or in a separate reservoir) until the entire sample of cells undergo the first phase of the cascade sorting.

Sorting Techniques

Figure 11:
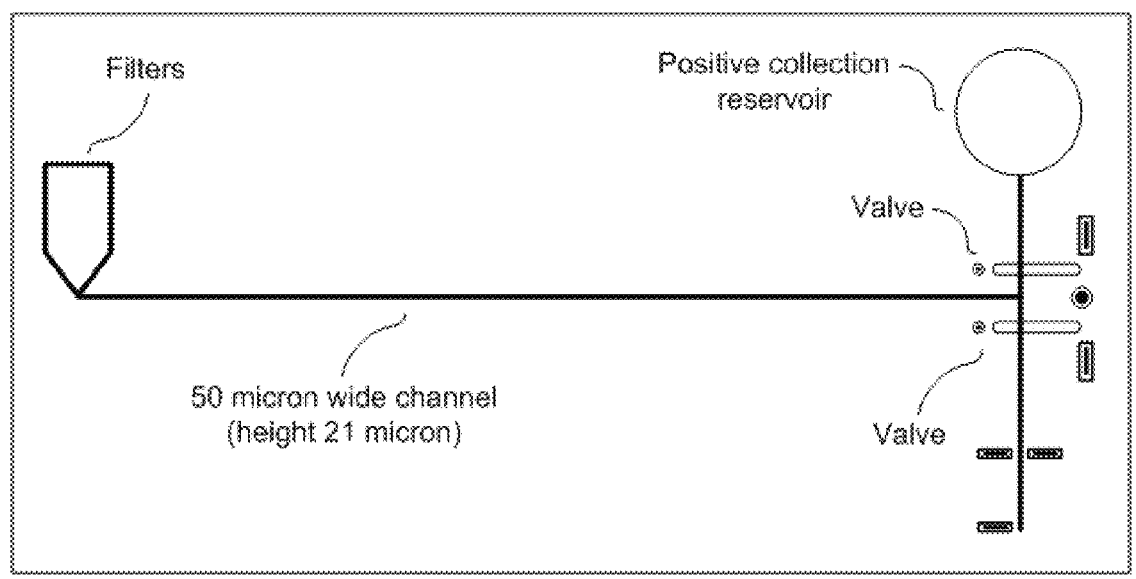
FIG. 11 conceptually illustrates a non-limiting sorting design.

In some embodiments, the methods and systems disclosed herein can use any sorting technique to sort particles. An exemplary design for sorting the cells is shown in FIG. 11, wherein desired cell are directed to/sorted into the positive collection reservoir. At least a portion of the collection reservoir may or may not be pre-filled with a fluid, e.g., a buffer. In some embodiments, the sorting technique comprises closing a channel on one side of the bifurcation to collect the desired cell on the other side. In some aspects, the closing of the channels can be carried out by employing any known technique. In some aspects, the closing is carried out by application of a pressure. In some instances, the pressure is pneumatic actuation. In some aspects, the pressure can be positive pressure or negative pressure. In some embodiments, positive pressure is used. In some examples, one side of the bifurcation is closed by applying pressure and deflecting the soft membrane between top and bottom layers. Pneumatic actuation is further described in WO2001001025A2, which is incorporated herein by reference in its entirety.

In some aspects, the particles to be sorted are directed to one side of the bifurcation by increasing the fluidic resistance on the other side. For example, if one side of the bifurcation can be designed to have a longer channel compared to other side. In such embodiments, the cells normally go to the other (shorter) channel even when both valves are open. In such cases, the cells will go to the longer channel only when the valve on the shorter channel is closed.

Figure 12:
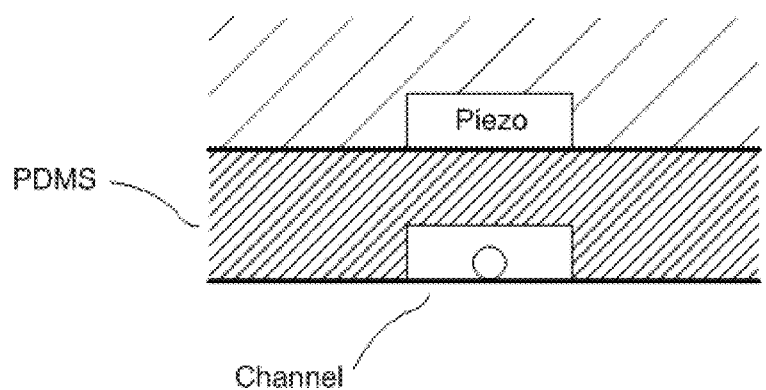
FIG. 12 conceptually illustrates a non-limiting sorting design that uses piezo actuator.

In some embodiments, the closing of a channel on one side of the bifurcation is carried out by application of an electric filed. In some examples, the closing of a channel on one side of the bifurcation is achieved by using piezo actuator. For example, a piezo actuator can be used along to the channel. When a voltage is added to the piezo, the piezo deforms by elongating and/or pinching the channel cross section. A schematic representation of the use of piezo actuator is shown in FIG. 12. In some instances, a deformable material is used for the microfluidic channels, for example polydimethylsiloxane (PDMS) is used.

Figure 13:
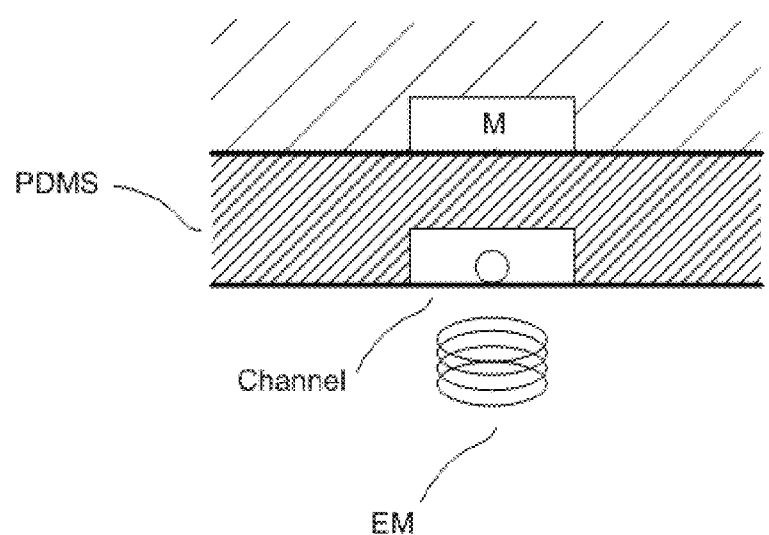
FIG. 13 conceptually illustrates a non-limiting sorting design that uses magnetic actuation.

In some aspects, the closing of a channel on one side of the bifurcation is carried out by application of a magnetic field. In some examples, the closing of a channel on one side of the bifurcation is achieved by using magnetic actuation. For example, an electromagnet (EM) can be used along one side of the channel and a magnet can be used on the other side of the channel. In some instances, when the electromagnet is activated, the magnet becomes attracted to the electromagnet, leaving the channel cross-section to be pinched and closed. In some instances, a deformable material, for example is used for polydimethylsiloxane (PDMS) for the microfluidic channels shown in (FIG. 13).

Sample and Data Collection

In various embodiments, the systems and methods of the present disclosure comprise one or more reservoirs designed to collect the particles after the particles have been sorted. In some embodiments, the number of cells to be sorted is about 1 cell to about 1,000,000 cells. In some embodiments, the number of cells to be sorted is at least about 1 cell. In some embodiments, the number of cells to be sorted is at most about 1,000,000 cells. In some embodiments, the number of cells to be sorted is about 1 cell to about 100 cells, about 1 cell to about 500 cells, about 1 cell to about 1,000 cells, about 1 cell to about 5,000 cells, about 1 cell to about 10,000 cells, about 1 cell to about 50,000 cells, about 1 cell to about 100,000 cells, about 1 cell to about 500,000 cells, about 1 cell to about 1,000,000 cells, about 100 cells to about 500 cells, about 100 cells to about 1,000 cells, about 100 cells to about 5,000 cells, about 100 cells to about 10,000 cells, about 100 cells to about 50,000 cells, about 100 cells to about 100,000 cells, about 100 cells to about 500,000 cells, about 100 cells to about 1,000,000 cells, about 500 cells to about 1,000 cells, about 500 cells to about 5,000 cells, about 500 cells to about 10,000 cells, about 500 cells to about 50,000 cells, about 500 cells to about 100,000 cells, about 500 cells to about 500,000 cells, about 500 cells to about 1,000,000 cells, about 1,000 cells to about 5,000 cells, about 1,000 cells to about 10,000 cells, about 1,000 cells to about 50,000 cells, about 1,000 cells to about 100,000 cells, about 1,000 cells to about 500,000 cells, about 1,000 cells to about 1,000,000 cells, about 5,000 cells to about 10,000 cells, about 5,000 cells to about 50,000 cells, about 5,000 cells to about 100,000 cells, about 5,000 cells to about 500,000 cells, about 5,000 cells to about 1,000,000 cells, about 10,000 cells to about 50,000 cells, about 10,000 cells to about 100,000 cells, about 10,000 cells to about 500,000 cells, about 10,000 cells to about 1,000,000 cells, about 50,000 cells to about 100,000 cells, about 50,000 cells to about 500,000 cells, about 50,000 cells to about 1,000,000 cells, about 100,000 cells to about 500,000 cells, about 100,000 cells to about 1,000,000 cells, or about 500,000 cells to about 1,000,000 cells. In some embodiments, the number of cells to be sorted is about 1 cell, about 100 cells, about 500 cells, about 1,000 cells, about 5,000 cells, about 10,000 cells, about 50,000 cells, about 100,000 cells, about 500,000 cells, or about 1,000,000 cells.

In some embodiments, the number of cells to be sorted is 100 to 500 cells, 200 to 500 cells, 300 to 500 cells, 350 to 500 cells, 400 to 500 cells, or 450 to 500 cells. In some embodiments, the reservoirs may be milliliter scale reservoirs. In some examples, the one or more reservoirs are pre-filled with a buffer and the sorted cells are stored in the buffer. Using the buffer helps to increase the volume of the cells, which can then be easily handled, for example a pipetted. In some examples, the buffer is a phosphate buffer, for example phosphate-buffered saline (PBS).

In some embodiments, the system and methods of the present disclosure comprise a cell sorting technique wherein pockets of buffer solution containing no negative objects are sent to the positive output channel in order to push rare objects out of the collection reservoir. In some aspects, additional buffer solution is sent to the positive output channel to flush out all positive objects at the end of a run, once the channel is flushed clean.

Real-Time Integration

In some embodiments, the system and methods of the present disclosure comprise a combination of techniques, wherein a graphics processing unit (GPU) and a digital signal processor (DSP) are used to run artificial intelligence (AI) algorithms and apply classification results in real-time to the system. In some aspects, the system and methods of the present disclosure comprise a hybrid method for real-time cell sorting.

Validation

In some embodiments, the systems disclosed herein further comprise a validation unit that detects the presence of a particle without getting detailed information, such as imaging. In some instances, the validation unit may be used for one or more purposes. In some examples, the validation unit detects a particle approaching the bifurcation and enables precise sorting. In some examples, the validation unit detects a particle after the particle has been sorted to one of subchannels in fluid communication with the bifurcation. In some examples, the validation unit provides timing information with a plurality of laser spots, e.g., two laser spots. In some instances, the validation unit provides timing information by referencing the imaging time. In some instances, the validation unit provides precise time delay information and/or flow speed of particles.

In some embodiments, the validation unit is a laser-assisted system. In some aspects, the laser-assisted system measures the laser blockage or scattering, and thereby the size of the particle may be inferred. In some aspects, the laser-assisted system measures the laser blockage scattering, and thereby other physical information of the particle may be inferred, including but not limited to the size, the shape, the density, and the texture. In some aspects, the laser-assisted system measures the laser blockage or scattering, and thereby the transient speed of the object may be inferred.

In some embodiments, the validation unit, for e.g. the laser-assisted system, is located after the bifurcation (for e.g. on the positive side, on the negative side, or on both sides). In some examples, such a location of the validation unit provides clarification information on the accuracy and effectiveness of the sorting. In some aspects, the validation system may be used to create a closed feedback loop to adjust the control parameters of the system. In some instances, the closed feedback loop can be used to improve system accuracy and/or to accommodate slow system draft over the course of the experimental run.

In some embodiments, the validation unit comprises a laser-assisted system wherein two or more laser spots are utilized. When the two or more laser spots are closely placed, different methods, disclosed herein, are used to create the two or more laser spots and later separate into two or more independent signals for photo detection. In some embodiments, the distance between the two or more closely spaced laser spots is in the range of 10 µm-about 1,000 µm, for example the distance is between 10 µm to 500 µm, between 50 µm to 500 µm, 100 µm to 500 µm, 150 µm to 500 µm, between 200 µm to 500 µm, between 250 µm to 500 µm, between 300 µm to 500 µm, between 350 µm to 500 µm, between 400 µm to 500 µm, or between 450 µm to 500 µm.

Figure 14A:
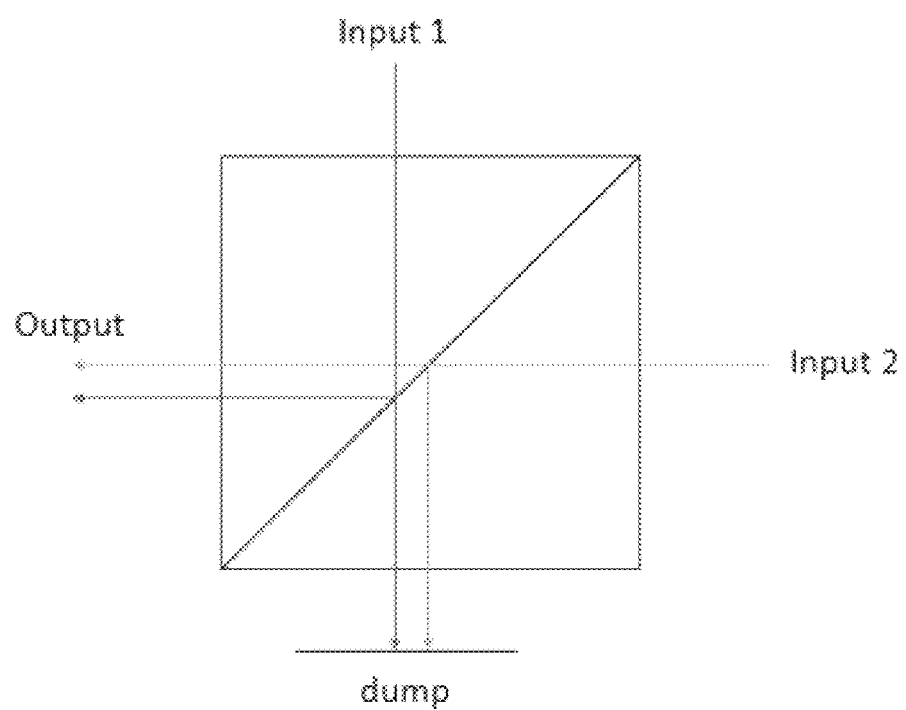
FIG. 14A conceptually illustrates a technique wherein the two lasers from the system of the present disclosure are recombined with a close proximity.

In some embodiments, the two or more closely spaced laser spots come from different optical trains with their respective tilt angle. In some aspects, the two or more closely spaced lasers pass through the same focusing optics but come in with slightly different angles and thus, get focused with slight offset to each other. In some aspects, the two or more closely spaced laser spots have different wavelengths and are recombined with slight offset through a dichroic mirror that passes some lasers while reflecting the other lasers, wherein with the proper arrangement, the lasers can come out together with the desired offset. In some aspects, the two or more lasers spots have different polarizations and can be recombined with a desired offset through a polarization beam splitter. In some aspects, the two or more closely spaced lasers are generated by recombining with a close proximity through a general purpose beamsplitter as shown in FIG. 14A.

Figure 14B:
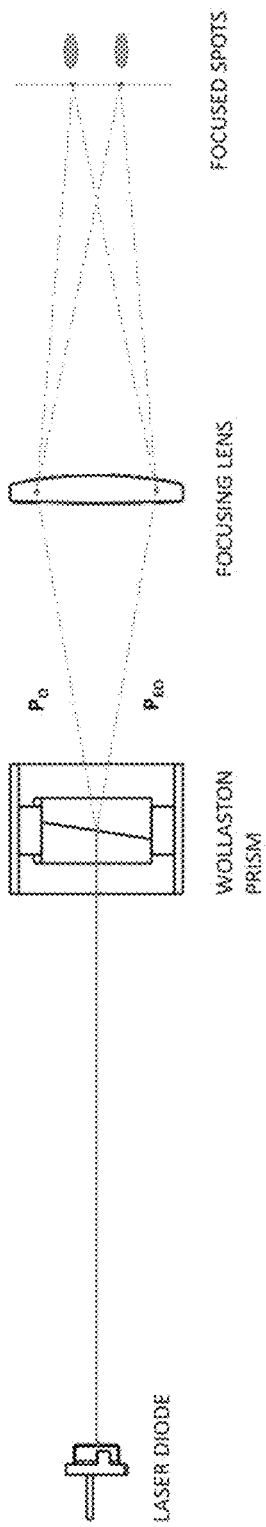
FIGS. 14B and 14C conceptually illustrates examples of focusing two beam focusing system.

In some embodiments, two light spots (e.g., two closely packed laser spots) may be created by utilizing at least one optical source (e.g., at least one diode-based laser) and a prism (e.g., Wollaston or Rochon Prism) to split two polarizations of a light into two beams emerging at a desired angular separation. The two beams (e.g., the two elliptical beams) may be focused onto a same focal plane, separated by a desired distance between the two focused spots. The two beams may be parallel to each other. In some cases, absent any beam shaping optics, the focused spots may be of elliptical in shape, and oriented along the same axis. The distance between the two focused spots may be determined by the prism, the focusing lens, and/or other intermediate optics. The separation between the two focused spots may be controlled by proper choice of the prism (e.g., the Wollaston/Rochon prism) and/or the focal length of the focusing lens. FIG. 14B illustrates an example configuration of a laser diode, a Wollaston prism, and a focusing lens that are configured with respect to one another to create two focus and parallel spots (e.g., ellipsoidal spots) on the same focal plane.

Figure 14C:
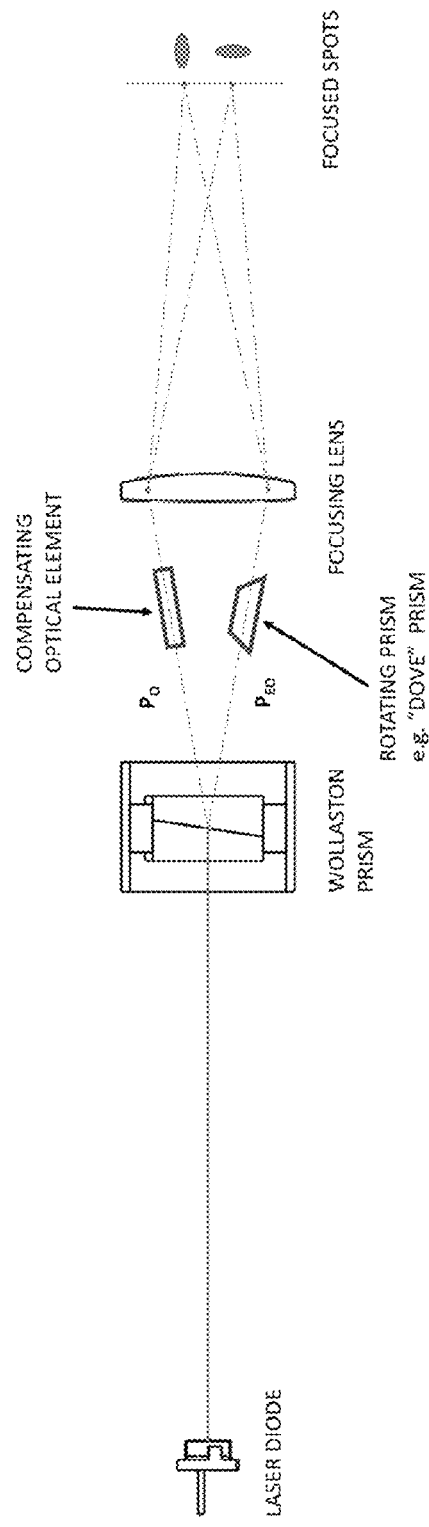

In some embodiments, due to a shape of the light provided by the optical light source (e.g., the elliptical shape of the beam from a non-VCSEL (Vertical-Cavity Surface-Emitting Lasers) laser diode), an outline of one or more resulting focused spots may exhibit a similar shape (e.g., elliptical). In some cases, the shape of the resulting focused spots may be modified with one or more beam shaping optical components, e.g., cylindrical lenses, Powell lenses, anamorphic lenses, etc. The angle between the two focused spots (e.g., the two elliptically shaped focused spots) can be further controlled by utilizing a prism or a pair of prisms, such as a Dove or similar prism, in one or both legs of the optical paths, thereby to rotate the beam along that path by the desired angle. In an example, a major axis of one of the two focused spots can be rotated (i.e., clocked) to be perpendicular to that of the other of the two focused spots by inserting a Dove prism in one leg of the two beams, while, optionally, inserting a compensation optic in the other leg of the optical path. Such a configuration of non-parallel laser spots can be utilized in detecting cells in "L" channel junctions. Similarly, different clocking angles generated by inserting appropriate type and/or number of prisms can be utilized to detect cells in "Y" or other channel junction configurations. FIG. 14C illustrates an example configuration of a laser diode, a Wollaston prism, a rotating prism (e.g., a Dove prism) along a bottom beam path, a compensating optical element along a top beam path, and a focusing lens in optical communication with both top and bottom beam paths to create two focus and parallel spots (e.g., ellipsoidal spots) on the same focal plane.

In some embodiments, the signals from the two or more closely spaced lasers can be separated by reversing the creation methods described herein. In some aspects, the signals of the two or more lasers can be separated using optical components with a good alignment. In some instances, the optical component is a round glass ball. In some aspects, the signals of the two or more lasers can be separated by sending the signal to a position-sensitive detector. In some instances, the position-sensitive detector is a dual photodetector. In some instances, the position-sensitive detector is a quad photodetector. In some aspects, the present disclosure comprises a laser-assisted system wherein two closely spaced laser spots are utilized. In some aspects, the laser spots comprise a slit in between, wherein the change in different detection area is used to calculate the original two laser signal changes.

Figure 15:
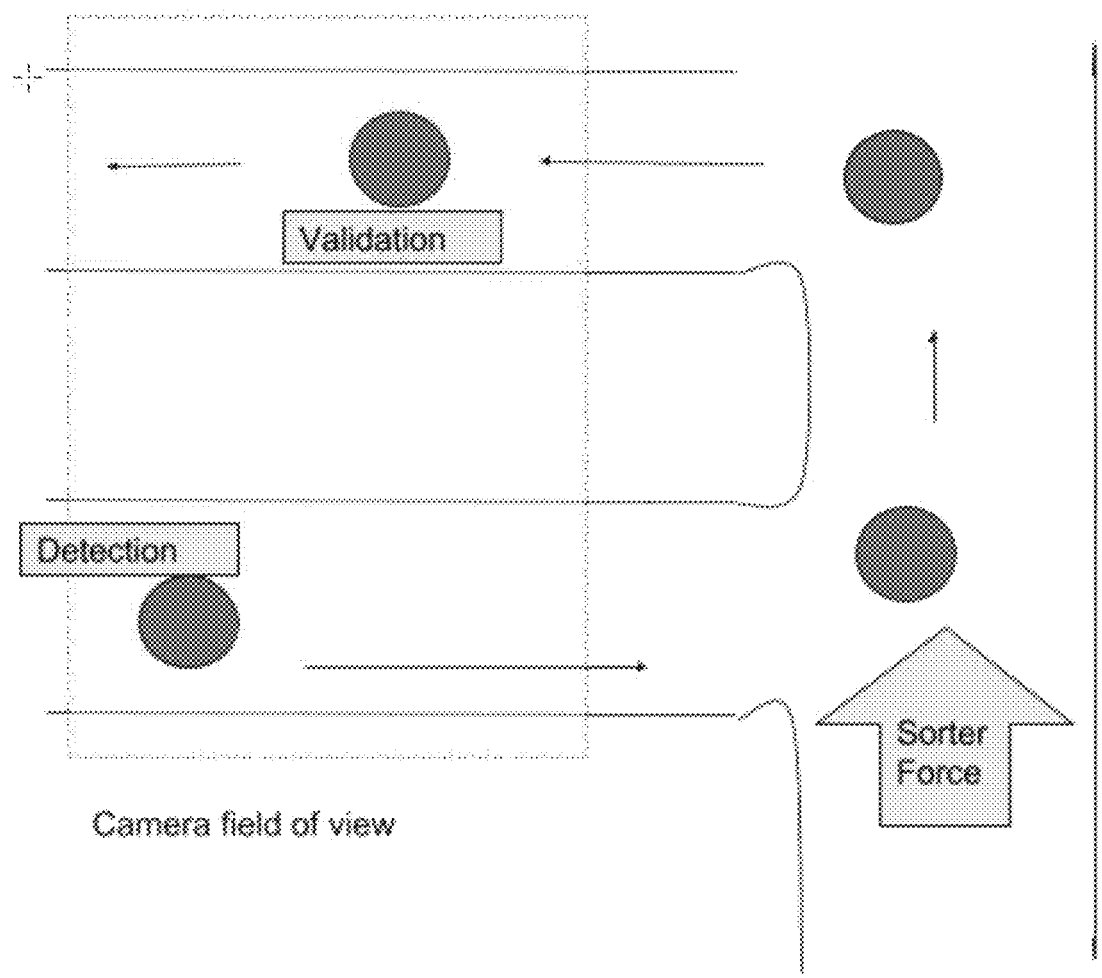
FIG. 15 conceptually illustrates a validation technique that comprises a backchannel design.

In some embodiments, the validation of particle sorting by the methods and the system disclosed herein is performed by the using the back channel design as shown in FIG. 15. In these embodiments, the validation comprises imaging both the flow channel where the cells are imaged for the first time, known as the forward channel, and the outlet, where the cells flow after being sorted. In some aspects, the outlet is designed as a backchannel that fits in the same field of view as the imaging device used to image the particles in the flow channel. In some aspects, the outlet particles can be identified against the forward channel particles by their location and/or velocity. In some instances, the velocity of the particles is positive in the forward channel. In some instances, the velocity of the particles is negative in the backward channel.

Additional Analysis

Sorted particles (e.g., "positive" or "negative" cells) may be subject to additional treatment and/or analysis steps. The additional treatment and/or analysis may include, but are not limited to, cell culture (e.g., proliferation, differentiation, etc.), cell permeabilization and fixation, cell staining by a probe, mass cytometry, multiplexed ion beam imaging (MIBI), confocal imaging, nucleic acid (e.g., DNA, RNA) or protein extraction, polymerase chain reaction (PCR), target nucleic acid enrichment, sequencing, sequence mapping, etc. In some cases, the sorted particles may be transferred (e.g., manually) to one or more instruments configured to execute any one of the additional treatment and/or analysis steps. In some cases, the flow channel may be in fluid communication with such instrument(s) for automated transfer and execution of any one of the additional treatment and/or analysis steps.

Examples of the probe used for cell staining (or tagging) may include, but are not limited to, a fluorescent probe (e.g., for staining chromosomes such as X, Y, 13, 18 and 21 in fetal cells), a chromogenic probe, a direct immunoagent (e.g. labeled primary antibody), an indirect immunoagent (e.g., unlabeled primary antibody coupled to a secondary enzyme), a quantum dot, a fluorescent nucleic acid stain (such as DAPI, Ethidium bromide, Sybr green, Sybr gold, Sybr blue, Ribogreen, Picogreen, YoPro-1, YoPro-2 YoPro-3, YOYo, Oligreen acridine orange, thiazole orange, propidium iodine, or Hoeste), another probe that emits a photon, or a radioactive probe.

In some cases, the instrument(s) for the additional analysis may comprise a computer executable logic that performs karyotyping, in situ hybridization (ISH) (e.g., florescence in situ hybridization (FISH), chromogenic in situ hybridization (CISH), nanogold in situ hybridization (NISH)), restriction fragment length polymorphism (RFLP) analysis, polymerase chain reaction (PCR) techniques, flow cytometry, electron microscopy, quantum dot analysis, or detects single nucleotide polymorphisms (SNPs) or levels of RNA.

Samples

In some embodiments, the particles (for e.g. cells) analyzed by the systems and methods disclosed herein are comprised in a sample. The sample may be a biological sample obtained from a subject. In some embodiments, the biological sample comprises a biopsy sample from a subject. In some embodiments, the biological sample comprises a tissue sample from a subject. In some embodiments, the biological sample comprises liquid biopsy from a subject. In some embodiments, the biological sample can be a solid biological sample, e.g., a tumor sample. In some embodiments, a sample from a subject can comprise at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or at least about 100% tumor cells from a tumor.

In some embodiments, the sample can be a liquid biological sample. In some embodiments, the liquid biological sample can be a blood sample (e.g., whole blood, plasma, or serum). A whole blood sample can be subjected to separation of cellular components (e.g., plasma, serum) and cellular components by use of a Ficoll reagent. In some embodiments, the liquid biological sample can be a urine sample. In some embodiments, the liquid biological sample can be a perilymph sample. In some embodiments, the liquid biological sample can be a fecal sample. In some embodiments, the liquid biological sample can be saliva. In some embodiments, the liquid biological sample can be semen. In some embodiments, the liquid biological sample can be amniotic fluid. In some embodiments, the liquid biological sample can be cerebrospinal fluid. In some embodiments, the liquid biological sample can be bile. In some embodiments, the liquid biological sample can be sweat. In some embodiments, the liquid biological sample can be tears. In some embodiments, the liquid biological sample can be sputum. In some embodiments, the liquid biological sample can be synovial fluid. In some embodiments, the liquid biological sample can be vomit.

In some embodiments, samples can be collected over a period of time and the samples may be compared to each other or with a standard sample using the systems and methods disclosed herein. In some embodiments the standard sample is a comparable sample obtained from a different subject, for example a different subject that is known to be healthy or a different subject that is known to be unhealthy. Samples can be collected over regular time intervals, or can be collected intermittently over irregular time intervals.

In some embodiments, the subject may be an animal (e.g., human, rat, pig, horse, cow, dog, mouse). In some instances, the subject is a human and the sample is a human sample. The sample may be a fetal human sample. The sample may be from a multicellular tissue (e.g., an organ (e.g., brain, liver, lung, kidney, prostate, ovary, spleen, lymph node, thyroid, pancreas, heart, skeletal muscle, intestine, larynx, esophagus, and stomach), a blastocyst). The sample may be a cell from a cell culture. In some sample the subject is a pregnant human, or a human suspected to be pregnant.

The sample may comprise a plurality of cells. The sample may comprise a plurality of the same type of cell. The sample may comprise a plurality of different types of cells. The sample may comprise a plurality of cells at the same point in the cell cycle and/or differentiation pathway. The sample may comprise a plurality of cells at different points in the cell cycle and/or differentiation pathway.

The plurality of samples may comprise one or more malignant cell. The one or more malignant cells may be derived from a tumor, sarcoma, or leukemia.

The plurality of samples may comprise at least one bodily fluid. The bodily fluid may comprise blood, urine, lymphatic fluid, saliva. The plurality of samples may comprise at least one blood sample.

The plurality of samples may comprise at least one cell from one or more biological tissues. The one or more biological tissues may be a bone, heart, thymus, artery, blood vessel, lung, muscle, stomach, intestine, liver, pancreas, spleen, kidney, gall bladder, thyroid gland, adrenal gland, mammary gland, ovary, prostate gland, testicle, skin, adipose, eye or brain.

The biological tissue may comprise an infected tissue, diseased tissue, malignant tissue, calcified tissue or healthy tissue.

Non-Invasive Prenatal Testing (NIPT)

Conventional prenatal screening methods for detecting fetal abnormalities and for sex determination use fetal samples acquired through invasive techniques, such as amniocentesis and chorionic villus sampling (CVS). Ultrasound imaging is also used to detect structural malformations such as those involving the neural tube, heart, kidney, limbs and the like. Chromosomal aberrations such as the presence of extra chromosomes, such as Trisomy 21 (Down syndrome), Klinefelter's syndrome, Trisomy 13 (Patau syndrome), Trisomy 18 (Edwards syndrome), or the absence of chromosomes, such as Turner's syndrome, or various translocations and deletions can be currently detected using CVS and/or amniocentesis. Both techniques require careful handling and present a degree of risk to the mother and to the pregnancy.

Prenatal diagnosis is offered to women over the age of 35 and/or women who are known to carry genetic diseases, as balanced translocations or microdeletions.

Chorionic villus sampling (CVS) is performed between the $9^{th}$ and the $14^{th}$ week of gestation. CVS involves the insertion of a catheter through the cervix or the insertion of a needle into the abdomen of the subject/patient. The needle or catheter is used to remove a small sample of the placenta, known as the chorionic villus. The fetal karyotype is then determined within one to two weeks of the CVS procedure. Due to the invasive nature of the CVS procedure, there is a 2 to 4% procedure-related risk of miscarriage. CVS is also associated with an increased risk of fetal abnormalities, such as defective limb development, which are presumably due to hemorrhage or embolism from the aspirated placental tissues.

Amniocentesis is performed between the $16^{th}$ and the $20^{th}$ week of gestation. Amniocentesis involves the insertion of a thin needle through the abdomen into the uterus of the patient. This procedure carries a 0.5 to 1% procedure-related risk of miscarriage. Amniotic fluid is aspirated by the needle and fetal fibroblast cells are further cultured for 1 to 2 weeks, following which they are subjected to cytogenetic and/or fluorescence in situ hybridization (FISH) analyses.

Recent techniques have been developed to predict fetal abnormalities and predict possible complications in pregnancy. These techniques use material blood or serum samples and have focused on the use of three specific markers, including alpha-fetoprotein (AFP), human chorionic gonadotrophin (hCG), and estriol. These three markers are used to screen for Down's syndrome and neural tube defects. Maternal serum is currently being used for biochemical screening for chromosomal aneuploidies and neural tube defects.

The passage of nucleated cells between the mother and fetus is a well-studied phenomenon. Using the fetal cells that are present in maternal blood for non-invasive prenatal diagnosis prevents the risks that are usually associated with conventional invasive techniques. Fetal cells include fetal trophoblasts, leukocytes, and nucleated erythrocytes from the maternal blood during the first trimester of pregnancy. This the, the isolation of trophoblasts from the maternal blood is limited by their multinucleated morphology and the availability of antibodies, whereas the isolation of leukocytes is limited by the lack of unique cell markers which differentiate maternal from fetal leukocytes. Furthermore, since leukocytes may persist in the maternal blood for as long as 27 years, residual cells are likely to be present in the maternal blood from previous pregnancies.

In some embodiments, the system and methods disclosed herein are used for non-invasive prenatal testing (NIPT), wherein the methods are used to analyze maternal serum or plasma samples from a pregnant female. In some aspects, the system and methods are used for non-invasive prenatal diagnosis. In some aspects, the system and methods disclosed herein can be used to analyze maternal serum or plasma samples derived from maternal blood. In some aspects, as little as 10 μL of serum or plasma can be used. In some aspects, larger samples are used to increase accuracy, wherein the volume of the sample used is dependent upon the condition or characteristic being detected.

In some embodiments, the system and methods disclosed herein are used for non-invasive prenatal diagnosis including but not limited to sex determination, blood typing and other genotyping, detection of pre-eclampsia in the mother, determination of any maternal or fetal condition or characteristic related to either the fetal DNA itself or the quantity or quality of the fetal DNA in the maternal serum or plasma, and identification of major or minor fetal malformations or genetic diseases present in a fetus. In some aspects, fetus is a human fetus.

In some embodiments, the system and methods disclosed herein are used to analyze serum or plasma from maternal blood samples, wherein the serum or plasma preparation is carried out by standard techniques and subjected to a nucleic acid extraction process. In some aspects, the serum or plasma is extracted using a proteinase K treatment followed by phenol/chloroform extraction.

In some embodiments, the system and methods disclosed herein are used to image cells from maternal serum or plasma acquired from a pregnant female subject. In some aspects, the subject is a human. In some aspects, the pregnant female human subject is over the age of 35. In some aspects, the pregnant female human subject is known to carry a genetic disease. In some aspects, the subject is a human. In some aspects, the pregnant female human subject is over the age of 35 and is known to carry a genetic disease.

In some embodiments, the system and methods disclosed herein are used to analyze fetal cells from maternal serum or plasma. In some aspects, the cells that are used for non-invasive prenatal testing using the system and methods disclosed herein are fetal cells such as fetal trophoblasts, leukocytes, and nucleated erythrocytes. In some aspects, fetal cells are from the maternal blood during the first trimester of pregnancy.

In some embodiments, the system and methods disclosed herein are used for non-invasive prenatal diagnosis using fetal cells comprising trophoblast cells. In some aspects, trophoblast cells using the present disclosure are retrieved from the cervical canal using aspiration. In some aspects, trophoblast cells using the present disclosure are retrieved from the cervical canal using cytobrush or cotton wool swabs. In some aspects, trophoblast cells using the present disclosure are retrieved from the cervical canal using endocervical lavage. In some aspects, trophoblast cells using the present disclosure are retrieved from the cervical canal using intrauterine lavage.

In some embodiments, the system and methods disclosed herein are used to analyze fetal cells from maternal serum or plasma, wherein the cell population is mixed and comprises fetal cells and maternal cells. In some aspects, the system and methods of the present disclosure are used to identify embryonic or fetal cells in a mixed cell population. In some embodiments, the system and methods of the present disclosure are used to identify embryonic or fetal cells in a mixed cell population, wherein nuclear size and shape are used to identify embryonic or fetal cells in a mixed population. In some embodiments, the systems and methods disclosed herein are used to sort fetal cells from a cell population.

In some embodiments, the system and methods disclosed herein are used to measure the count of fetal nucleated red blood cells (RBCs), wherein an increase in fetal nucleated RBC count (or proportion) indicates the presence of fetal aneuploidy. In some examples, a control sample (e.g., a known blood or plasma sample from a non-pregnant individual) may be used for comparison. In some cases, the system and methods disclosed herein are used to provide a likelihood (i.e., probability) of a presence of an abnormal condition in a fetus.

In some embodiments, the system and methods disclosed herein are used to image cells from maternal serum or plasma acquired from a pregnant female subject. In some aspects, the cells are not labelled. In some aspects, the cells are in a flow. In some aspects, the cells are imaged from different angles. In some aspects, the cells are live cells. In some aspects, the cells are housed in a flow channel within the system of the present disclosure, wherein the flow channel has walls formed to space the plurality of cells within a single streamline. In some aspects, the cells are housed in a flow channel within the system of the present disclosure, wherein the flow channel has walls formed to rotate the plurality of the cells within a single streamline.

In some embodiments, the system and methods disclosed herein are used to image cells from maternal serum or plasma acquired from a pregnant female subject. In some aspects, a plurality of images of the cells is collected using the system and methods of the present disclosure. In some aspects, the plurality of images is analyzed to determine if specific disease conditions are present in the subject, wherein the cells are in a flow during the imaging and wherein the plurality of images comprises images of the cells from a plurality of angles. In some aspects, subject is the fetus. In some aspects, subject is pregnant female subject.

Sperm Analysis

In some embodiments, the sample used in the methods and systems described herein is a semen sample, and the system and methods of the present disclosure are used to identify sperm quality and/or gender. In these embodiments, the methods described herein comprise imaging the semen sample from the subject according to the methods described herein and analyzing the sperms in the semen sample for one or more features. In some embodiments, the systems and methods described herein are used to obtain a sperm count. In some aspects, the systems and methods described herein are used to obtain information about sperm viability and/or health. In some aspects, the systems and methods described herein are used to obtain information about sperm gender. In some embodiments, the sorting systems and methods described herein are used for and automated enrichment of sperms with desired morphological features. In some embodiment, the enriched sperms obtained according to the methods and systems described herein are used for in-vitro fertilization. In some aspects, the features are associated with health, motility, and/or gender.

Cancer Cells

Many cancers are diagnosed in later stages of the disease because of low sensitivity of existing diagnostic procedures and processes. More than 1.5 million people are diagnosed with cancer every year in the USA, of which 600,000 people die (Jemal et al. 2010). Currently, the first cancer screening procedure involves the detection of a tumor. Many cancer tumors, such as breast cancer are detected by self- or clinical examination. However, these tumors are typically detected only after the tumor reach a volume of 1 mL or 1 cc, when it contains approximately $10^9$ cells. Routine screening by mammography is more sensitive and allows detection of a tumor before it becomes palpable, but only after they reach an inch in diameter. MRI, positron emission tomography (PET) and single-photon emission computed tomography (SPECT) can reveal even smaller tumors than can be detected by mammograms. However, these imaging methods present significant disadvantages. Contrast agents for magnetic resonance imaging (MRI) are toxic and radionuclides delivered for SPECT or PET examination are sources of ionizing radiation. Because of its relatively poor resolution, ovarian cancer often requires several follow up scans with computed tomography (CT) or MRI, while undertaking all precautions to protect possible pregnancies, to reveal fine anatomy of developing tumors (Shin et al. 2011). Additionally, all of these diagnostic techniques require dedicated facilities, expensive equipment, well trained staff, and financial coverages.

Cancer is commonly diagnosed in patients by obtaining a sample of the suspect tissue and examining the tissue under a microscope for the presence of malignant cells. While this process is relatively straightforward when the anatomic location of the suspect tissue is known, it can become quite challenging when there is no readily identifiable tumor or pre-cancerous lesion. For example, to detect the presence of lung cancer from a sputum sample requires one or more relatively rare cancer cells to be present in the sample. Therefore, patients having lung cancer may not be diagnosed properly if the sample does not perceptively and accurately reflect the conditions of the lung.

Conventional light microscopy, which utilizes cells mounted on glass slides, can only approximate 2D and 3D measurements because of limitations in focal plane depth, sampling angles, and problems with cell preparations that typically cause cells to overlap in the plane of the image. Another drawback of light microscopy is the inherent limitation of viewing through an objective lens where only the area within the narrow focal plane provides accurate data for analysis.

Flow cytometry methods generally overcome the cell overlap problem by causing cells to flow one-by-one in a fluid stream. Unfortunately, flow cytometry systems do not generate images of cells of the same quality as traditional light microscopy, and, in any case, the images are not three-dimensional.

In some embodiments, the system and methods disclosed herein enable the acquisition of three-dimensional imaging data of individual cells, wherein each individual cell from a cell population is imaged from a plurality of angles. In some aspects, the present disclosure is used to diagnose cancer, wherein individual cancer cells are identified, tracked, and grouped together. In some aspects, the cells are live.

In some embodiments, the system and methods disclosed herein are used for cancer diagnosis in a subject, the method comprising imaging a cell in a biological sample from the subject to collect a plurality of images of the cell and analyzing the plurality of images to determine if cancerous cells are present in the subject, wherein the cancerous cell is in a flow during imaging and is spinning, and wherein the plurality of images comprise images from a different spinning angles.

In some embodiments, the system and methods disclosed herein are used for cancer cell detection, wherein the cancerous cells are from biological samples and are detected and tracked as they pass through the system of the present disclosure.

In some embodiments, the system and methods disclosed herein are used to identify cancer cells from biological samples acquired from mammalian subjects, wherein the cell population is analyzed by nuclear detail, nuclear contour, presence or absence of nucleoli, quality of cytoplasm, quantity of cytoplasm, nuclear aspect ratio, cytoplasmic aspect ratio, or nuclear to cytoplasmic ratio. In some aspects, the cancer cells that are identified indicate the presence of cancer in the mammalian sample, including but not limited to, lymphoma, myeloma, neuroblastoma, breast cancer, ovarian cancer, lung cancer, rhabdomyosarcoma, small-cell lung tumors, primary brain tumors, stomach cancer, colon cancer, pancreatic cancer, urinary bladder cancer, testicular cancer, lymphomas, thyroid cancer, neuroblastoma, esophageal cancer, genitourinary tract cancer, cervical cancer, endometrial cancer, adrenal cortical cancer, or prostate cancer. In some aspects, the cancer is metastatic cancer. In some aspects, the cancer is an early stage cancer.

In some embodiments, the system and methods disclosed herein are used to image a large number of cells from a subject and collect a plurality of images of the cell, and to then classify the cells based on an analysis of one or more of the plurality of images; wherein the plurality of images comprise images from a plurality of cell angles and wherein the cell is tracked until the cell has been classified. In some aspects, the tracked cells are classified as cancerous. In some aspects, the subject is a human.

In some embodiments, the cells used in the methods disclosed herein are live cells. In some aspects, the cells that are classified as cancerous cells are isolated and subsequently cultured for potential drug compound screening, testing of a biologically active molecule, and/or further studies.

In some embodiments, the system and methods disclosed herein are used to identify cancer cells from a cell population from a mammalian subject. In some aspects, the subject is a human. In some aspects, the system and methods disclosed herein are used to determine the progression of a cancer, wherein samples from a subject are obtained from two different time points and compared using the methods of the present disclosure. In some aspects, the system and methods disclosed herein are used to determine the effectiveness of an anti-cancer treatment, wherein samples from a subject are obtained before and after anti-cancer treatment and comparing the two samples using the methods of the present disclosure.

In some embodiments, the system and methods disclosed herein comprise a cancer detection system that uses a rapidly trained neural network, wherein the neural network detects cancerous cells by analyzing raw images of the cell and provides imaging information from the pixels of the images to a neural network. In some aspects, the neural network performs recognition and identification of cancerous cells using information derived from an image of the cells, among others, the area, the average intensity, the shape, the texture, and the DNA (pgDNA) of the cells. In some aspects, the neural network performs recognition of cancerous cells using textural information derived from an image of the cells, among them angular second moment, contrast, coefficient of correlation, sum of squares, difference moment, inverse difference moment, sum average, sum variance, sum entropy, entry, difference variance, difference entropy, information measures, maximal correlation coefficient, coefficient of variation, peak transition probability, diagonal variance, diagonal moment, second diagonal moment, product moment, triangular symmetry and blobness.

Bacteria from Human Cells

In some embodiments, the methods disclosed herein are used for bacterial detection, wherein the human cells containing bacteria are from biological samples and are detected and tracked as they pass through the system of the present disclosure.

In some embodiments, the system and methods disclosed herein enable the acquisition of three-dimensional imaging data of bacteria present in a sample, wherein each individual bacterium is imaged from a plurality of angles. In some embodiments, the system and methods disclosed herein are used for bacterial detection, wherein the bacteria is from biological samples and are detected and tracked as they pass through the system of the present disclosure.

In some embodiments, the system and methods disclosed herein are used to detect bacteria in fluids, including blood, platelets, and other blood products for transfusion, and urine. In some aspects, the present disclosure provides a method for separating intact eukaryotic cells from suspected intact bacterial cells that may be present in the fluid sample. In some aspects, the present disclosure identifies certain bacterial species, including but not limited to: *Bacillus cereus, Bacillus subtilis, Clostridium perfringens, Corynebacterium species, Escherichia coli, Enterobacter cloacae, Klebsiella oxytoca, Propionibacterium acnes, Pseudomonas aeruginosa, Salmonella choleraesuis, Serratia marcesens, Staphylococcus aureus, Staphylococcus epidermidis, Streptococcus pyogenes*, and *Streptococcus viridans*.

In some embodiments, the system and methods disclosed herein comprise a bacterial detection system that uses a rapidly trained neural network, wherein the neural network detects bacteria by analyzing raw images of the cell and provides imaging information from the pixels of the images to a neural network. In some aspects, the neural network performs recognition and identification of bacteria using information derived from an image of the bacteria, among others, the area, the average intensity, the shape, the texture, and the DNA (pgDNA) of the cells. In some aspects, the neural network performs recognition of cancerous cells using textural information derived from an image of the cells, among them angular second moment, contrast, coefficient of correlation, sum of squares, difference moment, inverse difference moment, sum average, sum variance, sum entropy, entry, difference variance, difference entropy, information measures, maximal correlation coefficient, coefficient of variation, peak transition probability, diagonal variance, diagonal moment, second diagonal moment, product moment, triangular symmetry and blobness.

Sepsis

In some embodiments, the system and methods disclosed herein are used for the detection and/or identification of sepsis. Without wishing to be bound by theory, plasma cells (e.g., myeloid cells such as white blood cells, lymphocytes, etc.) of a subject with hematologic bacterial infections, such as sepsis, may exhibit different morphological features (e.g., geometry, texture, shape, aspect ratio, area, etc.) than those of a subject without the hematologic bacterial infection. Thus, in some examples, the classification and sorting processes, as provided herein, may be used to diagnosis sepsis.

Sickle Cell Disease

In some embodiments, the system and methods disclosed herein are used for the detection and/or identification of a sickle cell. In some aspects, the system and methods disclosed herein are used to image a cell and to determine if the cell is a sickle cell. The methods of the disclosure may be further used to collect the cells determined to be sickle cells. In some embodiments the cell is from a biological sample from a subject and the methods disclosed herein are used to determine whether the subject suffers from or is susceptible to a sickle cell disease. In some embodiments, the sickle cell disease is a sickle cell anemia.

Crystals in Biological Samples

Current diagnostic methods used to detect crystals in blood and/or urine includes radiological, serological, sonographic, and enzymatic methods.

Urine crystals may be of several different types. Most commonly crystals are formed of struvite (magnesium-ammonium-phosphate), oxalate, urate, cysteine, or silicate, but may also be composed of other materials such as bilirubin, calcium carbonate, or calcium phosphate.

In some embodiments, the system and methods disclosed herein are used for the detection of crystals in biological samples. In some aspects, detected crystals are formed. In some aspects, the biological sample from a subject is imaged according to the methods described herein to determine whether the biological sample comprises a crystal. In some aspects, the biological sample is blood. In some aspects, the blood is venous blood of a subject. In some aspects, the biological sample is urine. In some aspects, the subject is a human, horse, rabbit, guinea pig, or goat. In some aspects, the methods of the disclosure may be further utilized to isolate and collect the crystal from the sample. In some aspects, the biological sample is from a subject and the system and methods of the present disclosure are used to determine whether the subject suffers from or is susceptible to disease or a condition.

In some embodiments, the methods disclosed herein are used for the analysis of a crystal from a biological sample. In some aspects, the methods disclosed herein may be used to image a crystal, and the crystal images may be analyzed for, including but not limited to, crystal shape, size, texture, morphology, and color. In some embodiments, the biological sample is from a subject and the methods disclosed herein are used to determine whether the subject suffers from a disease or a condition. In some example the subject is a human. For example, the methods of the disclosure may be used to analyze crystal in a blood sample of the human subject, and the results may be used to determine whether the subject suffers from pathological conditions, including but not limited to, chronic or rheumatic leukemia. In some aspects, the biological sample is a urine sample.

In some embodiments, the system and methods disclosed herein enable the acquisition of three-dimensional imaging data of crystals, if found in the biological sample, wherein each individual crystal is imaged from a plurality of angles.

In some embodiments, the system and methods disclosed herein comprise a crystal detection system that uses a rapidly trained neural network, wherein the neural network detects crystals by analyzing raw images of a plurality of crystals and provides imaging information from the pixels of the images to a neural network. In some aspects, the neural network performs recognition and identification of a plurality of crystals using information derived from an image of the crystals, among others, the area, the average intensity, the shape, the texture. In some aspects, the neural network performs recognition of crystals using textural information derived from an image of the cells, among them angular second moment, contrast, coefficient of correlation, sum of squares, difference moment, inverse difference moment, sum average, sum variance, sum entropy, entry, difference variance, difference entropy, information measures, maximal correlation coefficient, coefficient of variation, peak transition probability, diagonal variance, diagonal moment, second diagonal moment, product moment, triangular symmetry and blobness.

Liquid Biopsy

A liquid biopsy comprises the collection of blood and/or urine from a cancer patient with primary or recurrent disease and the analysis of cancer-associated biomarkers in the blood and/or urine. A liquid biopsy is a simple and non-invasive alternative to surgical biopsies that enables doctors to discover a range of information about a tumor. Liquid biopsies are increasingly being recognized as a viable, noninvasive method of monitoring a patient's disease progression, regression, recurrence, and/or response to treatment.

In some embodiments, the methods disclosed herein are used for liquid biopsy diagnostics, wherein the biopsy is a liquid biological sample that is passed through the system of the present disclosure. In some aspects, the liquid biological sample that is used for the liquid biopsy is less than 5 mL of liquid. In some aspects, the liquid biological sample that is used for the liquid biopsy is less than 4 mL of liquid. In some aspects, the liquid biological sample that is used for the liquid biopsy is less than 3 mL of liquid. In some aspects, the liquid biological sample that is used for the liquid biopsy is less than 2 mL of liquid. In some aspects, the liquid biological sample that is used for the liquid biopsy is less than 1 mL of liquid. In some aspects, the liquid biological sample that is used for liquid biopsy is centrifuged to get plasma.

In some embodiments, the system and methods of the present disclosure are used for body fluid sample assessment, wherein cells within a sample are imaged and analyzed and a report is generated comprising all the components within the sample, the existence of abnormalities in the sample, and a comparison to previously imaged or tested samples from the same patient or the baseline of other healthy individuals.

In some embodiments, the system and methods of the present disclosure are used for the diagnosis of immune diseases, including but not limited to tuberculosis (TB) and acquired immune deficiency disorder (AIDS), wherein white blood cells are imaged in the system disclosed herein to examine their capacity to release pro- and anti-inflammatory cytokines.

In some embodiments, the system and methods of the present disclosure are used to assess patient immune responses to immunomodulatory therapies by imaging their white blood cells and analyzing the change in their capacity to release pro- and anti-inflammatory cytokines.

In some embodiments, the system and methods of the present disclosure are used to identify the efficacy of therapeutics and/or to guide the selection of agents or their dosage by isolating patients' white blood cells and analyzing the effect of target therapeutics on their capacity to release pro- and anti-inflammatory cytokines.

In some embodiments, the system and methods of the present disclosure are used to isolate pure samples of stem cell-derived tissue cells by obtaining images of cells, and isolating cells with desired phenotype.

Testing Biologically Active Molecules

In some embodiments, the methods disclosed herein are used for biologically active molecule testing, for example drugs. In some embodiments, the methods of the disclosure are sued to collect desired cells from a sample and then treating the desired cells with a biologically active molecule in order to test the effect of the biologically active molecule on the collected cells.

In some embodiments, the methods and systems of the present disclosure are used for identifying the efficacy of therapeutics. In some aspects, identifying the efficacy of therapeutics using the system disclosed herein is carried out by obtaining images of a cell before and after treatment and analyzing the images to determine whether the cell has responded to the therapeutic of interest.

In some embodiments, the system and methods disclosed herein are used for diseased cell detection, wherein the diseased cells are from biological samples and are detected and tracked as they pass through the system of the present disclosure. In some aspects, the diseased cells are isolated and grouped together for further studies.

In some embodiments, the cells used in the methods disclosed herein are live cells. In some aspects, the cells that are classified as diseased cells are isolated and subsequently cultured for potential drug compound screening, testing of a biologically active molecule, and/or further studies.

Although the present disclosure has been described in certain specific aspects, many additional modifications and variations would be apparent to those skilled in the art. It is therefore to be understood that the present disclosure can be practiced otherwise than specifically described without departing from the scope and spirit of the present disclosure. Thus, some embodiments of the present disclosure should be considered in all respects as illustrative and not restrictive.

Point-of-Care Complete Blood Count (CBC)

CBC may provide information about types and numbers of cells in blood or plasma. White blood cell (WBC) count may be used as biomarkers for acute infection and/or inflammation. While an elevated WBC may be associated with infection, inflammation, tissue injury, leukemia and allergy, a low WBC count may be associated with viral infections, immunodeficiency, acute leukemia and bone marrow failure. Thus, an efficient point-of-care CBC may enhance (e.g., expedite) any clinical decision process that requires such information. Thus, a facility (e.g., a hospital, pharmacy, any point-of-care site, etc.) may comprise any subject embodiment of the flow cell of the present disclosure to analyze a subject's blood (or plasma) and obtain the CBC. Furthermore, the flow cell provided herein may provide CBC to track the number of WBCs before and after each treatment for a subject (e.g., chemotherapy treatment for a cancer patient). As such, in some cases, the flow cell provided herein may negate a need for hematological analysis-based CBC, which is often performed in a central or satellite laboratories.

Computer Systems

Figure 16:
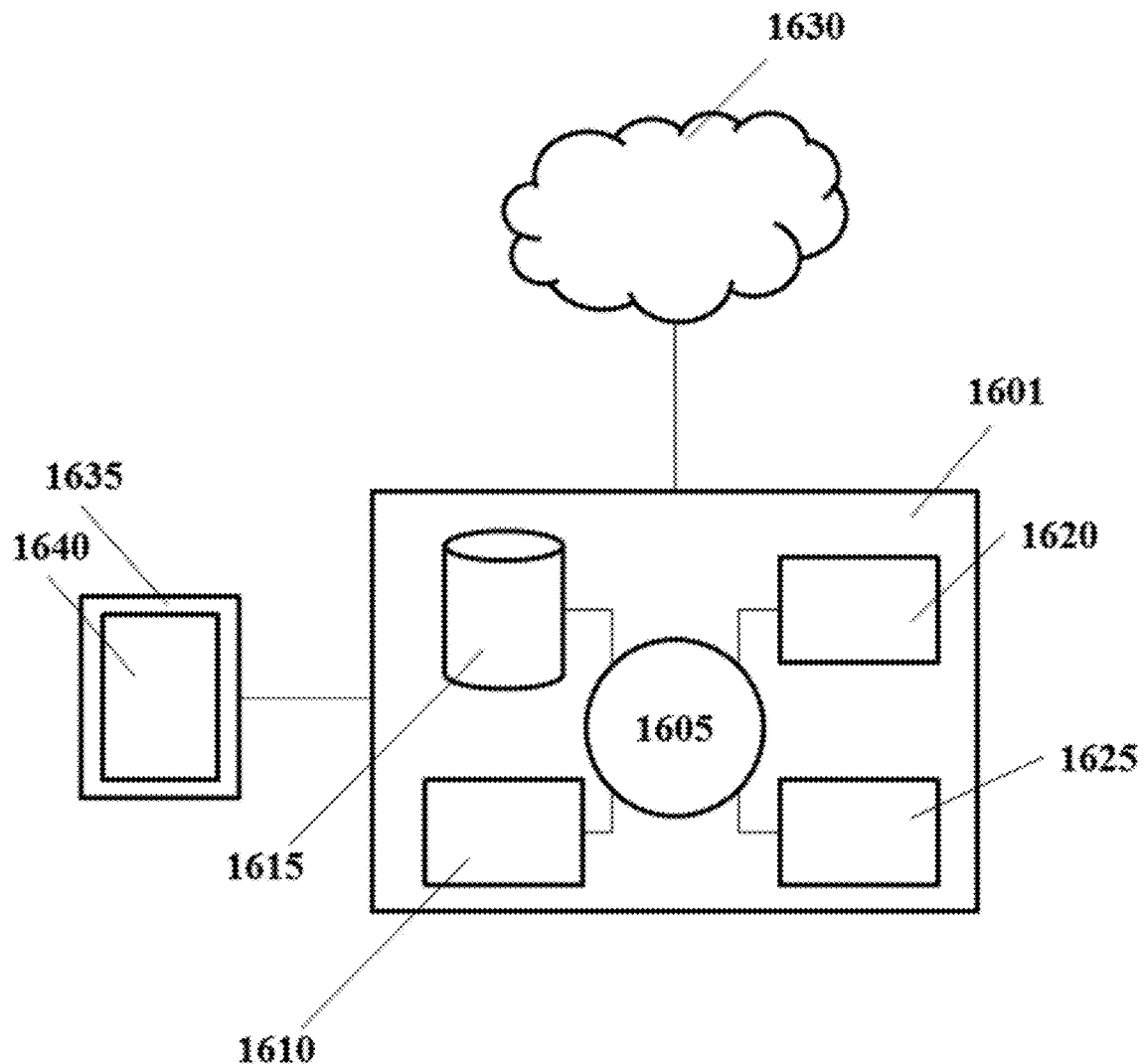
FIG. 16 shows a computer system that is programmed or otherwise configured to implement methods provided herein.

The present disclosure provides computer systems that are programmed to implement methods of the disclosure. FIG. 16 shows a computer system 1601 that is programmed or otherwise configured to capture and/or analyze one or more images of the cell. The computer system 1601 can regulate various aspects of components of the cell sorting system of the present disclosure, such as, for example, the pump, the valve, and the imaging device. The computer system 1601 can be an electronic device of a user or a computer system that is remotely located with respect to the electronic device. The electronic device can be a mobile electronic device.

The computer system 1601 includes a central processing unit (CPU, also "processor" and "computer processor" herein) 1605, which can be a single core or multi core processor, or a plurality of processors for parallel processing. The computer system 1601 also includes memory or memory location 1610 (e.g., random-access memory, read-only memory, flash memory), electronic storage unit 1615 (e.g., hard disk), communication interface 1620 (e.g., network adapter) for communicating with one or more other systems, and peripheral devices 1625, such as cache, other memory, data storage and/or electronic display adapters. The memory 1610, storage unit 1615, interface 1620 and peripheral devices 1625 are in communication with the CPU 1605 through a communication bus (solid lines), such as a motherboard. The storage unit 1615 can be a data storage unit (or data repository) for storing data. The computer system 1601 can be operatively coupled to a computer network ("network") 1630 with the aid of the communication interface 1620. The network 1630 can be the Internet, an internet and/or extranet, or an intranet and/or extranet that is in communication with the Internet. The network 1630 in some cases is a telecommunication and/or data network. The network 1630 can include one or more computer servers, which can enable distributed computing, such as cloud computing. The network 1630, in some cases with the aid of the computer system 1601, can implement a peer-to-peer network, which may enable devices coupled to the computer system 1601 to behave as a client or a server.

The CPU 1605 can execute a sequence of machine-readable instructions, which can be embodied in a program or software. The instructions may be stored in a memory location, such as the memory 1610. The instructions can be directed to the CPU 1605, which can subsequently program or otherwise configure the CPU 1605 to implement methods of the present disclosure. Examples of operations performed by the CPU 1605 can include fetch, decode, execute, and writeback.

The CPU 1605 can be part of a circuit, such as an integrated circuit. One or more other components of the system 1601 can be included in the circuit. In some cases, the circuit is an application specific integrated circuit (ASIC).

The storage unit 1615 can store files, such as drivers, libraries and saved programs. The storage unit 1615 can store user data, e.g., user preferences and user programs. The computer system 1601 in some cases can include one or more additional data storage units that are external to the computer system 1601, such as located on a remote server that is in communication with the computer system 1601 through an intranet or the Internet.

The computer system 1601 can communicate with one or more remote computer systems through the network 1630. For instance, the computer system 1601 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1601 via the network 1630.

Methods as described herein can be implemented by way of machine (e.g., computer processor) executable code stored on an electronic storage location of the computer system 1601, such as, for example, on the memory 1610 or electronic storage unit 1615. The machine executable or machine readable code can be provided in the form of software. During use, the code can be executed by the processor 1605. In some cases, the code can be retrieved from the storage unit 1615 and stored on the memory 1610 for ready access by the processor 1605. In some situations, the electronic storage unit 1615 can be precluded, and machine-executable instructions are stored on memory 1610.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1601 can include or be in communication with an electronic display 1635 that comprises a user interface (UI) 1640 for providing, for example, the one or more images of the cell that is transported through the channel of the cell sorting system. In some cases, the computer system 1601 can be configured to provide a live feedback of the images. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1605. The algorithm can be, for example, a deep learning algorithm to enable sorting of the cell.

EXAMPLES

The following specific examples are illustrative and non-limiting. The examples described herein reference and provide non-limiting support to the various embodiments described in the preceding sections.

Example 1. Non-Invasive Prenatal Testing

Sample Preparation: Five to ten mL of maternal peripheral blood will be collected into an ethylene diamine tetraacetic acid (EDTA)-containing tube and a plain tube. For women undergoing amniocentesis, maternal blood will be collected prior to the procedure. Maternal blood samples will be processed between 1 to 3 hours following venesection. Blood samples will be centrifuged at 3000 g and plasma and serum will be carefully removed from the EDTA-containing and plain tubes, respectively, and transferred into plain polypropylene tubes. The plasma or serum samples must remain undisturbed when the buffy coat or the blood clot are removed. Following removal of the plasma samples, the red cell pellet and buffy coat will be saved for processing in the system of the present disclosure.

Sample Testing: Cells from maternal serum or plasma acquired from a pregnant female subject may be imaged using the system and methods of the present disclosure, wherein the cells are not labelled and placed in a flow. The cells will be imaged from different angles. In some aspects, the cells will be housed in a flow channel within the system of the present disclosure, wherein the flow channel has walls formed to space the plurality of cells within a single streamline. In some aspects, the cells will be housed in a flow channel within the system of the present disclosure, wherein the flow channel has walls formed to rotate the plurality of the cells within a single streamline.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A cell flow system comprising:
   a flow channel configured to transport a cell through the flow channel;
   a plurality of sub-channels in fluid communication with the flow channel via a sorting junction;
   at least one sensor operatively coupled to the sorting junction, wherein the at least one sensor is configured to detect an actual arrival time of the cell at the sorting junction; and
   a processor configured to:
   (1) analyze (i) the actual arrival time of the cell at the sorting junction and (ii) a predicted arrival time of the cell at the sorting junction; and
   (2) control an operation of the cell flow system based on the analysis in (1).

2. The cell flow system of claim 1, wherein the processor is configured to compare (i) the actual arrival time and (ii) the predicted arrival time.

3. The cell flow system of claim 1, wherein the predicted arrival time is obtained prior to the detection of the actual arrival time.

4. The cell flow system of claim 1, wherein the predicted arrival time comprises a probability of the cell's arrival at the sorting junction.

5. The cell flow system of claim 1, wherein the processor is configured to determine the predicted arrival time of the cell by a deep learning algorithm.

6. The cell flow system of claim 5, wherein the processor is further configured to update the deep learning algorithm based on the analysis in (1).

7. The cell flow system of claim 6, wherein the deep learning algorithm is updated in real time.

8. The cell flow system of claim 1, wherein the at least one sensor is disposed adjacent to the sorting junction.

9. The cell flow system of claim 1, wherein the at least one sensor is further configured to obtain data indicative of a velocity of the cell at a position along the flow channel and upstream of the sorting junction.

10. The cell flow system of claim 9, wherein the at least one sensor comprises an optical device.

11. The cell flow system of claim 10, wherein the optical device comprises one or more cameras configured to capture one or more images of the cell.

12. The cell flow system of claim 11, wherein the one or more images comprise a two-dimensional image.

13. The cell flow system of claim 11, wherein the one or more images comprise a three-dimensional image.

14. The cell flow system of claim 10, wherein the optical device comprises one or more laser detectors.

15. The cell flow system of claim 14, wherein the one or more laser detectors comprise a multi-point laser detector.

16. The cell flow system of claim 9, wherein the processor is configured to determine the predicted arrival time based on (i) the velocity of the cell and (ii) a distance between the position and the sorting junction.

17. The cell flow system of claim 1, wherein the operation comprises one or more members selected from the group consisting of (i) focusing a plurality of cells into a streamline within the flow channel, (ii) rotating the plurality of cells within the flow channel, (iii) adjusting a velocity of the plurality of cells within the flow channel, and (iv) one or more cell classification algorithms.

18. The cell flow system of claim 17, wherein the operation comprises two or more members selected from the group consisting of (i)-(iv).

19. The cell flow system of claim 1, wherein the cell is from a biological sample of a subject.

20. The cell flow system of claim 19, wherein the biological sample comprises blood or serum.

* * * * *